US012600766B2

(12) United States Patent
Seredenina et al.

(10) Patent No.: US 12,600,766 B2
(45) Date of Patent: Apr. 14, 2026

(54) ANTI-TDP-43 BINDING MOLECULES AND USES THEREOF

(71) Applicant: AC Immune SA, Lausanne (CH)

(72) Inventors: Tamara Seredenina, Lausanne (CH); Tamar Magdalena Ziehm, Lausanne (CH); Tariq Afroz, Lausanne (CH)

(73) Assignee: AC Immune SA, Lausanne (CH)

( * ) Notice: Subject to any disclaimer, the term of this patent is extended or adjusted under 35 U.S.C. 154(b) by 1109 days.

(21) Appl. No.: 17/613,444

(22) PCT Filed: May 22, 2020

(86) PCT No.: PCT/EP2020/064335
§ 371 (c)(1),
(2) Date: Nov. 22, 2021

(87) PCT Pub. No.: WO2020/234473
PCT Pub. Date: Nov. 26, 2020

(65) Prior Publication Data
US 2022/0315648 A1 Oct. 6, 2022

(30) Foreign Application Priority Data

| | | |
|---|---|---|
| May 23, 2019 | (EP) | 19176314 |
| Sep. 6, 2019 | (EP) | 19195916 |
| Nov. 7, 2019 | (EP) | 19207839 |
| Mar. 4, 2020 | (EP) | 20161060 |

(51) Int. Cl.
| | |
|---|---|
| *C07K 16/18* | (2006.01) |
| *A61P 25/00* | (2006.01) |
| *G01N 33/68* | (2006.01) |
| *A61K 39/00* | (2006.01) |

(52) U.S. Cl.
CPC ............. *C07K 16/18* (2013.01); *A61P 25/00* (2018.01); *G01N 33/6896* (2013.01); *A61K 2039/505* (2013.01); *C07K 2317/34* (2013.01); *C07K 2317/92* (2013.01); *G01N 2800/28* (2013.01); *G01N 2800/2814* (2013.01); *G01N 2800/2821* (2013.01); *G01N 2800/2835* (2013.01); *G01N 2800/2878* (2013.01); *G01N 2800/52* (2013.01)

(58) Field of Classification Search
CPC ............... C07K 16/18; C07K 2317/34; C07K 2317/92; C07K 2317/52; A61P 25/00; A61P 25/02; A61P 25/28; G01N 33/6896; G01N 2800/28; G01N 2800/2814; G01N 2800/2821; G01N 2800/2835; G01N 2800/2878; G01N 2800/52; G01N 33/6893; A61K 2039/505
See application file for complete search history.

(56) References Cited

U.S. PATENT DOCUMENTS

| | | | |
|---|---|---|---|
| 5,688,511 A | 11/1997 | Gaynor et al. | |
| 2010/0136573 A1 * | 6/2010 | Petrucelli | C07K 14/4711 435/7.1 |

FOREIGN PATENT DOCUMENTS

| | | | | |
|---|---|---|---|---|
| WO | 2003080672 | 10/2003 | | |
| WO | WO-2008151055 A1 * | 12/2008 | ......... | C07K 14/4711 |
| WO | 2013061163 | 5/2013 | | |
| WO | WO-2013061163 A2 * | 5/2013 | ............. | A61P 43/00 |
| WO | 2017027691 A1 | 2/2017 | | |
| WO | 2018218352 | 12/2018 | | |

OTHER PUBLICATIONS

Almagro, J.C. & Fransson, J. Humanization of antibodies. Frontiers in Bioscience 2008; 13:1619-33 (Year: 2008).*
Dall'Acqua et al. Antibody humanization by framework shuffling. Methods 2005; 36:43-60 (Year: 2005).*
Edwards et al. The remarkable flexibility of the human antibody repertoire; isolation of over one thousand different antibodies to a single protein, BLyS. J. Mol. Biol. 2003, 334:103-118 (Year: 2003).*
Janeway Jr et al., Immunology, 3rd Edition, 1997 Garland Publishing Inc., section 3, Structure of the Antibody Molecule and Immunoglobulin Genes, pp. 3:1-3:11. (Year: 1997).*
Kanyavuz et al. Breaking the law: unconventional strategies for antibody diversification. Nature Review Immunology, 2019, 19: 355-368 (Year: 2019).*
Lloyd et al. Modelling the human immune response: performance of a 1011 human antibody repertoire against a broad panel of therapeutically relevant antigens. Protein Engineering Design & Selection. 2009, 22;3:159-168 (Year: 2009).*
Berning et al. (2019) "The Pathobiology of TDP-43 C-Terminal Fragments in ALS and FTLD" Frontiers in Neuroscience, DOI: 10.3389/fnins.2019.00335, 27 pgs.
Wils et al. (2010) "TDP-43 transgenic mice develop spastic paralysis and neuronal inclusions characteristic of ALS and frontotemporal lobar degeneration" PNAS, 107(8):3858-3863.

(Continued)

*Primary Examiner* — Misook Yu
*Assistant Examiner* — Grace H Lunde
(74) *Attorney, Agent, or Firm* — Brian E. Davy; Bozicevic, Field & Francis LLP

(57) ABSTRACT

The present invention is in the field of transactive response DNA binding protein with a molecular weight of 43 kDa (TARDB or also TDP-43). The invention relates to TDP-43 specific binding molecules, in particular to anti-TDP-43 antibodies or an antigen-binding fragment or a derivative thereof and uses thereof. The present invention provides means and methods to diagnose, prevent, alleviate and/or treat a disease, disorder and/or abnormality associated with TDP-43 aggregates including but not limited to Frontotemporal dementia (FTD), amyotrophic lateral sclerosis (ALS), Alzheimer's disease (AD), Parkinson's disease (PD), Chronic Traumatic Encelopathy (CTE), and limbic-predominant age-related TDP-43 encephalopathy (LATE).

15 Claims, 7 Drawing Sheets

Specification includes a Sequence Listing.

(56) References Cited

OTHER PUBLICATIONS

Johnson et al. (2008) "A yeast TDP-43 proteinopathy model: Exploring the molecular determinants of TDP-43 aggregation and cellular toxicity" PNAS, 105(17):6439-6444.

Search Report Office Action dated Sep. 13, 2024, Appl. No. UAE P6002133/2021, 13 pp.

Office Action dated Nov. 9, 2023, Appl. No. CA 3, 137,882, 6 pp.

Rudikoff et al. (1982) "Single amino acid substitution altering antigen-binding specificity" Proc. Nat. Acad. Sci. USA, 79:1979-1983.

Tamura et al. (2000) "Structural Correlates of an Anticarcinoma Antibody: Identification of Specificity-Determining Residues (SDRs) and Development of a Minimally Immunogenic Antibody Variant by Retention of SDRs Only" The Journal of Immunology, 1432-1441.

Office Action with English translation dated Aug. 30, 2023, Appl. No. 202080038441.4, 17 pp.

Arai et al. (2006) "TDP-43 is a component of ubiquitin-positive tau-negative inclusions in frontotemporal lobar degeneration and amyotrophic lateral sclerosis" Biochemical and Biophysical Research Communications, 351:602-611.

Office Action with English translation dated Jul. 26, 2023, Appl. No. EA202193215, 10 pp.

Yarilin (1999) Fundamentals of Immunology: Textbook.— Moscow: Medicine, 608:172-174 (including machine translation).

Kwong et al. (2014) "Novel monoclonal antibodies to normal and pathologically altered human TDP-43 proteins" Acta Neuropathologica Communications, 2:33.

Office Action with English Summary dated Jul. 23, 2024, Appl. No. JP2021-569353, 8 pp.

Tsuji et al. (2012) "Epitope mapping of antibodies against TDP-43 and detection of protease-resistant fragments of pathological TDP-43 in amyotrophic lateral sclerosis and frontotemporal lobar degeneration" Biochemical and Biophysical Research Communications, 417:116-121.

* cited by examiner

% aggregation normalized to isotype control

Quantification of Iba1 staining by immunohistochemistry in brain cortex

Quantification of TDP-43 in CSF

ANTI-TDP-43 BINDING MOLECULES AND USES THEREOF

FIELD OF THE INVENTION

The present invention is in the field of transactive response DNA binding protein with a molecular weight of 43 kDa (TARDB or also TDP-43). The invention relates to TDP-43 specific binding molecules, in particular to anti-TDP-43 antibodies or an antigen-binding fragment or a derivative thereof and uses thereof. The present invention provides means and methods to diagnose, prevent, alleviate and/or treat a disease, a disorder and/or abnormality associated with TDP-43, in particular associated with TDP-43 aggregates, or TDP-43 proteinopathy, including but not limited to Frontotemporal dementia (FTD), amyotrophic lateral sclerosis (ALS), Alzheimer's disease (AD), Parkinson's disease (PD), Chronic Traumatic Encelopathy (CTE), and limbic-predominant age-related TDP-43 encephalopathy (LATE).

BACKGROUND

Age-associated brain disorders characterized by pathological aggregation of proteins in the central nervous system (CNS) (proteinopathies) and peripheral organs represent one of the leading causes of disability and mortality in the world. The best characterized protein that forms aggregates is amyloid beta in Alzheimer's disease and related disorders. Other disease-associated, aggregation-prone proteins leading to neurodegeneration include but are not limited to Tau, alpha-synuclein (aSyn, a-syn), huntingtin, fused in sarcoma (FUS), dipeptide repeat proteins (DPRs) produced by unconventional translation of the C9orf72 repeat expansion, superoxide dismutase 1 (SOD1), and TDP-43. Diseases involving TDP-43 aggregates are generally listed as TDP-43 proteinopathies including, but not limited to, ALS and FTD.

I. TDP-43 Introduction

Transactive response (TAR) DNA binding protein 43 kDa (TDP-43) is a 414-amino acid protein encoded by the TARDBP gene on chromosome 1p36.2 (ALS10). TARDBP is comprised of six exons (exon 1 is non-coding; exons 2-6 are protein-coding). TDP-43 belongs to the family of heterogeneous ribonucleoprotein (hnRNP) RNA binding proteins (Wang et al., Trends in Molecular Medicine Vol. 14 No. 11, 2008, 479-485; Lagier-Tourenne et al., Human Molecular Genetics, 2010, Vol. 19, Review Issue 1 R46-R64). TDP-43 contains five functional domains (FIG. 1 in Warraich et al., The International Journal of Biochemistry & Cell Biology 42 (2010) 1606-1609): two RNA recognition motifs (RRM1 and RRM2), which have two highly conserved hexameric ribonucleoprotein 2 (RNP2) and octameric ribonucleioprotein 1 (RNP1) regions, a nuclear export signal (NES) and a nuclear localization signal (NLS) enabling it to shuttle between the nucleus and the cytoplasm transporting bound mRNA, and a glycine rich domain at the C-terminal, which mediates protein-protein interactions. TDP-43 is involved in multiple aspects of RNA processing, including transcription, splicing, transport, and stabilization (Buratti and Baralle, FEBS Journal 277 (2010) 2268-2281). It is a highly conserved, ubiquitously expressed protein with a tightly autoregulated expression level that shuttles continuously between the nucleus and cytoplasm, but is predominantly localized to the nucleus. In 2006, TDP-43 was identified as the protein that accumulates in the vast majority of cases of frontotemporal lobar degeneration (FTLD) with tau-negative, ubiquitin-positive inclusions (then referred to as FTLD-TDP), and in most cases of amyotrophic lateral sclerosis (ALS) (Arai et al., Biochemical and Biophysical Research Communications 351 (2006) 602-611; Neumann et al., Science 314, (2006), 130-133).

Thirty-eight negative-dominant mutations in TDP-43 have been identified in sporadic and familial ALS patients as well as in patients with inherited FTD mainly located in the glycine rich domain (FIG. 1 in Lagier-Tourenne and Cleveland, Cell 136, 2009, 1001-1004). TDP-43 is inherently aggregation-prone, as shown by sedimentation assays, and this propensity is further increased by some of the ALS-associated TARDBP mutations (Ticozzi et al., CNS Neurol. Disord. Drug Targets. 2010, 9(3), 285-296.) connecting TDP-43 aggregation with clinical disease manifestation.

II. TDP-43 in Neurodegeneration

TDP-43 aggregates have been identified in a growing list of neurodegenerative conditions (Lagier-Tourenne et al., Human Molecular Genetics, 2010, Vol. 19, Review Issue 1 R46-R64), including but not limited to: Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy (CTE), Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known as Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)), Traumatic Brain Injury (TBI), Dementia with Lewy Bodies (DLB) or Parkinson's Disease (PD).

Aggregated TDP-43 from patient brains shows a number of abnormal modifications, including hyperphosphorylation, ubiquitination, acetylation and C-terminal fragments through proteolytic cleavage (Arai et al., Biochemical and Biophysical Research Communications 351 (2006) 602-611; Neumann et al., Science 314, (2006), 130-133; Neumann et al., Acta Neuropathol. (2009) 117: 137-149; Hasegawa et al., (2008) Annals of Neurology Vol 64 No 1, 60-70; Cohen et al., Nat Commun. 6: 5845, 2015). Another characteristic feature of TDP-43 pathology is redistribution and accumulation of TDP-43 from nucleus to cytoplasm. The hallmark lesions of FTLD-TDP are neuronal and glial cytoplasmic inclusions (NCI and GCI, respectively) and dystrophic neurites (DN) that are immunoreactive for TDP-43, as well as ubiquitin and p62, but negative for other neurodegenerative disease-related proteins. Differences in inclusion morphology and tissue distribution thereof are associated with specific mutations and/or clinical representations. Four types of TDP-43 pathology are described so far by histological classification (Mackenzie and Neumann, J. Neurochem. (2016) 138 (Suppl. 1), 54-70). FTLD-TDP type A cases are characterized by abundant short dystrophic neuritis (DN) and compact oval or crescentic NCI, predominantly in layer II of the neocortex (FIG. 2*f* in Mackenzie et al., 2016 J. Neurochem. 138 (Suppl. 1), 54-70). Cases with this pathology usually present clinically with either behavioral-variant frontotemporal dementia (bvFTD) or nonfluent/agrammatic variants of Primary Progressive Aphasia (nfvPPA) and are associated with progranulin (GRN) mutations. Type B cases show moderate numbers of compact or granular NCI in both superficial and deep cortical layers with relatively few DN and NII (neuronal intranuclear inclusions; FIG. 2*g* in Mackenzie et al., 2016 J. Neurochem. 138 (Suppl. 1), 54-70). Most cases with co-appearance of FTD and ALS symptoms are found to have FTLD-TDP type B pathology. Type C cases have an abundance of long, tortuous neurites, predominantly in the superficial cortical laminae, with few or no NCI (FIG. 2*j* in Mackenzie et al., 2016 J. Neurochem. 138 (Suppl. 1), 54-70). This pathology is particularly found in cases presenting with semantic variant of primary progressive aphasia (svPPA). FTLD-TDP type D displays with abundant lentiform neuronal intranuclear inclusions (NII) and short DN in the neocortex with only rare NCI (FIG. 2*k* in Mackenzie et al., 2016 J. Neurochem. 138 (Suppl. 1), 54-70). Type E is characterized by granulofilamentous neuronal inclusions (GFNIs) and very fine, dot-like neuropil aggregates affecting all neocortical layers in addition to curvilinear oligodendroglial inclusions in the white matter (Edward B. Lee et al., Acta Neuropathol. 2017 July; 134(1): 65-78.). This pattern of pathology is only found in cases with VCP in association with inclusion body myositis.

III. TDP-43 in FTD

Frontotemporal dementia (FTD) is a clinical term that covers a wide spectrum of disorders based on the degeneration of frontal and temporal lobes—a pathological feature termed frontotemporal lobar degeneration (FTLD). FTD is the second most abundant cause of early degenerative dementias in the age group below 65 years (Le Ber, Revue Neurologique 169 (2013) 811-819). FTD is presented by several syndromes including bvFTD which is characterized by changes in personality and behavior; semantic dementia (SD) and progressive nonfluent aphasia (PNFA) characterized by changes in the language function; corticobasal syndrome (CBS), progressive supranuclear palsy syndrome and motor neuron disease (FTD-MND) characterized by movement dysfunction. Clinical diagnosis of these syndromes is complicated and final conclusion can only be achieved through postmortem histopathological analysis to detect aggregated protein and define affected brain regions. In terms of pathological, proteinaceous inclusions, about 45% of cases show pathological accumulation of misfolded Tau, 45% of cases have pathological TDP-43 and a smaller subgroup has aggregates of FUS and other proteins.

IV. TDP-43 in ALS

Amyotrophic lateral sclerosis (ALS) is a neurodegenerative disorder characterized by the premature loss of upper and lower motor neurons. The progression of ALS is marked by fatal paralysis and respiratory failure with a disease course from diagnosis to death of 1 to 5 years. In most cases of sporadic ALS, the neuropathology is characterized by abnormal cytoplasmic accumulations of TDP-43 in neurons and glia of the primary motor cortex, brainstem motor nuclei, spinal cord and the associated white matter tracts. ALS with dementia involves accumulation of TDP-43 in extramotor neocortex and hippocampus. The role of phosphorylation of TDP-43 in ALS patients has been explored with the help of antibodies that specifically bind to phosphorylated TDP-43 in nuclear and cytoplasmic inclusions with amino acids S379, S403, S404, S409, S410 as the major sites of phosphorylation of TDP-43 (Hasegawa et al., Ann Neurol 2008; 64: 60-70; Neumann et al., Acta Neuropathol (2009) 117: 137-149).

V. TDP-43 in AD and Other Diseases

TDP-43 pathology occurs in up to 57% of brains of patients with Alzheimer's disease (Josephs K A et al., Acta Neuropathol. 2014; 127(6): 811-824; Josephs K A et al., Acta Neuropathol. 2014; 127(3): 441-450; McAleese et al., Brain Pathol. 2017 July; 27(4): 472-479). TDP-43 aggregation is associated with patient's age and correlates with cognitive decline, memory loss and medial temporal atrophy in AD. It appears that in AD TDP-43 represents a secondary or independent pathology that shares overlapping brain distribution with amyloid beta and tau pathologies in the medial temporal lobe. Pathologic TDP-43 follows a stereotypical pattern of progressive deposition that has been described by the so-called TDP-43 in AD (TAD) staging scheme: TDP-43 first deposits in the amygdala (stage I) followed by hippocampus, limbic, temporal, and finally the frontostriatum (stage V) (Josephs K A et al., Acta Neuropathol. 2014; 127(6): 811-824; Josephs K A et al., Acta Neuropathol. 2014; 127(3): 441-450).

VI. TDP-43 Spreading

Although ALS and FTD onset and first symptoms vary significantly between patients, the common feature of disease progression is spreading of pathology from an initial focal area to most neurons. The continuous worsening of symptoms might be explained by the progressive spread of TDP-43 pathology. TDP-43 pathology in an ALS patient's brain appears to be spreading in a four-stage process and it is believed that propagation occurs transsynaptically via corticofugal axonal projections using anterograde axonal transport (Brettschneider et al., Ann Neurol. 2013 July; 74(1): 20-38.). Recent experimental evidence supports the hypothesis of protein propagation in neuronal tissue for amyloid-beta, Tau, alpha-synuclein and TDP-43 by a prion-like mechanism (Hasegawa et al., 2017), with starting points and the topographical spreading patterns being distinct for the four proteins (Brettschneider J et al., Nature Rev. Neuroscience, 2015, 109). The common, disease unifying mechanism is believed to be based on the cell-to-cell spreading of pathological protein aggregates. This mechanism consists of the release of aggregates from a diseased cell, uptake by a naïve cell and seeding of the pathological protein conformation by a templated conformational change of endogenous proteins.

TDP-43 cell-to cell spreading has been studied at a molecular level in few in vitro models, where insoluble TDP-43 preparations from patient brain are able to induce intracellular aggregate formation in receptor cells (Nonaka et al., Cell Reports 4 (2013), 124-134; Feiler et al., 2015; Porta et al., Nat. Comm., 2018). Further it has been observed that intracellular TDP-43 aggregates are released in association with exosome prior to spreading to the next cell (Nonaka et al., Cell Reports 4 (2013, 124-134)). Similarly, adenovirus-transduced TDP-43 expression lead to cytoplasmic aggregates which were phosphorylated, ubiquitinated and more importantly acted as seeds initiating cell to cell spreading (Ishii et al., PLoS ONE 12(6): e0179375, 2017). The patient-derived pathological TDP-43 can lead to widespread deposition of endogenous TDP-43 following intracerebral inoculation into transgenic and wildtype mice (Porta et al., Nat. Comm., 2018).

VII. Prevention and Treatment of TDP-43 Proteinopathies

TDP-43 aggregation and spreading of pathology are major hallmarks of ALS and FTD—fatal diseases for which currently no cure is available. Mutations in TDP-43 are associated with familial cases of ALS and FTD providing causative link between TDP-43 misfolding and disease progression.

VIII. Diagnostics of TDP-43 Proteinopathies

The diagnosis of FTD based on clinical manifestations is insufficient since the clinical representation can overlap with other diseases in particular in the earlier stages.

A number of approaches aim at development of biochemical biomarkers to distinguish different types of FTD pathology. Development of antibodies against different conformations of TDP-43 may permit generating more sensitive and specific diagnostic tools. In parallel to biochemical biomarkers the development of imaging biomarkers may enable early and specific detection of the pathology in TDP-43 proteinopathies. The ability to image TDP-43 deposition in the brain may be a substantial achievement for diagnosis and drug development for TDP-43 proteinopathies. Using cell permeable antibody fragments could enable such detection.

The earliest event in neurodegenerative diseases based on misfolding of different proteins is the acquisition of an alternative conformation that renders the protein toxic. Moreover, this misfolded conformation can self-propagate by recruiting the endogenous, normal protein into the misfolded conformation as mechanistic basis for the observed spread through affected tissue.

To develop antibodies against different conformational states of a given protein, supramolecular antigenic constructs were designed in which the conformation of the presented antigen was controlled to raise conformational-specific antibodies against a given target in a specific conformational state (WO2012/055933 and WO2012/020124). Conformational-specific antibodies offer many advantages since they can discriminate between the disease-associated and the functional, endogenous conformation of these proteins. This approach offers many advantages in the therapeutic application since such antibodies are less likely to be adsorbed by the normal conformation of proteins while targeting the misfolded, disease associated isoform thereof. Similar to this for diagnostic application such antibodies only recognize the disease-associated, structural state of a protein, which is paramount for the development of the sensitive and specific diagnostics.

The use of a TDP-43-based biomarker in TDP-43 proteinopathies still remains to be established. Such evaluation has been hindered in part due to the lack of high affinity antibodies that can be employed in a suitable immunoassay for quantification of pathological TDP-43 in biofluids (Feneberg et al., Molecular Neurobiology, 2018).

Therefore, there is a clear need for biomarkers able to detect misfolded aggregated TDP-43 and non-aggregated physiological TDP-43, in particular in a human sample, for diagnosing different types of TDP-43 proteinopathies and/or for monitoring efficacy of therapeutic drugs used for treatment of diseases, disorders and abnormalities associated with TDP-43, in particular associated with TDP-43 aggregates or TDP-43 proteinopathy.

The TDP-43 proteinopathies are defined as a set of neurodegenerative disorders characterised by pathological TDP-43.

IX. Prior Art

Patent application WO 2008/151055 discloses methods and materials for using the levels of TDP-43 polypeptides and/or TDP-43 polypeptide cleavage products (e.g. 25 kD and 35 kD TDP-43 polypeptide cleavage products) in a biological fluid to determine whether or not a mammal has a neurodegenerative disease.

Patent application WO 2013/061163 discloses TDP-43 specific binding molecules including polypeptides such as human antibodies as well as fragments, derivatives and variants thereof.

SUMMARY

In view of the foregoing, there is a need for anti TDP-43 binding molecules which bind misfolded aggregated TDP-43 and non-aggregated physiological TDP-43, particularly human TDP-43. Moreover, the development of sensitive and specific biomarkers allowing the differentiation between types of pathology within the FTD spectrum is an urgent task.

The technical problem is solved by the embodiments provided herein.

Accordingly, the invention relates to binding molecules, in particular antibodies or antigen-binding fragments thereof, which specifically recognize misfolded aggregated TDP-43 and non-aggregated physiological TDP-43. Within the invention, misfolded TDP-43 includes misfolded monomeric and/or misfolded oligomeric and/or misfolded aggregated and/or post-translationally modified and/or misfolded truncated TDP-43. Post-translationally modified TDP-43 comprises phosphorylated, ubiquitylated, acetylated, sumoylated, and/or methylated TDP-43. Physiological TDP-43 includes soluble nuclear TDP-43. It is demonstrated herein that the binding molecules of the invention are capable of binding pathological TDP-43, including TDP-43 aggregates and phosphorylated TDP-43 (see Example 13). Thus, the invention provides binding molecules, in particular antibodies or antigen-binding fragments thereof, which specifically recognize misfolded aggregated TDP-43 and non-aggregated physiological TDP-43. Such binding molecules are referred to herein as "pan-TDP-43" binding molecules, in particular pan-TDP-43 antibodies. As explained herein, the TDP-43 binding molecules of the invention may bind misfolded aggregated TDP-43 and non-aggregated physiological TDP-43 equally, or to one preferentially to the other whilst binding to both categories of TDP-43 specifically. The invention also provides the binding molecules, in particular antibodies or antigen-binding fragments thereof, for the prevention, alleviation, treatment and/or diagnosis of diseases, disorders and abnormalities associated with TDP-43, in particular associated with TDP-43 aggregates, or TDP-43 proteinopathy. The invention also provides the binding molecules, in particular antibodies or antigen-binding fragments thereof, for detecting and/or understanding (i.e. identifying) the specific type of pathology causing neurodegeneration. Envisaged are uses as diagnostic biomarkers enabling more efficient and precise subject selection for longitudinal monitoring in clinical studies, supporting the development of novel therapeutics for TDP-43 proteinopathies.

The invention also provides the TDP-43 binding molecules, in particular antibodies or antigen-binding fragments thereof, as medicine (therapeutic agent).

Without wishing to be bound by theory, the present invention was developed based on the assumption that modified conformation-specific antigenic peptides and peptide fragments derived from TDP-43 protein or the whole TDP-43 protein and the antibodies obtainable or obtained by said peptides or fragments or the whole TDP-43 protein block TDP-43 cell-to-cell propagation, and/or disaggregate TDP-43 aggregates and/or block TDP-43 seeding and/or inhibit the aggregation of TDP-43 protein or fragments thereof. The binding molecules of the invention, in particular polypeptides, more particularly antibodies or antigen-binding fragments thereof, bind to misfolded aggregated TDP-43, particularly to cytoplasmic and extracellular misfolded TDP-43. The binding molecules of the invention, in particular polypeptides, more particularly antibodies or antigen-binding fragments thereof, bind to full-length TDP-43 and/or truncated TDP-43. In one embodiment, the binding molecules of the invention, in particular polypeptides, more particularly antibodies or antigen-binding fragments thereof, specifically bind to cytoplasmic misfolded TDP-43.

Misfolded aggregated, or pathology-associated, TDP-43 is composed of TDP-43 proteins that lose its normal folding (i.e. are misfolded) and localization. Misfolded aggregated TDP-43 can be found in preinclusions and in neuronal and glial cytoplasmic inclusions (NCI and GCI, respectively), neuronal intranuclear inclusions (NII) and dystrophic neurites (DN) that are immunoreactive for TDP-43.

Non-aggregated physiological TDP-43 is physiologically functional TDP-43 protein predominantly located in the nucleus and shuttling to the cytoplasm, being in a status able to exhibit its desired function in an in vivo cellular environment.

The binding molecules of the invention, in particular the antibodies or antigen-binding fragments thereof, surprisingly have at least one, preferably two, more preferably three, even more preferably all four of the following characteristics:

blocking TDP-43 cell-to-cell propagation;
disaggregating TDP-43 aggregates;
inhibiting the aggregation of TDP-43 protein or fragments thereof;
blocking TDP-43 seeding.

Independent of the combination of one, two, three or four above listed characteristics, the binding molecules, preferably antibodies or antigen-binding fragments thereof, of the invention may ameliorate/inhibit/reduce the formation of TDP-43 pathology in an in vivo model of TDP-43 proteinopathies and more importantly in patients with TDP-43 pathology.

The TDP-43 binding molecules of the invention, in particular the antibodies or antigen-binding fragments thereof, may recruit and/or activate microglia. More specifically, it is shown herein (see Example 10 and FIG. 5) that TDP-43 binding molecules of the invention may affect microglial morphology in terms of cell size and activation state. This may contribute to the reduction of TDP-43 pathology demonstrated by the TDP-43 binding molecules of the invention.

In the present invention, the binding molecules, in particular antibodies or antigen-binding fragments thereof, specifically recognize TDP-43. Binding molecules of the invention include polypeptides and/or antibodies and/or antigen-binding fragments thereof specific to/for the TDP-43 protein. "Specifically recognize TDP-43" means that the binding molecules of the invention specifically, generally, and collectively, bind to TDP-43, in particular some epitopes within TDP-43, in particular an epitope exposed/accessible in one or more pathological conformation(s) of TDP-43 protein, with greater affinity than for other epitopes. The binding molecules of the invention, in particular polypeptides, more particularly antibodies or antigen-binding fragments thereof, that specifically bind to TDP-43, specifically recognize misfolded aggregated TDP-43 and non-aggregated physiological TDP-43. In a preferred embodiment, full-length human TDP-43 comprises, preferably has, the sequence of SEQ ID NO: 1. In another preferred embodiment of the invention, the binding molecules, in particular antibodies or antigen-binding fragments thereof, specifically bind to defined binding regions within full-length and/or truncated TDP-43, wherein the binding region preferably is comprised within amino acids 181-195, 199-213, 307-321, 352-366, 389-411, 397-411 or 140-200, more preferably the binding regions is comprised within amino acids 183-188, 203-213, 204-208, 204-211, 205-210, 316-323, 358-361, 400-405, 400-406 or 400-412, of the full-length human TDP-43 having the sequence of SEQ ID NO:1. Accordingly, the binding molecules, in particular antibodies or antigen-binding fragments thereof, preferably specifically bind to peptides comprising, preferably consisting of, binding regions consisting of amino acids 181-195, 199-213, 307-321, 352-366, 389-411, 397-411 or 140-200 of the full-length human TDP-43 having the sequence of SEQ ID NO:1. In another preferred embodiment of the invention, the binding molecules, in particular antibodies or antigen-binding fragments thereof, preferably specifically bind to peptides comprising, preferably consisting of, binding regions consisting of amino acids 183-188, 203-213, 204-208, 204-211, 205-210, 316-323, 358-361, 400-405, 400-406 or 400-412 of human TDP-43 (SEQ ID NO: 1). In some embodiments, the TDP-43 binding molecules, in particular antibodies or antigen-binding fragments thereof, bind within the C-terminal region of TDP-43. This may be advantageous, for example because C-terminal fragments of TDP-43 are found in the insoluble fraction and may therefore be pathologically relevant. More specifically, the TDP-43 binding molecules, in particular antibodies or antigen-binding fragments thereof, may bind to an epitope within amino acids residues 400-405, 400-406 or 400-412 of human TDP-43 (SEQ ID NO: 1). In some embodiments of the invention, the antibody is a monoclonal antibody. In some embodiments, the antibody is a murine, murinized, human, humanized, or chimeric antibody. It will be appreciated that equivalent binding regions exist in non-human TDP-43. Thus, for example, the mouse TDP-43 amino acid sequence (see Uniprot accession Q921F2) is also 414 amino acids in length and is 96% (398/414 residues) identical with the human sequence. The invention encompasses binding molecules, in particular antibodies or antigen-binding fragments thereof, that bind to equivalent regions/peptides to those specified above with reference to SEQ ID NO: 1 in non-human TDP-43, especially murine TDP-43.

In particular, the present invention is summarized in the following embodiments:

1. A TDP-43 binding molecule, which binds misfolded aggregated TDP-43 and non-aggregated physiological TDP-43, particularly human TDP-43.

2. The TDP-43 binding molecule of the preceding embodiment, which binds to an epitope within amino acids residues 181-195, 199-213, 307-321, 352-366, 389-411, 397-411 or 140-200, of human TDP-43 (SEQ ID NO: 1).

3. The TDP-43 binding molecule of the preceding embodiment, which binds to an epitope within amino acids residues 183-188, 203-213, 204-208, 204-211, 205-210, 316-323, 358-361, 400-405, 400-406 or 400-412 of human TDP-43 (SEQ ID NO: 1).

4. The binding molecule of any one of the preceding embodiments, which is an antibody or an antigen-binding fragment thereof.

5. The binding molecule of any one of the preceding embodiments, or a TDP-43 binding molecule, which comprises a) VH-CDR1 comprising the amino acid sequence of SEQ ID NO: 11; VH-CDR2 comprising the amino acid sequence of SEQ ID NO: 12; and VH-CDR3 comprising the amino acid sequence ES (Glu-Ser); VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17; or b) VH-CDR1 comprising the amino acid sequence of SEQ ID NO: 21; VH-CDR2 comprising the amino acid sequence of SEQ ID NO: 22; and VH-CDR3 comprising the amino acid sequence ES (Glu-Ser); VL-CDR1 comprising the amino acid sequence of SEQ ID NO: 25; VL-CDR2 comprising the amino acid sequence of SEQ ID NO: 16; and VL-CDR3 comprising the amino acid sequence of SEQ ID NO: 27; or c) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or d) VH-CDR1 comprising the amino acid sequence of SEQ ID NO: 41; VH-CDR2 comprising the amino acid sequence of SEQ ID NO: 42; and VH-CDR3 comprising the amino acid sequence of SEQ ID NO: 43; VL-CDR1 comprising the amino acid sequence of SEQ ID NO: 45; VL-CDR2 comprising the amino acid sequence of SEQ ID NO: 46; and VL-CDR3 comprising the amino acid sequence of SEQ ID NO: 47; or e) VH-CDR1 comprising the amino acid sequence of SEQ ID NO: 61; VH-CDR2 comprising the amino acid sequence of SEQ ID NO: 62; and VH-CDR3 comprising the amino acid sequence of SEQ ID NO: 63; VL-CDR1 comprising the amino acid sequence of SEQ ID NO: 65; VL-CDR2 comprising the amino acid sequence of SEQ ID NO: 66; and VL-CDR3 comprising the amino acid sequence of SEQ ID NO: 67; or f) VH-CDR1 comprising the amino acid sequence of SEQ ID NO: 71; VH-CDR2 comprising the amino acid sequence of SEQ ID NO: 72; and VH-CDR3 comprising the amino acid sequence 73; VL-CDR1 comprising the amino acid sequence of SEQ ID NO: 75; VL-CDR2 comprising the amino acid sequence of SEQ ID NO: 16; and VL-CDR3 comprising the amino acid sequence of SEQ ID NO: 77; or g) VH-CDR1 comprising the amino acid sequence of SEQ ID NO: 81; VH-CDR2 comprising the amino acid sequence of SEQ ID NO: 82; and VH-CDR3 comprising the amino acid sequence of SEQ ID NO: 83; VL-CDR1 comprising the amino acid sequence of SEQ ID NO: 85; VL-CDR2 comprising the amino acid sequence of SEQ ID NO: 86; and VL-CDR3 comprising the amino acid sequence of SEQ ID NO: 87; or h) VH-CDR1 comprising the amino acid sequence of SEQ ID NO: 101; VH-CDR2 comprising the amino acid sequence of SEQ ID NO: 102; and VH-CDR3 comprising the amino acid sequence of SEQ ID NO: 103; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or i) VH-CDR1 comprising the amino acid sequence of SEQ ID NO: 121; VH-CDR2 comprising the amino acid sequence of SEQ ID NO: 122; and VH-CDR3 comprising the amino acid sequence of SEQ ID NO: 123; VL-CDR1 comprising the amino acid sequence of SEQ ID NO: 125; VL-CDR2 comprising the amino acid sequence of SEQ ID NO: 16; and VL-CDR3 comprising the amino acid sequence of SEQ ID NO: 127; or j) VH-CDR1 comprising the amino acid sequence of SEQ ID NO: 141; VH-CDR2 comprising the amino acid sequence of SEQ ID NO: 142; and VH-CDR3 comprising the amino acid sequence of SEQ ID NO: 143; VL-CDR1 comprising the amino acid sequence of SEQ ID NO: 145; VL-CDR2 comprising the amino acid sequence of SEQ ID NO: 146; and VL-CDR3 comprising the amino acid sequence of SEQ ID NO: 147; or k) VH-CDR1 comprising the amino acid sequence of SEQ ID NO: 151; VH-CDR2 comprising the amino acid sequence of SEQ ID NO: 152; and VH-CDR3 comprising the amino acid sequence of SEQ ID NO: 153; VL-CDR1 comprising the amino acid sequence of SEQ ID NO: 155; VL-CDR2 comprising the amino acid sequence of SEQ ID NO: 156; and VL-CDR3 comprising the amino acid sequence of SEQ ID NO: 157.

6. The binding molecule of any one of the preceding embodiments, or a TDP-43 binding molecule, which is an antibody or an antigen-binding fragment thereof comprising a. a Heavy Chain Variable Region (VH) comprising the sequence of SEQ ID NO: 10 or a Heavy Chain Variable Region (VH) having at least 94%, 95%, 96%, 97%, 98% or 99% sequence identity to the amino acid sequence of SEQ ID NO: 10; and a Light Chain Variable Region (VL) comprising the sequence of SEQ ID NO: 14 or a Light Chain Variable Region (VL) having at least 96%, 97%, 98% or 99% sequence identity to the amino acid sequence of SEQ ID NO: 14; or b. a Heavy Chain Variable Region (VH) comprising the sequence of SEQ ID NO: 20 or a Heavy Chain Variable Region (VH) having at least 98% or 99% sequence identity to the amino acid sequence of SEQ ID NO: 20; and a Light Chain Variable Region (VL) comprising the sequence of SEQ ID NO: 24 or a Light Chain Variable Region (VL) having at least 97%, 98% or 99% sequence identity to the amino acid sequence of SEQ ID NO: 24; or c. a Heavy Chain Variable Region (VH) comprising the sequence of SEQ ID NO: 30 or a Heavy Chain Variable Region (VH) having at least 92%, 93%, 94%, 95%, 96%, 97%, 98%, or 99% sequence identity to the amino acid sequence of SEQ ID NO: 30; and a Light Chain Variable Region (VL) comprising the sequence of SEQ ID NO: 34 or a Light Chain Variable Region (VL) having at least 98% or 99% sequence identity to the amino acid sequence of SEQ ID NO: 34; or d. a Heavy Chain Variable Region (VH) comprising the sequence of SEQ ID NO: 40 or a Heavy Chain Variable Region (VH) having at least 90%, 91%, 92%, 93%, 94%, 95%, 96%, 97%, 98% or 99% sequence identity to the amino acid sequence of SEQ ID NO: 40; and a Light Chain Variable Region (VL) comprising the sequence of SEQ ID NO: 44; or e. a Heavy Chain Variable Region (VH) comprising the sequence of SEQ ID NO: 60 or a Heavy Chain Variable Region (VH) having at least 94%, 95%, 96%, 97%, 98% or 99% sequence identity to the amino acid sequence of SEQ ID NO: 60; and a Light Chain Variable Region (VL) comprising the sequence of SEQ ID NO: 64 or a Light Chain Variable Region (VL) having at least 99% sequence identity to the amino acid sequence of SEQ ID NO: 64; or f. a Heavy Chain Variable Region (VH) comprising the sequence of SEQ ID NO: 70 or a Heavy Chain Variable Region (VH) having at least 93%, 94%, 95%, 96%, 97%, 98% or 99% sequence identity to the amino acid sequence of SEQ ID NO: 70; and a Light Chain Variable Region (VL) comprising the sequence of SEQ ID NO: 74 or a Light Chain Variable Region (VL) having at least 99% sequence identity to the amino acid sequence of SEQ ID NO: 74; or g. a Heavy Chain Variable Region (VH) comprising the sequence of SEQ ID NO: 80 or a Heavy Chain Variable Region (VH) having at least 90%, 91%, 92%, 93%, 94%, 95%, 96%, 97%, 98% or 99% sequence identity to the amino acid sequence of SEQ ID NO: 80; and a Light Chain Variable Region (VL) comprising the sequence of SEQ ID NO: 84 or a Light Chain Variable Region (VL) having at least 96%, 97%, 98% or 99% sequence identity to the amino acid sequence of SEQ ID NO: 84; or h. a Heavy Chain Variable Region (VH) comprising the sequence of SEQ ID NO: 100 or a Heavy Chain Variable Region (VH) having at least 93%, 94%, 95%, 96%, 97%, 98%, or 99% sequence identity to the amino acid sequence of SEQ ID NO: 100; and a Light Chain Variable Region (VL) comprising the sequence of SEQ ID NO: 104 or a Light Chain Variable Region (VL) having at least 99% sequence identity to the amino acid sequence of SEQ ID NO: 104; or i. a Heavy Chain Variable Region (VH) comprising the sequence of SEQ ID NO: 120 or a Heavy Chain Variable Region (VH) having at least 89%, 90%, 91%, 92%, 93%, 94%, 95%, 96%, 97%, 98% or 99% sequence identity to the amino acid sequence of SEQ ID NO: 120; and a Light Chain Variable Region (VL) comprising the sequence of SEQ ID NO: 124 or a Light Chain Variable Region (VL) having at least 96%, 97%, 98% or 99% sequence identity to the amino acid sequence of SEQ ID NO: 124; or j. a Heavy Chain Variable Region (VH) comprising the sequence of SEQ ID NO: 140 or a Heavy Chain Variable Region (VH) having at least 93%, 94%, 95%, 96%, 97%, 98% or 99% sequence identity to the amino acid sequence of SEQ ID NO: 140; and a Light Chain Variable Region (VL) comprising the sequence of SEQ ID NO: 144; or k. a Heavy Chain Variable Region (VH) comprising the sequence of SEQ ID NO: 150 or a Heavy Chain Variable Region (VH) having at least 85%, 86%, 87%, 88%, 89%, 90%, 91%, 92%, 93%, 94%, 95%, 96%, 97%, 98% or 99% sequence identity to the amino acid sequence of SEQ ID NO: 150; and a Light Chain Variable Region (VL) comprising the sequence of SEQ ID NO: 154 or a Light Chain Variable Region (VL) having at least 99% sequence identity to the amino acid sequence of SEQ ID NO: 154.

7. The binding molecule of any one of the preceding embodiments, or a TDP-43 binding molecule, which is an antibody or an antigen-binding fragment thereof comprising:

a. a Heavy Chain Variable Region (VH) comprising the sequence of SEQ ID NO: 10 and a Light Chain Variable Region (VL) comprising the sequence of SEQ ID NO: 14; or c. a Heavy Chain Variable Region (VH) comprising the sequence of SEQ ID NO: 20 and a Light Chain Variable Region (VL) comprising the sequence of SEQ ID NO: 24; or d. a Heavy Chain Variable Region (VH) comprising the sequence of SEQ ID NO: 30 and a Light Chain Variable Region (VL) comprising the sequence of SEQ ID NO: 34; or e. a Heavy Chain Variable Region (VH) comprising the sequence of SEQ ID NO: 40 and a Light Chain Variable Region (VL) comprising the sequence of SEQ ID NO: 44; or f. a Heavy Chain Variable Region (VH) comprising the sequence of SEQ ID NO: 60 and a Light Chain Variable Region (VL) comprising the sequence of SEQ ID NO: 64; or g. a Heavy Chain Variable Region (VH) comprising the sequence of SEQ ID NO: 70 and a Light Chain Variable Region (VL) comprising the sequence of SEQ ID NO: 74; or h. a Heavy Chain Variable Region (VH) comprising the sequence of SEQ ID NO: 80 and a Light Chain Variable Region (VL) comprising the sequence of SEQ ID NO: 84; or i. a Heavy Chain Variable Region (VH) comprising the sequence of SEQ ID NO: 100 and a Light Chain Variable Region (VL) comprising the sequence of SEQ ID NO: 104; or j. a Heavy Chain Variable Region (VH) comprising the sequence of SEQ ID NO: 120 and a Light Chain Variable Region (VL) comprising the sequence of SEQ ID NO: 124; or k. a Heavy Chain Variable Region (VH) comprising the sequence of SEQ ID NO: 140 and a Light Chain Variable Region (VL) comprising the sequence of SEQ ID NO: 144; or l. a Heavy Chain Variable Region (VH) comprising the sequence of SEQ ID NO: 150 and a Light Chain Variable Region (VL) comprising the sequence of SEQ ID NO: 154.

In some embodiments, the antibody comprises:

a) VH-CDR1 comprising the amino acid sequence of SEQ ID NO: 11; VH-CDR2 comprising the amino acid sequence of SEQ ID NO: 12; and VH-CDR3 comprising the amino acid sequence ES (Glu-Ser); VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17; or b) VH-CDR1 comprising the amino acid sequence of SEQ ID NO: 21; VH-CDR2 comprising the amino acid sequence of SEQ ID NO: 22; and VH-CDR3 comprising the amino acid sequence ES (Glu-Ser); VL-CDR1 comprising the amino acid sequence of SEQ ID NO: 25; VL-CDR2 comprising the amino acid sequence of SEQ ID NO: 16; and VL-CDR3 comprising the amino acid sequence of SEQ ID NO: 27; or c) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or d) VH-CDR1 comprising the amino acid sequence of SEQ ID NO: 41; VH-CDR2 comprising the amino acid sequence of SEQ ID NO: 42; and VH-CDR3 comprising the amino acid sequence of SEQ ID NO: 43; VL-CDR1 comprising the amino acid sequence of SEQ ID NO: 45; VL-CDR2 comprising the amino acid sequence of SEQ ID NO: 46; and VL-CDR3 comprising the amino acid sequence of SEQ ID NO: 47; or e) VH-CDR1 comprising the amino acid sequence of SEQ ID NO: 61; VH-CDR2 comprising the amino acid sequence of SEQ ID NO: 62; and VH-CDR3 comprising the amino acid sequence of SEQ ID NO: 63; VL-CDR1 comprising the amino acid sequence of SEQ ID NO: 65; VL-CDR2 comprising the amino acid sequence of SEQ ID NO: 66; and VL-CDR3 comprising the amino acid sequence of SEQ ID NO: 67; or f) VH-CDR1 comprising the amino acid sequence of SEQ ID NO: 71; VH-CDR2 comprising the amino acid sequence of SEQ ID NO: 72; and VH-CDR3 comprising the amino acid sequence of SEQ ID NO: 73; VL-CDR1 comprising the amino acid sequence of SEQ ID NO: 75; VL-CDR2 comprising the amino acid sequence of SEQ ID NO: 16; and VL-CDR3 comprising the amino acid sequence of SEQ ID NO: 77; or g) VH-CDR1 comprising the amino acid sequence of SEQ ID NO: 81; VH-CDR2 comprising the amino acid sequence of SEQ ID NO: 82; and VH-CDR3 comprising the amino acid sequence of SEQ ID NO: 83; VL-CDR1 comprising the amino acid sequence of SEQ ID NO: 85; VL-CDR2 comprising the amino acid sequence of SEQ ID NO: 86; and VL-CDR3 comprising the amino acid sequence of SEQ ID NO: 87; or h) VH-CDR1 comprising the amino acid sequence of SEQ ID NO: 101; VH-CDR2 comprising the amino acid sequence of SEQ ID NO: 102; and VH-CDR3 comprising the amino acid sequence of SEQ ID NO: 103; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or i) VH-CDR1 comprising the amino acid sequence of SEQ ID NO: 121; VH-CDR2 comprising the amino acid sequence of SEQ ID NO: 122; and VH-CDR3 comprising the amino acid sequence of SEQ ID NO: 123; VL-CDR1 comprising the amino acid sequence of SEQ ID NO: 125; VL-CDR2 comprising the amino acid sequence of SEQ ID NO: 16; and VL-CDR3 comprising the amino acid sequence of SEQ ID NO: 127; or j) VH-CDR1 comprising the amino acid sequence of SEQ ID NO: 141; VH-CDR2 comprising the amino acid sequence of SEQ ID NO: 142; and VH-CDR3 comprising the amino acid sequence of SEQ ID NO: 143; VL-CDR1 comprising the amino acid sequence of SEQ ID NO: 145; VL-CDR2 comprising the amino acid sequence of SEQ ID NO: 146; and VL-CDR3 comprising the amino acid sequence of SEQ ID NO: 147; or k) VH-CDR1 comprising the amino acid sequence of SEQ ID NO: 151; VH-CDR2 comprising the amino acid sequence of SEQ ID NO: 152; and VH-CDR3 comprising the amino acid sequence of SEQ ID NO: 153; VL-CDR1 comprising the amino acid sequence of SEQ ID NO: 155; VL-CDR2 comprising the amino acid sequence of SEQ ID NO: 156; and VL-CDR3 comprising the amino acid sequence of SEQ ID NO: 157.

In some embodiments, the antibody comprises:

a) VH-CDR1 comprising the amino acid sequence of SEQ ID NO: 11; VH-CDR2 comprising the amino acid sequence of SEQ ID NO: 12; and VH-CDR3 comprising the amino acid sequence ES (Glu-Ser); or b) VH-CDR1 comprising the amino acid sequence of SEQ ID NO: 21; VH-CDR2 comprising the amino acid sequence of SEQ ID NO: 22; and VH-CDR3 comprising the amino acid sequence ES (Glu-Ser); or c) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; or d) VH-CDR1 comprising the amino acid sequence of SEQ ID NO: 41; VH-CDR2 comprising the amino acid sequence of SEQ ID NO: 42; and VH-CDR3 comprising the amino acid sequence of SEQ ID NO: 43; or e) VH-CDR1 comprising the amino acid sequence of SEQ ID NO: 61; VH-CDR2 comprising the amino acid sequence of SEQ ID NO: 62; and VH-CDR3 comprising the amino acid sequence of SEQ ID NO: 63; or f) VH-CDR1 comprising the amino acid sequence of SEQ ID NO: 71; VH-CDR2 comprising the amino acid sequence of SEQ ID NO: 72; and VH-CDR3 comprising the amino acid sequence of SEQ ID NO: 73; or g) VH-CDR1 comprising the amino acid sequence of SEQ ID NO: 81; VH-CDR2 comprising the amino acid sequence of SEQ ID NO: 82; and VH-CDR3 comprising the amino acid sequence of SEQ ID NO: 83; or h) VH-CDR1 comprising the amino acid sequence of SEQ ID NO: 101; VH-CDR2 comprising the amino acid sequence of SEQ ID NO: 102; and VH-CDR3 comprising the amino acid sequence of SEQ ID NO: 103; or i) VH-CDR1 comprising the amino acid sequence of SEQ ID NO: 121; VH-CDR2 comprising the amino acid sequence of SEQ ID NO: 122; and VH-CDR3 comprising the amino acid sequence of SEQ ID NO: 123; or j) VH-CDR1 comprising the amino acid sequence of SEQ ID NO: 141; VH-CDR2 comprising the amino acid sequence of SEQ ID NO: 142; and VH-CDR3 comprising the amino acid sequence of SEQ ID NO: 143; or k) VH-CDR1 comprising the amino acid sequence of SEQ ID NO: 151; VH-CDR2 comprising the amino acid sequence of SEQ ID NO: 152; and VH-CDR3 comprising the amino acid sequence of SEQ ID NO: 153.

In some embodiments, the antibody comprises:

a) VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17; or b) VL-CDR1 comprising the amino acid sequence of SEQ ID NO: 25; VL-CDR2 comprising the amino acid sequence of SEQ ID NO: 16; and VL-CDR3 comprising the amino acid sequence of SEQ ID NO: 27; or c) VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or d) VL-CDR1 comprising the amino acid sequence of SEQ ID NO: 65; VL-CDR2 comprising the amino acid sequence of SEQ ID NO: 66; and VL-CDR3 comprising the amino acid sequence of SEQ ID NO: 67; or e) VL-CDR1 comprising the amino acid sequence of SEQ ID NO: 75; VL-CDR2 comprising the amino acid sequence of SEQ ID NO: 16; and VL-CDR3 comprising the amino acid sequence of SEQ ID NO: 77; or f) VL-CDR1 comprising the amino acid sequence of SEQ ID NO: 85; VL-CDR2 comprising the amino acid sequence of SEQ ID NO: 86; and VL-CDR3 comprising the amino acid sequence of SEQ ID NO: 87; or g) VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or h) VL-CDR1 comprising the amino acid sequence of SEQ ID NO: 125; VL-CDR2 comprising the amino acid sequence of SEQ ID NO: 16; and VL-CDR3 comprising the amino acid sequence of SEQ ID NO: 127; or i) VL-CDR1 comprising the amino acid sequence of SEQ ID NO: 155; VL-CDR2 comprising the amino acid sequence of SEQ ID NO: 156; and VL-CDR3 comprising the amino acid sequence of SEQ ID NO: 157.

In some embodiments, the antibody comprises:

a) VH-CDR1 comprising an amino acid sequence having at least 80%, 90%, 95% or 100% sequence identity to SEQ ID NO: 11; a VH-CDR2 comprising an amino acid sequence having at least 80%, 90%, 95% or 100% sequence identity to SEQ ID NO: 12; a VH-CDR3 comprising an amino acid sequence ES (Glu-Ser); a VL-CDR1 comprising the amino acid sequence of SEQ ID NO: 15; a VL-CDR2 comprising the amino acid sequence of SEQ ID NO: 16; and a VL-CDR3 comprising the amino acid sequence of SEQ ID NO: 17; or b) VH-CDR1 comprising an amino acid sequence having at least 80%, 90%, 95% or 100% sequence identity to SEQ ID NO: 21; a VH-CDR2 comprising an amino acid sequence having at least 80%, 90%, 95% or 100% sequence identity to SEQ ID NO: 22; a VH-CDR3 comprising an amino acid sequence ES (Glu-Ser); a VL-CDR1 comprising the amino acid sequence of SEQ ID NO: 25; a VL-CDR2 comprising the amino acid sequence of SEQ ID NO: 16; and a VL-CDR3 comprising the amino acid sequence of SEQ ID NO: 27; or c) VH-CDR1 comprising an amino acid sequence having at least 80%, 90%, 95% or 100% sequence identity to SEQ ID NO: 31; a VH-CDR2 comprising an amino acid sequence having at least 80%, 90%, 95% or 100% sequence identity to SEQ ID NO: 32; a VH-CDR3 comprising an amino acid sequence having at least 80%, 90%, 95% or 100% sequence identity to SEQ ID NO: 33; a VL-CDR1 comprising the amino acid sequence of SEQ ID NO: 35; a VL-CDR2 comprising the amino acid sequence of SEQ ID NO: 36; and a VL-CDR3 comprising the amino acid sequence of SEQ ID NO: 37; or d) VH-CDR1 comprising an amino acid sequence having at least 80%, 90%, 95% or 100% sequence identity to SEQ ID NO: 41; a VH-CDR2 comprising an amino acid sequence having at least 80%, 90%, 95% or 100% sequence identity to SEQ ID NO: 42; a VH-CDR3 comprising an amino acid sequence having at least 80%, 90%, 95% or 100% sequence identity to SEQ ID NO: 43; a VL-CDR1 comprising the amino acid sequence of SEQ ID NO: 45; a VL-CDR2 comprising the amino acid sequence of SEQ ID NO: 46; and a VL-CDR3 comprising the amino acid sequence of SEQ ID NO: 47; or e) VH-CDR1 comprising an amino acid sequence having at least 80%, 90%, 95% or 100% sequence identity to SEQ ID NO: 61; a VH-CDR2 comprising an amino acid sequence having at least 80%, 90%, 95% or 100% sequence identity to SEQ ID NO: 62; a VH-CDR3 comprising an amino acid sequence having at least 80%, 90%, 95% or 100% sequence identity to SEQ ID NO: 63; a VL-CDR1 comprising the amino acid sequence of SEQ ID NO: 65; a VL-CDR2 comprising the amino acid sequence of SEQ ID NO: 66; and a VL-CDR3 comprising the amino acid sequence of SEQ ID NO: 67; or f) VH-CDR1 comprising an amino acid sequence having at least 80%, 90%, 95% or 100% sequence identity to SEQ ID NO: 71; a VH-CDR2 comprising an amino acid sequence having at least 80%, 90%, 95% or 100% sequence identity to SEQ ID NO: 72; a VH-CDR3 comprising an amino acid sequence having at least 80%, 90%, 95% or 100% sequence identity to SEQ ID NO: 73; a VL-CDR1 comprising the amino acid sequence of SEQ ID NO: 75; a VL-CDR2 comprising the amino acid sequence of SEQ ID NO: 16; and a VL-CDR3 comprising the amino acid sequence of SEQ ID NO: 77; or g) VH-CDR1 comprising an amino acid sequence having at least 80%, 90%, 95% or 100% sequence identity to SEQ ID NO: 81; a VH-CDR2 comprising an amino acid sequence having at least 80%, 90%, 95% or 100% sequence identity to SEQ ID NO: 82; a VH-CDR3 comprising an amino acid sequence having at least 80%, 90%, 95% or 100% sequence identity to SEQ ID NO: 83; a VL-CDR1 comprising the amino acid sequence of SEQ ID NO: 85; a VL-CDR2 comprising the amino acid sequence of SEQ ID NO: 86; and a VL-CDR3 comprising the amino acid sequence of SEQ ID NO: 87; or h) VH-CDR1 comprising an amino acid sequence having at least 80%, 90%, 95% or 100% sequence identity to SEQ ID NO: 101; a VH-CDR2 comprising an amino acid sequence having at least 80%, 90%, 95% or 100% sequence identity to SEQ ID NO: 102; a VH-CDR3 comprising an amino acid sequence having at least 80%, 90%, 95% or 100% sequence identity to SEQ ID NO: 103; a VL-CDR1 comprising the amino acid sequence of SEQ ID NO: 105; a VL-CDR2 comprising the amino acid sequence of SEQ ID NO: 106; and a VL-CDR3 comprising the amino acid sequence of SEQ ID NO: 107; or i) VH-CDR1 comprising an amino acid sequence having at least 80%, 90%, 95% or 100% sequence identity to SEQ ID NO: 121; a VH-CDR2 comprising an amino acid sequence having at least 80%, 90%, 95% or 100% sequence identity to SEQ ID NO: 122; a VH-CDR3 comprising an amino acid sequence having at least 80%, 90%, 95% or 100% sequence identity to SEQ ID NO: 123; a VL-CDR1 comprising the amino acid sequence of SEQ ID NO: 125; a VL-CDR2 comprising the amino acid sequence of SEQ ID NO: 16; and a VL-CDR3 comprising the amino acid sequence of SEQ ID NO: 127; or j) VH-CDR1 comprising an amino acid sequence having at least 80%, 90%, 95% or 100% sequence identity to SEQ ID NO: 141; a VH-CDR2 comprising an amino acid sequence having at least 80%, 90%, 95% or 100% sequence identity to SEQ ID NO: 142; a VH-CDR3 comprising an amino acid sequence having at least 80%, 90%, 95% or 100% sequence identity to SEQ ID NO: 143; a VL-CDR1 comprising the amino acid sequence of SEQ ID NO: 145; a VL-CDR2 comprising the amino acid sequence of SEQ ID NO: 146; and a VL-CDR3 comprising the amino acid sequence of SEQ ID NO: 147; or k) VH-CDR1 comprising an amino acid sequence having at least 80%, 90%, 95% or 100% sequence identity to SEQ ID NO: 151; a VH-CDR2 comprising an amino acid sequence having at least 80%, 90%, 95% or 100% sequence identity to SEQ ID NO: 152; a VH-CDR3 comprising an amino acid sequence having at least 80%, 90%, 95% or 100% sequence identity to SEQ ID NO: 153; a VL-CDR1 comprising the amino acid sequence of SEQ ID NO: 155; a VL-CDR2 comprising the amino acid sequence of SEQ ID NO: 156; and a VL-CDR3 comprising the amino acid sequence of SEQ ID NO: 157; or In some embodiments, the antibody comprises:

a) VH-CDR1 comprising the amino acid sequence of SEQ ID NO: 11; a VH-CDR2 comprising the amino acid sequence of SEQ ID NO: 12; a VH-CDR3 comprising the amino acid sequence ES (Glu-Ser); a VL-CDR1 comprising an amino acid sequence having at least 80%, 90%, 95% or 100% sequence identity to SEQ ID NO: 15; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 17; or b) VH-CDR1 comprising the amino acid sequence of SEQ ID NO: 21; a VH-CDR2 comprising the amino acid sequence of SEQ ID NO: 22; a VH-CDR3 comprising the amino acid sequence ES (Glu-Ser); a VL-CDR1 comprising an amino acid sequence having at least 80%, 90%, 95% or 100% sequence identity to SEQ ID NO: 25; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 27; or c) VH-CDR1 comprising the amino acid sequence of SEQ ID NO: 31; a VH-CDR2 comprising the amino acid sequence of SEQ ID NO: 32; a VH-CDR3 comprising the amino acid sequence of SEQ ID NO: 33; a VL-CDR1 comprising an amino acid sequence having at least 80%, 90%, 95% or 100% sequence identity to SEQ ID NO: 35; a VL-CDR2 comprising an amino acid sequence having at least 80%, 90%, 95% or 100% sequence identity to SEQ ID NO: 36; and a VL-CDR3 comprising an amino acid sequence having at least 80%, 90%, 95% or 100% sequence identity to SEQ ID NO: 37; or d) VH-CDR1 comprising the amino acid sequence of SEQ ID NO: 41; a VH-CDR2 comprising the amino acid sequence of SEQ ID NO: 42; a VH-CDR3 comprising the amino acid sequence of SEQ ID NO: 43; a VL-CDR1 comprising an amino acid sequence having at least 80%, 90%, 95% or 100% sequence identity to SEQ ID NO: 45; a VL-CDR2 comprising an amino acid sequence having at least 80%, 90%, 95% or 100% sequence identity to SEQ ID NO: 46; and a VL-CDR3 comprising an amino acid sequence having at least 80%, 90%, 95% or 100% sequence identity to SEQ ID NO: 47; or e) VH-CDR1 comprising the amino acid sequence of SEQ ID NO: 61; a VH-CDR2 comprising the amino acid sequence of SEQ ID NO: 62; a VH-CDR3 comprising the amino acid sequence of SEQ ID NO: 63; a VL-CDR1 comprising an amino acid sequence having at least 80%, 90%, 95% or 100% sequence identity to SEQ ID NO: 65; a VL-CDR2 comprising an amino acid sequence having at least 80%, 90%, 95% or 100% sequence identity to SEQ ID NO: 66; and a VL-CDR3 comprising an amino acid sequence having at least 80%, 90%, 95% or 100% sequence identity to SEQ ID NO: 67; or f) VH-CDR1 comprising the amino acid sequence of SEQ ID NO: 71; a VH-CDR2 comprising the amino acid sequence of SEQ ID NO: 72; a VH-CDR3 comprising the amino acid sequence of SEQ ID NO: 73; a VL-CDR1 comprising an amino acid sequence having at least 80%, 90%, 95% or 100% sequence identity to SEQ ID NO: 75; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 77; or g) VH-CDR1 comprising the amino acid sequence of SEQ ID NO: 81; a VH-CDR2 comprising the amino acid sequence of SEQ ID NO: 82; a VH-CDR3 comprising the amino acid sequence of SEQ ID NO: 83; a VL-CDR1 comprising an amino acid sequence having at least 80%, 90%, 95% or 100% sequence identity to SEQ ID NO: 85; a VL-CDR2 comprising an amino acid sequence having at least 80%, 90%, 95% or 100% sequence identity to SEQ ID NO: 86; and a VL-CDR3 comprising an amino acid sequence having at least 80%, 90%, 95% or 100% sequence identity to SEQ ID NO: 87; or h) VH-CDR1 comprising the amino acid sequence of SEQ ID NO: 101; a VH-CDR2 comprising the amino acid sequence of SEQ ID NO: 102; a VH-CDR3 comprising the amino acid sequence of SEQ ID NO: 103; a VL-CDR1 comprising an amino acid sequence having at least 80%, 90%, 95% or 100% sequence identity to SEQ ID NO: 105; a VL-CDR2 comprising an amino acid sequence having at least 80%, 90%, 95% or 100% sequence identity to SEQ ID NO: 106; and a VL-CDR3 comprising an amino acid sequence having at least 80%, 90%, 95% or 100% sequence identity to SEQ ID NO: 107; or i) VH-CDR1 comprising the amino acid sequence of SEQ ID NO: 121; a VH-CDR2 comprising the amino acid sequence of SEQ ID NO: 122; a VH-CDR3 comprising the amino acid sequence of SEQ ID NO: 123; a VL-CDR1 comprising an amino acid sequence having at least 80%, 90%, 95% or 100% sequence identity to SEQ ID NO: 125; a VL-CDR2 comprising an amino acid sequence having at least 80%, 90%, 95% or 100% sequence identity to SEQ ID NO: 16; and a VL-CDR3 comprising an amino acid sequence having at least 80%, 90%, 95% or 100% sequence identity to SEQ ID NO: 127; or j) VH-CDR1 comprising the amino acid sequence of SEQ ID NO: 141; a VH-CDR2 comprising the amino acid sequence of SEQ ID NO: 142; a VH-CDR3 comprising the amino acid sequence of SEQ ID NO: 143; a VL-CDR1 comprising an amino acid sequence having at least 80%, 90%, 95% or 100% sequence identity to SEQ ID NO: 145; a VL-CDR2 comprising an amino acid sequence having at least 80%, 90%, 95% or 100% sequence identity to SEQ ID NO: 146; and a VL-CDR3 comprising an amino acid sequence having at least 80%, 90%, 95% or 100% sequence identity to SEQ ID NO: 147; or k) VH-CDR1 comprising the amino acid sequence of SEQ ID NO: 151; a VH-CDR2 comprising the amino acid sequence of SEQ ID NO: 152; a VH-CDR3 comprising the amino acid sequence of SEQ ID NO: 153; a VL-CDR1 comprising an amino acid sequence having at least 80%, 90%, 95% or 100% sequence identity to SEQ ID NO: 155; a VL-CDR2 comprising an amino acid sequence having at least 80%, 90%, 95% or 100% sequence identity to SEQ ID NO: 156; and a VL-CDR3 comprising an amino acid sequence having at least 80%, 90%, 95% or 100% sequence identity to SEQ ID NO: 157.

In some embodiments, a TDP-43 antibody comprises at least one, two, three, four, five, or six CDRs selected from (a) VH-CDR1 comprising the amino acid sequence of SEQ ID NO: 11; (b) VH-CDR2 comprising the amino acid sequence of SEQ ID NO: 12; (c) VH-CDR3 comprising the amino acid sequence ES (Glu-Ser); (d) VL-CDR1 comprising the amino acid sequence of SEQ ID NO: 15; (e) VL-CDR2 comprising the amino acid sequence of SEQ ID NO: 16; and (f) VL-CDR3 comprising the amino acid sequence of SEQ ID NO: 17.

In some embodiments, a TDP-43 antibody comprises at least one, two, three, four, five, or six CDRs selected from (a) VH-CDR1 comprising the amino acid sequence of SEQ ID NO: 21; (b) VH-CDR2 comprising the amino acid sequence of SEQ ID NO: 22; (c) VH-CDR3 comprising the amino acid sequence ES (Glu-Ser); (d) VL-CDR1 comprising the amino acid sequence of SEQ ID NO: 25; (e) VL-CDR2 comprising the amino acid sequence of SEQ ID NO: 16; and (f) VL-CDR3 comprising the amino acid sequence of SEQ ID NO: 27.

In some embodiments, a TDP-43 antibody comprises at least one, two, three, four, five, or six CDRs selected from (a) VH-CDR1 comprising the amino acid sequence of SEQ ID NO: 31; (b) VH-CDR2 comprising the amino acid sequence of SEQ ID NO: 32; (c) VH-CDR3 comprising the amino acid sequence of SEQ ID NO: 33; (d) VL-CDR1 comprising the amino acid sequence of SEQ ID NO: 35; (e) VL-CDR2 comprising the amino acid sequence of SEQ ID NO: 36; and (f) VL-CDR3 comprising the amino acid sequence of SEQ ID NO: 37.

In some embodiments, a TDP-43 antibody comprises at least one, two, three CDRs selected from (a) VH-CDR1 comprising the amino acid sequence of SEQ ID NO: 41; (b) VH-CDR2 comprising the amino acid sequence of SEQ ID NO: 42; (c) VH-CDR3 comprising the amino acid sequence of SEQ ID NO: 43.

In some embodiments, a TDP-43 antibody comprises at least four, five, or six CDRs selected from (a) VH-CDR1 comprising the amino acid sequence of SEQ ID NO: 41; (b) VH-CDR2 comprising the amino acid sequence of SEQ ID NO: 42; (c) VH-CDR3 comprising the amino acid sequence of SEQ ID NO: 43; (d) VL-CDR1 comprising the amino acid sequence of SEQ ID NO: 45; (e) VL-CDR2 comprising the amino acid sequence of SEQ ID NO: 46; and (f) VL-CDR3 comprising the amino acid sequence of SEQ ID NO: 47.

In some embodiments, a TDP-43 antibody comprises at least one, two, three, four, five, or six CDRs selected from (a) VH-CDR1 comprising the amino acid sequence of SEQ ID NO: 61; (b) VH-CDR2 comprising the amino acid sequence of SEQ ID NO: 62; (c) VH-CDR3 comprising the amino acid sequence of SEQ ID NO: 63; (d) VL-CDR1 comprising the amino acid sequence of SEQ ID NO: 65; (e) VL-CDR2 comprising the amino acid sequence of SEQ ID NO: 66; and (f) VL-CDR3 comprising the amino acid sequence of SEQ ID NO: 67.

In some embodiments, a TDP-43 antibody comprises at least one, two, three, four, five, or six CDRs selected from (a) VH-CDR1 comprising the amino acid sequence of SEQ ID NO: 71; (b) VH-CDR2 comprising the amino acid sequence of SEQ ID NO: 72; (c) VH-CDR3 comprising the amino acid sequence of SEQ ID NO: 73; (d) VL-CDR1 comprising the amino acid sequence of SEQ ID NO: 75; (e) VL-CDR2 comprising the amino acid sequence of SEQ ID NO: 16; and (f) VL-CDR3 comprising the amino acid sequence of SEQ ID NO: 77.

In some embodiments, a TDP-43 antibody comprises at least one, two, three, four, five, or six CDRs selected from (a) VH-CDR1 comprising the amino acid sequence of SEQ ID NO: 81; (b) VH-CDR2 comprising the amino acid sequence of SEQ ID NO: 82; (c) VH-CDR3 comprising the amino acid sequence of SEQ ID NO: 83; (d) VL-CDR1 comprising the amino acid sequence of SEQ ID NO: 85; (e) VL-CDR2 comprising the amino acid sequence of SEQ ID NO: 86; and (f) VL-CDR3 comprising the amino acid sequence of SEQ ID NO: 87.

In some embodiments, a TDP-43 antibody comprises at least one, two, three, four, five, or six CDRs selected from (a) VH-CDR1 comprising the amino acid sequence of SEQ ID NO: 101; (b) VH-CDR2 comprising the amino acid sequence of SEQ ID NO: 102; (c) VH-CDR3 comprising the amino acid sequence of SEQ ID NO: 103; (d) VL-CDR1 comprising the amino acid sequence of SEQ ID NO: 105; (e) VL-CDR2 comprising the amino acid sequence of SEQ ID NO: 106; and (f) VL-CDR3 comprising the amino acid sequence of SEQ ID NO: 107.

In some embodiments, a TDP-43 antibody comprises at least one, two, three, four, five, or six CDRs selected from (a) VH-CDR1 comprising the amino acid sequence of SEQ ID NO: 121; (b) VH-CDR2 comprising the amino acid sequence of SEQ ID NO: 122; (c) VH-CDR3 comprising the amino acid sequence of SEQ ID NO: 123; (d) VL-CDR1 comprising the amino acid sequence of SEQ ID NO: 125; (e) VL-CDR2 comprising the amino acid sequence of SEQ ID NO: 16; and (f) VL-CDR3 comprising the amino acid sequence of SEQ ID NO: 127.

In some embodiments, a TDP-43 antibody comprises at least one, two, or three CDRs selected from (a) VH-CDR1 comprising the amino acid sequence of SEQ ID NO: 141; (b) VH-CDR2 comprising the amino acid sequence of SEQ ID NO: 142; (c) VH-CDR3 comprising the amino acid sequence of SEQ ID NO: 143.

In some embodiments, a TDP-43 antibody comprises at least four, five, or six CDRs selected from (a) VH-CDR1 comprising the amino acid sequence of SEQ ID NO: 141; (b) VH-CDR2 comprising the amino acid sequence of SEQ ID NO: 142; (c) VH-CDR3 comprising the amino acid sequence of SEQ ID NO: 143; (d) VL-CDR1 comprising the amino acid sequence of SEQ ID NO: 145; (e) VL-CDR2 comprising the amino acid sequence of SEQ ID NO: 146; and (f) VL-CDR3 comprising the amino acid sequence of SEQ ID NO: 147.

In some embodiments, a TDP-43 antibody comprises at least one, two, three, four, five, or six CDRs selected from (a) VH-CDR1 comprising the amino acid sequence of SEQ ID NO: 151; (b) VH-CDR2 comprising the amino acid sequence of SEQ ID NO: 152; (c) VH-CDR3 comprising the amino acid sequence of SEQ ID NO: 153; (d) VL-CDR1 comprising the amino acid sequence of SEQ ID NO: 155; (e) VL-CDR2 comprising the amino acid sequence of SEQ ID NO: 156; and (f) VL-CDR3 comprising the amino acid sequence of SEQ ID NO: 157.

In another embodiment, the TDP-43 antibody comprises a Heavy Chain Variable Domain (VH) selected from SEQ ID NO: 10, 20, 30, 40, 60, 70, 80, 100, 120, 140, 150 including post-translational modifications of that sequence. In a particular embodiment, the Heavy Chain Variable Domain (VH) comprises at least one, two, or three CDRs selected from (a) VH-CDR1 comprising the amino acid sequence selected from SEQ ID NO: 11, 21, 31, 41, 61, 71, 81, 101, 121, 141, 151, (b) VH-CDR2 comprising the amino acid sequence selected from SEQ ID NO: 12, 22, 32, 42, 62, 72, 82, 102, 122, 142, 152 (c) VH-CDR3 comprising the amino acid sequence selected from SEQ ID NO: 33, 43, 63, 73, 89, 103, 123, 143, 153, and ES (Glu-Ser).

In another embodiment, the TDP-43 antibody comprises a Light Chain Variable Domain (VL) selected from SEQ ID NO: 14, 24, 34, 64, 74, 84, 104, 124, 154 including post-translational modifications of that sequence. In a particular embodiment, the Light Chain Variable Domain (VL) comprises at least one, two, or three CDRs selected from (a) VL-CDR1 comprising the amino acid sequence selected from SEQ ID NO: 15, 25, 35, 65, 75, 85, 105, 125, 155 and (b) VL-CDR2 comprising the amino acid sequence selected from SEQ ID NO: 16, 36, 66, 86, 106, 156, (c) VL-CDR3 comprising the amino acid sequence selected from SEQ ID NO: 17, 27, 37, 67, 77, 87, 107, 127, 157, and ES (Glu-Ser).

In some embodiments, a TDP-43 antibody comprises at least one, two, or three CDRs selected from (a) VH-CDR1 comprising the amino acid sequence selected from SEQ ID NO: 11, 21, 31, 41, 61, 71, 81, 101, 111, 121, 141, 151, (b) VH-CDR2 comprising the amino acid sequence selected from SEQ ID NO: 12, 22, 32, 42, 62, 72, 82, 102, 122, 142, 152 (c) VH-CDR3 comprising the amino acid sequence selected from SEQ ID NO: 33, 43, 63, 73, 83, 103, 123, 143, 153, and ES (Glu-Ser).

In some embodiments, a TDP-43 antibody comprises at least one, two, or three CDRs selected from (a) VL-CDR1 comprising the amino acid sequence selected from SEQ ID NO: 15, 25, 35, 65, 75, 85, 105, 125, 155 (b) VL-CDR2 comprising the amino acid sequence selected from SEQ ID NO: 16, 36, 66, 86, 106, 156, (c) VL-CDR3 comprising the amino acid sequence selected from SEQ ID NO: 17, 27, 37, 67, 77, 87, 107, 127, 157.

In some embodiments, the Light Chain Variable Domain (VL) comprises at least one, two, or three CDRs selected from (a) VL-CDR1 comprising the amino acid sequence selected from SEQ ID NO: 15, 25, 35, 45, 65, 75, 85, 105, 125, 145, 155 and (b) VL-CDR2 comprising the amino acid sequence selected from SEQ ID NO: 16, 36, 66, 86, 106, 156, (c) VL-CDR3 comprising the amino acid sequence selected from SEQ ID NO: 17, 27, 37, 67, 77, 87, 107, 127, 157.

In some embodiments, the invention relates to an antibody derived from hybridoma clones 631B2A2, 633B12C8, 634H10H7, 636E5B8, 641H1E7, 642A10B11, 642D12B4, 646B7F7, 712A6B10, 809D9C2 or 809F12D8.

In some embodiments, the invention relates to an antibody selected from ACI-7069-631B2-Ab1, ACI-7069-633B12-Ab1, ACI-7069-634H10-Ab2, ACI-7069-636E5-Ab1, ACI-7069-641H1-Ab2, ACI-7069-642A10-Ab1, ACI-7069-642D12-Ab1, ACI-7069-646B7-Ab1, ACI-7071-712A6-Ab1, ACI-7071-809D9-Ab2 and ACI-7071-809F12-Ab1.

In certain embodiments, a binding molecule or an antibody provided herein has a dissociation constant (KD) of $\leq 1$ μM, $\leq 100$ nM, $\leq 10$ nM, $\leq 1$ nM, 0.1 nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M), in particular with respect to binding TDP-43, in particular soluble TDP-43, aggregated TDP-43 and/or oligomeric TDP-43. In some embodiments, TDP-43 binding molecules of the invention, in particular the antibodies or antigen-binding fragments thereof, may have a lower KD for aggregated TDP-43 than for soluble TDP-43. For example, the TDP-43 binding molecules of the invention may have a KD for aggregated TDP-43 of 30 nM or less, in specific embodiments 1 nM or less, and a KD for soluble TDP-43 of 500 nM or less. This is demonstrated for TDP-43 binding molecules of the invention in Example 8A with reference to Table 8.

In one embodiment, binding affinity to soluble or aggregated FL TDP-43 may be evaluated by determining the dissociation constants (KD) using surface plasmon resonance (SPR; Biacore T200, GE Healthcare Life Sciences). Reference may be made to Examples 8A and 8B for a detailed description of suitable SPR methods that may be employed.

TDP-43 binding molecules of the invention, in particular the antibodies or antigen-binding fragments thereof, typically bind TDP-43 with high affinity. For example, they may demonstrate an EC50 value of 200 pM or less, more preferably 20 pM or less and even more preferably 10 pM or less as determined by Luminex Assay. Reference may be made to example 3 for further details of a suitable assay. Similarly, they may demonstrate an EC50 value of 1600 ng/ml or less, more preferably 120 ng/ml or less and even more preferably 60 ng/ml or less as determined by an indirect ELISA. Reference may be made to example 4 for further details of a suitable assay.

The TDP-43 binding molecules of the invention, in particular the antibodies or antigen-binding fragments thereof, bind to both non-aggregated physiological TDP-43 and aggregated TDP-43. Thus, TDP-43 binding molecules of the invention, in particular the antibodies or antigen-binding fragments thereof, may bind approximately equally well to soluble and aggregated TDP-43. TDP-43 binding molecules of the invention, in particular the antibodies or antigen-binding fragments thereof, may bind approximately equally to aggregated TDP-43 as compared with non-aggregated TDP-43. More particularly, TDP-43 binding molecules of the invention, in particular the antibodies or antigen-binding fragments thereof, may bind approximately equally to aggregated TDP-43 in the cytoplasm as compared with non-aggregated TDP-43 in the nucleus. In other embodiments, TDP-43 binding molecules of the invention, in particular the antibodies or antigen-binding fragments thereof, may preferentially bind to aggregated TDP-43 as compared with non-aggregated TDP-43, whilst binding to both species. More particularly, TDP-43 binding molecules of the invention, in particular the antibodies or antigen-binding fragments thereof, may preferentially bind to aggregated TDP-43 in the cytoplasm as compared with non-aggregated TDP-43 in the nucleus, whilst binding to both species. Alternatively, in other embodiments, TDP-43 binding molecules of the invention, in particular the antibodies or antigen-binding fragments thereof, may preferentially bind to non-aggregated TDP-43 as compared with aggregated TDP-43, whilst binding to both species. More particularly, TDP-43 binding molecules of the invention, in particular the antibodies or antigen-binding fragments thereof, may preferentially bind to non-aggregated TDP-43 in the nucleus as compared with aggregated TDP-43 in the cytoplasm, whilst binding to both species. These binding properties may be demonstrated for example using immunohistochemistry. Suitable methodology is described herein with reference to Example 6 where relevant controls are provided. Results are shown in Table 7.

The invention also relates to compositions comprising a binding molecule, particularly an antibody or an antigen-binding fragment thereof, of the invention (including TDP-43-binding antibody fragments and derivatives) as described herein. The invention furthermore relates to immunotherapeutic and/or immunodiagnostic methods using such compositions in the prevention, diagnosis and/or treatment of a TDP-43 proteinopathy, wherein an effective amount of the composition is administered to a subject in need thereof.

In some embodiments, the invention encompasses binding molecules, particularly antibodies and antigen-binding fragments thereof of the invention as described herein that specifically bind TDP-43 and the use of these binding molecules to diagnose, prevent, alleviate and/or treat a disease, disorder and/or abnormality associated with TDP-43, in particular associated with TDP-43 aggregates, or TDP-43 proteinopathy including, but not limited to, frontotemporal dementia (FTD), amyotrophic lateral sclerosis (ALS), Alzheimer's disease (AD), Parkinson's disease (PD), Chronic Traumatic Encelopathy (CTE) and limbic-predominant age-related TDP-43 encephalopathy (LATE). The methods and compositions disclosed herein have applications in diagnosing, preventing, alleviating and/or treating a disease, disorder and/or abnormality associated with TDP-43, in particular associated with TDP-43 aggregates, or TDP-43 proteinopathy including but not limited to frontotemporal dementia (FTD), amyotrophic lateral sclerosis (ALS). Preferably, the use of these binding molecules to diagnose, prevent, alleviate and/or treat a disease, disorder and/or abnormality associated with TDP-43, in particular associated with TDP-43 aggregates, or TDP-43 proteinopathy is directed to amyotrophic lateral sclerosis (ALS), Alzheimer's disease (AD) or Frontotemporal dementia (FTD). More preferably, the use is directed to amyotrophic lateral sclerosis (ALS). More preferably, the use is directed to Alzheimer's disease (AD). More preferably, the use is directed to Frontotemporal dementia (FTD).

In another embodiment, a binding molecule, particularly an antibody or an antigen-binding fragment thereof of the invention as described herein specific for TDP-43 is contacted with a sample to detect, diagnose and/or monitor a disease, disorder and/or abnormality associated with TDP-43, in particular associated with TDP-43 aggregates, or TDP-43 proteinopathy, selected from Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy, Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP); also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES), Traumatic Brain Injury (TBI), Dementia with Lewy Bodies (DLB) or Parkinson's disease (PD).

In one embodiment, the invention encompasses binding molecules, particularly antibodies or antigen-binding fragments thereof of the invention as described herein that specifically bind TDP-43 and the use of these molecules, particularly of these antibodies, to detect the presence of TDP-43 in a sample. Accordingly, TDP-43 binding molecules of the invention, such as, anti-TDP43 antibodies as described herein, can be used, inter alia, to screen a clinical sample, in particular human blood, CSF, interstitial fluid (ISF) and/or urine for the presence of TDP-43 in samples, for example, by using an ELISA-based or surface adapted assay. Tissue samples may be used in some circumstances, such as brain tissue samples. The methods and compositions of the invention also have applications in diagnosing presymptomatic disease and/or in monitoring disease progression and/or therapeutic efficacy. According to some embodiments, an antibody specific for TDP-43 (e.g., a full-length antibody or a TDP-43 binding fragment or derivative of an antibody) is contacted with a sample (e.g., blood, cerebro-spinal fluid (CSF), interstitial fluid (ISF) or brain tissue) to detect, diagnose and/or monitor Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy, Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP); also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES), Traumatic Brain Injury (TBI), Dementia with Lewy Bodies (DLB) or Parkinson's disease (PD). The TDP-43 binding molecules of the invention may be used to quantify TDP-43 in suitable samples, in particular clinical samples such as blood, CSF, ISF or urine, with relatively high TDP-43 levels, as compared to a suitable control, indicating disease and/or more advanced disease. Many suitable immunoassay formats are known. Thus, the methods (such as ELISA, MSD (Meso Scale Discovery), HTRF (Homogeneous Time Resolved Fluorescence) and AlphaLISA) may be performed for diagnostic purposes with high levels of TDP-43 indicating disease. Alternatively, the methods may be performed for monitoring purposes. Increased levels over time may indicate progression of the disease. Decreased levels over time may indicate regression of the disease. The methods may also be used to monitor therapy, in particular to monitor the efficacy of a particular treatment. Successful therapy may be measured with reference to stable or decreasing levels of TDP-43 following treatment. It is demonstrated herein (Example 12) that TDP-43 levels were higher in CSF samples from TDP-43 proteinopathy patients than in control samples taken from healthy subjects (healthy control) when measured using antibodies of the invention. The control samples may or may not be run in parallel with the test samples. In some embodiments control levels are determined from a series of control samples taken from healthy subjects under similar or the same experimental conditions and used as a comparator for levels determined in the test sample. Methods of quantifying TDP-43 in suitable samples using binding molecules of the invention may also be used to select a therapy (for further treatment of the subject). Thus, personalized treatment methods are envisaged. A sample is taken before and after treatment. If treatment using the therapy results in stable or, preferably, decreasing levels of TDP-43 following treatment the therapy may be selected for that subject. If the therapy does not result in stable or, preferably, decreasing levels of TDP-43 following treatment the therapy is not selected for the subject. The therapy may be any suitable candidate therapeutic agent for treatment of TDP-43 proteinopathies. In preferred embodiments, the therapy comprises a TDP-43 binding molecule of the invention, typically in the form of a pharmaceutical composition as described herein.

The TDP-43 binding molecules of the invention may also be used for disease classification into particular types or subtypes. Thus, there is provided a method for classifying a disease, disorder and/or abnormality associated with TDP-43, in particular associated with TDP-43 aggregates or for classifying a TDP-43 proteinopathy comprising:

a. performing the methods of the invention in which levels of TDP-43 are quantified, as compared to suitable controls, b. optionally identifying mutations in a sample from the subject including but not limited to progranulin (GRN) mutation, C9orf72 mutations, TARDBP mutation, with valosine-containing protein (VCP) mutation, TARDBP mutation, angiogenin (ANG) mutation), mutation in the valosin-containing protein (VCP), mutation in the myotilin (MYOT) gene or mutations in the gene coding for desmin (DES), and c. classifying the disease, disorder and/or abnormality associated with TDP-43, in particular associated with TDP-43 aggregates, or TDP-43 proteinopathy.

Similarly, there is provided a method for classifying a disease, disorder and/or abnormality associated with TDP-43, in particular associated with TDP-43 aggregates, or for classifying a TDP-43 proteinopathy comprising: performing the methods of the invention in which levels of TDP-43 are quantified in a sample obtained from a subject with a disease, disorder and/or abnormality associated with TDP-43, or TDP-43 proteinopathy, wherein the levels are compared with control samples taken from subjects with different types or subtypes of disease, disorder and/or abnormality (i.e. a representative set of control levels are determined for the types or subtypes of interest) associated with TDP-43, in particular associated with TDP-43 aggregates, or TDP-43 proteinopathy; and classifying the disease, disorder and/or abnormality associated with TDP-43, in particular associated with TDP-43 aggregates, or TDP-43 proteinopathy based on the comparison. Thus, the classification is based on determining the closest match between the test sample and one or more of the control samples. These methods may further comprise identifying mutations in the sample including but not limited to progranulin (GRN) mutation, C9orf72 mutations, TARDBP mutation, with valosine-containing protein (VCP) mutation, TARDBP mutation, angiogenin (ANG) mutation), mutation in the valosin-containing protein (VCP), mutation in the myotilin (MYOT) gene or mutations in the gene coding for desmin (DES), wherein the identified mutations are also used to classify the disease, disorder and/or abnormality associated with TDP-43, in particular associated with TDP-43 aggregates, or TDP-43 proteinopathy. For the avoidance of doubt, the identification of mutations in a sample may be performed by any suitable method; for example based on nucleic acid sequencing of nucleic acid molecules within the sample. The sample may be separate and distinct from the sample in which TDP-43 levels are determined, but is from the same subject.

In other embodiments, the invention provides methods for preventing, alleviating and/or treating a disease, disorder and/or abnormality associated with TDP-43, in particular associated with TDP-43 aggregates, or TDP-43 proteinopathy. According to one embodiment, the methods of the invention comprise administering an effective concentration of a binding molecule, particularly an antibody of the invention specific for TDP-43 (e.g., a full-length antibody or a TDP-43 binding fragment or derivative of an antibody) as described herein to a subject. In another embodiment, the invention provides a method for preventing, alleviating and/or treating a TDP-43 proteinopathy. According to some embodiments, a binding molecule, particularly an antibody of the invention or an antigen-binding fragment thereof as described herein specific for TDP-43 is administered to treat, alleviate and/or prevent frontotemporal degeneration (FTD) or amyotrophic lateral sclerosis (ALS). In another embodiment, a binding molecule, particularly an antibody of the invention or an antigen-binding fragment thereof as described herein specific for TDP-43 is administered to prevent, alleviate and/or treat a neurodegenerative disease selected from frontotemporal dementia (FTD), amyotrophic lateral sclerosis (ALS), Alzheimer's disease (AD, including sporadic and familial forms of AD), Parkinson's disease (PD), Chronic Traumatic Encelopathy (CTE), limbic-predominant age-related TDP-43 encephalopathy (LATE).

In another embodiment, a binding molecule, particularly an antibody of the invention or an antigen-binding fragment thereof as described herein specific for TDP-43 is administered to prevent, alleviate and/or treat a disease selected from: Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy, Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP); also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES), Traumatic Brain Injury (TBI), Dementia with Lewy Bodies (DLB) or Parkinson's disease (PD).

DETAILED DESCRIPTION OF EMBODIMENTS OF THE INVENTION

X. Definitions

An "antigen binding molecule," as used herein, is any molecule that can specifically or selectively bind to an antigen, in particular TDP-43. A binding molecule may include or be an antibody or a fragment thereof. An anti-TDP-43 binding molecule is a molecule that binds to the TDP-43 protein, such as an anti-TDP-43 antibody or fragment thereof, at a specific recognition site, epitope. That is, antigen-binding molecules of the invention bind to an epitope within the amino acid sequence of SEQ ID NO: 1. The antigen-binding molecules, in particular antibodies or antigen-binding fragments thereof, provided herein recognize full-length TDP-43. Other anti-TDP-43 binding molecules may also include multivalent molecules, multi-specific molecules (e.g., diabodies), fusion molecules, aptamers, avimers, or other naturally occurring or recombinantly created molecules. Illustrative antigen-binding molecules useful in the present invention include antibody-like molecules. An antibody-like molecule is a molecule that can exhibit functions by binding to a target molecule (See, e.g., Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, DARPins (WO 2002/020565), Affibody (WO 1995/001937), Avimer (WO 2004/044011; WO 2005/040229), Adnectin (WO 2002/032925) and fynomers (WO 2013/135588).

The terms "anti TDP-43 antibody" and "an antibody that binds to TDP-43" or simply "antibody" as used herein refer to an antibody that is capable of binding TDP-43 with sufficient affinity such that the antibody is useful as a diagnostic and/or therapeutic agent in targeting TDP-43. In general, the term "antibody" is used herein in the broadest sense and encompasses various antibody structures, including but not limited to monoclonal antibodies, polyclonal antibodies, multispecific antibodies (e.g., bispecific or biparatopic antibodies), fully-human antibodies and antibody fragments so long as they exhibit the desired antigen-binding activity. Antibodies within the present invention may also be chimeric antibodies, recombinant antibodies, antigen-binding fragments of recombinant antibodies, humanized antibodies or antibodies displayed upon the surface of a phage or displayed upon the surface of a chimeric antigen receptor (CAR) T cell.

An "antigen-binding fragment" of an antibody refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to an epitope" within a defined region of a protein is an antibody that requires the presence of one or more of the amino acids within that region for binding to the protein.

In certain embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 20% of the binding to unaltered protein. In some embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 30%, at least 40%, at least 50%, at least 60%, at least 70%, at least 80%, or at least 90% of the binding to unaltered protein. In certain embodiments, binding of the antibody is determined by FACS, WB or by a suitable binding assay such as ELISA.

The term "binding to" as used in the context of the present invention defines a binding (interaction) of at least two "antigen-interaction-sites" with each other. The term "antigen-interaction-site" defines, in accordance with the present invention, a motif of a polypeptide, i.e., a part of the antibody or antigen-binding fragment of the present invention, which shows the capacity of specific interaction with a specific antigen or a specific group of antigens of TDP-43.

Said binding/interaction is also understood to define a "specific recognition". The term "specifically recognizing" means in accordance with this invention that the antibody is capable of specifically interacting with and/or binding to at least two amino acids of TDP-43 as defined herein, in particular interacting with/binding to at least two amino acids within amino acids residues 181-195, 199-213, 307-321, 352-366, 389-411, 397-411 and 140-200 of human TDP-43 (SEQ ID NO: 1), even more particularly interacting with binding to at least two amino acids within amino acids residues 183-188, 203-213, 204-208, 204-211, 205-210, 316-323, 358-361, 400-405, 400-406 or 400-412 of human TDP-43 (SEQ ID NO: 1).

The term "pan TDP-43 antibody" refers to an antibody that binds to misfolded aggregated TDP-43 and non-aggregated physiological TDP-43, including monomeric TDP-43, oligomeric TDP-43, post-translationally modified TDP-43 (such as phosphorylated, ubiquitinated, acetylated, sumoylated, and/or methylated), aggregated TDP-43 and truncated TDP-43.

The term "specific interaction" as used in accordance with the present invention means that the antibody or antigen-binding fragment thereof of the invention does not or does not essentially cross-react with (poly)peptides of similar structures. Accordingly, the antibody or antigen-binding fragment thereof of the invention specifically binds to/interacts with structures of TDP-43 formed by particular amino acid sequences within amino acids residues 181-195, 199-213, 307-321, 352-366, 389-411, 397-411 and 140-200 of human TDP-43 (SEQ ID NO: 1), more particularly binds to/interacts with structures of TDP-43 formed by particular amino acid sequences within amino acids residues 183-188, 203-213, 204-208, 204-211, 205-210, 316-323, 358-361, 400-405, 400-406 or 400-412 of human TDP-43 (SEQ ID NO: 1).

Cross-reactivity of antigen-binding molecules, in particular a panel of antibodies or antigen-binding fragments thereof under investigation may be tested, for example, by assessing binding of said panel of antibodies or antigen-binding fragments thereof under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, antigen-binding fragments thereof and the like) that bind to the certain structure of TDP-43 as defined herein, e.g., a specific epitope or (poly)peptide/protein of TDP-43 as defined herein but do not or do not essentially bind to any of the other epitope or (poly)peptides of the same TDP-43, are considered specific for the epitope or (poly)peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIACORE™), analytical ultracentrifugation, isothermal titration calorimetry, fluorescence anisotropy, fluorescence spectroscopy or by radiolabeled ligand binding assays.

Accordingly, specificity can be determined experimentally by methods known in the art and methods as described herein. Such methods comprise, but are not limited to Western Blots, ELISA-, RIA-, ECL-, IRMA-tests and peptide scans.

The term "monoclonal antibody" as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

The term "polyclonal antibody" as used herein, refers to an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

The term "fully-human antibody" as used herein refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse/murine immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may also be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term "chimeric antibodies", refers to an antibody which comprises a variable region of the present invention fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant (human) antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "heterohybrid antibody" refers to an antibody having light and heavy chains of different organismal origins. For example, an antibody having a human heavy chain associated with a murine light chain is a heterohybrid antibody. Examples of heterohybrid antibodies include chimeric and humanized antibodies.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: Jones et al., Nature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in context of the present invention, the term "antibody" relates to full immunoglobulin molecules as well as to parts of such immunoglobulin molecules (i.e., "antigen-binding fragment thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F(ab')2. The term antibody also comprises but is not limited to fully-human antibodies, chimeric antibodies, humanized antibodies, CDR-grafted antibodies and antibody constructs, like single chain Fvs (scFv) or antibody-fusion proteins.

"Single-chain Fv" or "scFv" antibody fragments have, in the context of the invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

Antibodies, antibody constructs, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook et al., Molecular Cloning: A Laboratory Manual; Cold Spring Harbor Laboratory Press, 2$^{nd}$ edition (1989) and 3$^{rd}$ edition (2001). The term "Ig-derived domain" particularly relates to (poly)peptide constructs comprising at least one CDR. Fragments or derivatives of the recited Ig-derived domains define (poly)peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991). CDR sequences provided herein are defined according to Kabat. However, it will be understood by the skilled person that the invention is intended to encompass binding molecules in which the CDR sequences are defined according to any useful identification/numbering scheme. For example, Chothia (Canonical structures for the hypervariable regions of immunoglobulins. Chothia C, Lesk AM. J Mol Biol. 1987 Aug. 20; 196(4):901-17), IMGT (IMGT, the international ImMunoGeneTics database. Giudicelli V, Chaume D, Bodmer J, Müller W, Busin C, Marsh S, Bontrop R, Marc L, Malik A, Lefranc MP. Nucleic Acids Res. 1997 Jan. 1; 25(1):206-11 and Unique database numbering system for immunogenetic analysis. Lefranc M P. Immunol Today. 1997 November; 18(11):509), MacCallum (MacCallum R M, Martin A C, Thornton J M, J Mol Biol. 1996 Oct. 11; 262(5):732-45) and Martin (Abhinandan K R, Martin ACR. Analysis and improvements to Kabat and structurally correct numbering of antibody variable domains. Mol Immunol. (2008) 45:3832-9. 10.1016/j.molimm.2008.05.022) numbering schemes may be adopted in order to define the CDRs.

Accordingly, in the context of the present invention, the antibody molecule described herein above is selected from the group consisting of a full antibody (immunoglobulin, like an IgG1, an IgG2, an IgG2a, an IgG2b, an IgA1, an IgGA2, an IgG3, an IgG4, an IgA, an IgM, an IgD or an IgE), F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin; see, inter alia, Jones et al., Nature 321 (1986), 522-525, Presta, Curr. Op. Struct. Biol. 2 (1992), 593-596. Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art (see e.g. LoBuglio, Proceedings of the American Society of Clinical Oncology Abstract (1997), 1562 and Khor, Proceedings of the American Society of Clinical Oncology Abstract (1997), 847).

Accordingly, in the context of this invention, antibody molecules or antigen-binding fragments thereof are provided, which are humanized and can successfully be employed in pharmaceutical compositions.

The specificity of the antibody or antigen-binding fragment of the present invention may not only be expressed by the nature of the amino acid sequence of the antibody or the antigen-binding fragment as defined above but also by the epitope to which the antibody is capable of binding. Thus, the present invention relates, in one embodiment, to an anti-misfolded TDP-43 antibody or an antigen-binding fragment thereof which recognizes the same epitope as an antibody of the invention.

It may be understood by a person skilled in the art that the epitopes may be comprised in the TDP-43 protein, but may also be comprised in a degradation product thereof or may be a chemically synthesized peptide. The amino acid positions are only indicated to demonstrate the position of the corresponding amino acid sequence in the sequence of the TDP-43 protein. The invention encompasses all peptides comprising the epitope. The peptide may be a part of a polypeptide of more than 100 amino acids in length or may be a small peptide of less than 100, preferably less than 50, more preferably less than 25 amino acids, even more preferably less than 16 amino acids. The amino acids of such peptide may be natural amino acids or nonnatural amino acids (e.g., beta-amino acids, gamma-amino acids, D-amino acids) or a combination thereof. Further, the present invention may encompass the respective retro-inverso peptides of the epitopes. The peptide may be unbound or bound. It may be bound, e.g., to a small molecule (e.g., a drug or a fluorophor), to a high-molecular weight polymer (e.g., polyethylene glycol (PEG), polyethylene imine (PEI), hydroxypropylmethacrylate (HPMA), etc.) or to a protein, a fatty acid, a sugar moiety or may be inserted in a membrane.

In order to test whether an antibody in question and the antibody of the present invention recognize the same epitope, the following competition study may be carried out: Vero cells infected with 3 MOI (multiplicity of infection) are incubated after 20 h with varying concentrations of the antibody in question as the competitor for 1 hour. In a second incubation step, the antibody of the present invention is applied in a constant concentration of 100 nM and its binding is flow-cytometrically detected using a fluorescence-labelled antibody directed against the constant domains of the antibody of the invention. Binding that conducts anti-proportional (inversely proportional) to the concentration of the antibody in question is indicative that both antibodies recognize the same epitope. However, many other assays are known in the art which may be used.

The present invention also relates to the production of specific antibodies against native polypeptides and recombinant polypeptides of TDP-43. This production is based, for example, on the immunization of animals, like mice. However, also other animals for the production of antibody/antisera are envisaged within the present invention. For example, monoclonal and polyclonal antibodies can be produced by rabbit, mice, goats, donkeys and the like. The polynucleotide encoding a correspondingly chosen polypeptide of TDP-43 can be subcloned into an appropriate vector, wherein the recombinant polypeptide is to be expressed in an organism capable of expression, for example in bacteria. Thus, the expressed recombinant protein can be intra-peritoneally injected into a mice and the resulting specific antibody can be, for example, obtained from the mice serum being provided by intra-cardiac blood puncture. The present invention also envisages the production of specific antibodies against native polypeptides and recombinant polypeptides by using a DNA vaccine strategy as exemplified in the appended examples. DNA vaccine strategies are well-known in the art and encompass liposome-mediated delivery, by gene gun or jet injection and intramuscular or intradermal injection. Thus, antibodies directed against a polypeptide or a protein or an epitope of TDP-43, in particular the epitope of the antibodies provided herein, can be obtained by directly immunizing the animal by directly injecting intramuscularly the vector expressing the desired polypeptide or a protein or an epitope of TDP-43, in particular the epitope of the antibodies of the invention, which lies within amino acid residues 181-195, 199-213, 307-321, 352-366, 389-411, 397-411 and 140-200 of SEQ ID NO:1, more particularly the epitope of the antibodies of the invention, which lies within amino acid residues aa 183-188, 203-213, 204-208, 204-211, 205-210, 316-323, 358-361, 400-405, 400-406, 400-412 of SEQ ID NO: 1. The amount of obtained specific antibody can be quantified using an ELISA, which is also described herein below. Further methods for the production of antibodies are well known in the art, see, e.g. Harlow and Lane, "Antibodies, A Laboratory Manual", CSH Press, Cold Spring Harbor, 1988.

Thus, under designated assay conditions, the specified antibodies and the corresponding epitope of TDP-43 bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Shepherd and Dean (2000), Monoclonal Antibodies: A Practical Approach, Oxford University Press and/or Howard and Bethell, for a description of immunoassay formats and conditions that can be used to determine specific immunoreactivity. Typically a specific or selective reaction will be at least twice background signal to noise and more typically more than 10 to 100 times greater than background. The person skilled in the art is in a position to provide for and generate specific binding molecules directed against the novel polypeptides. For specific binding-assays it can be readily employed to avoid undesired cross-reactivity, for example polyclonal antibodies can easily be purified and selected by known methods (see Shepherd and Dean, loc. cit.).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG2a, IgG2b, IgG3, IgG4, IgA1, and IgA2. The heavy chain constant domains that correspond to the different classes of immunoglobulins are called α, δ, ε, γ, and μ, respectively.

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gin |
| Asp (D) | Glu; Asn | Glu |
| Cys (C) | Ser; Ala | Ser |
| Gin (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244: 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; see Edelman, G. M. et al., Proc. Natl. Acad. USA, 63, 78-85 (1969)); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249: 533-545 (1986); US Pat Appl No US 2003/0157108 A1, Presta, L; and WO 2004/056312 A1, Adams et al., especially at Example 11), and knockout cell lines, such as alpha-1,6- fucosyltransferase gene, *FUT8*, knockout CHO cells (see, e.g., Yamane-Ohnuki et al., *Bioteeh. Bioeng.* 87: 614 (2004); Kanda, Y. et al., *Bioteehnol. Bioeng.*, 94(4):680-688 (2006); and W02003/085 107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement activation and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes and microglia express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al., *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)).

Alternatively, non-radioactive assays methods may be employed (see, for example, ACTI™ non radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells.

Alternatively, or additionally, ADCC activity of the molecule of interest may be assessed in vivo, e.g., in a animal model such as that disclosed in Clynes et al., *Proc. Nat'l Acad. sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Alternatively, antibodies with reduced effector function include those with substitution of one or more of Fe region residues 234, 235 and 329, so-called "PG-LALA" Fc mutant with substitution of residues 234 and 235 to alanine and 329 to glycine (Lo, M. et al., Journal of Biochemistry, 292, 3900-3908).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In certain embodiments, an antibody variant comprises a Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In certain embodiments, an antibody provided herein may be further modified to contain additional nonproteinaceous moieties that are known in the art and readily available. The moieties suitable for derivatization of the antibody include but are not limited to water soluble polymers. Nonlimiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Antibodies may be produced using recombinant methods and compositions, e.g., as described in U.S. Pat. No. 4,816, 567. In one embodiment, isolated nucleic acid encoding an anti-misfolded TDP-43 antibody described herein is provided. Such nucleic acid may encode an amino acid sequence comprising the VL and/or an amino acid sequence comprising the VH of the antibody (e.g., the Light and/or Heavy Chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20). In one embodiment, a method of making an anti-misfolded TDP-43 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-misfolded TDP-43 antibody, nucleic acid encoding an antibody, e.g., as described above, is isolated and inserted into one or more vectors for further cloning and/or expression in a host cell or a cell-free expression system. Such nucleic acid may be readily isolated and sequenced using conventional procedures (e.g., by using oligonucleotide probes that are capable of binding specifically to genes encoding the Heavy and Light Chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Val.* 248 (B. K. C. Lo, ed., Humana Press, Totowa, NJ, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are macaque kidney CV1 line transformed by SV40 (COS-7); human embryonic kidney line (293 or 293 cells as described, e.g., in Graham et al., *J. Gen Viral.* 36:59 (1977)); baby hamster kidney cells (BHK); mouse sertoli cells (TM4 cells as described, e.g., in Mather, *Biol. Reprod.* 23:243-251 (1980)); macaque kidney cells (CV 1); African green macaque kidney cells (VERO-76); human cervical carcinoma cells (HeLa); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y Aead. Sei.* 383:44-68 (1982); MRC 5 cells; and FS4 cells. Other useful mammalian host cell lines include Chinese hamster ovary (CHO) cells, including DHFR CHO cells (Urlaub et al., *Proc. Natl. Acad. cii. USA* 77:4216 (1980)); and myeloma cell lines such as YO, NSO and Sp2/0. For a review of certain mammalian host cell lines suitable for antibody production, see, e.g., Yazaki and Wu, *Methods in Molecular Biology, Val.* 248 (B. K. C. Lo, ed., Humana Press, Totowa, NJ), pp. 255-268 (2003).

Methods for producing a TDP-43 binding molecule of the invention, in particular an antibody, may comprise the steps of:
    a. culturing a suitable host cell or cell-free expression system under conditions suitable for producing the binding molecule, in particular the antibody; and
    b. isolating the binding molecule, in particular the antibody. Suitable culturing and isolation techniques are available to the skilled person.

Anti-TDP-43 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, immunofluorescence or immunohistochemistry.

In another aspect, competition assays may be used to identify an antibody that competes with any of the antibodies described herein for binding to TDP-43. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized TDP-43 is incubated in a solution comprising a first labeled antibody that binds to TDP-43 (e.g., any of the antibodies described herein) and a second unlabeled antibody that is being tested for its ability to compete with the first antibody for binding to TDP-43. As a control, immobilized TDP-43 is incubated in a solution comprising the first labeled antibody but not the second unlabeled antibody. After incubation under conditions permissive for binding of the first antibody to TDP-43, excess unbound antibody is removed, and the amount of label associated with immobilized TDP-43 is measured. If the amount of label associated with immobilized TDP-43 is substantially reduced in the test sample relative to the control sample, then that indicates that the second antibody is competing with the first antibody for binding to TDP-43. See Harlow and Lane (1988) *Antibodies: A Laboratory Manual* ch. 14 (Cold Spring Harbor Laboratory, Cold Spring Harbor, N.Y.).

The invention also provides immunoconjugates comprising an anti-TDP-43 antibody provided herein conjugated to one or more therapeutic agents, such as chemotherapeutic agents or drugs, growth inhibitory agents, toxins (e.g., protein toxins, enzymatically active toxins of bacterial, fungal, plant, or animal origin, or fragments thereof), radioactive isotopes (i.e., a radioconjugate), blood brain barrier penetration moieties or detectable labels.

In another aspect of the invention, an article of manufacture containing materials useful for the treatment, prevention and/or diagnosis of the diseases, disorders, abnormailites associated with TDP-43, in particular associated with TDP-43 aggregates, or TDP-43 proteinopathy described above is provided. The article of manufacture comprises a container and a label or package insert on or associated with the container. Suitable containers include, for example, bottles, vials, syringes, intravenous (IV) solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. It is understood that any of the above articles of manufacture may include an immunoconjugate of the invention in place of or in addition to an anti-TDP-43 antibody.

XI. Exemplary TDP-43 Specific Binding Molecules or Antibodies

In some embodiments of the invention, the antibody comprises:

a) V$_H$-CDR1 comprising the amino acid sequence of SEQ ID NO: 11; V$_H$-CDR2 comprising the amino acid sequence of SEQ ID NO: 12; and V$_H$-CDR3 comprising the amino acid sequence ES (Glu-Ser); VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17; or b) V$_H$-CDR1 comprising the amino acid sequence of SEQ ID NO: 21; V$_H$-CDR2 comprising the amino acid sequence of SEQ ID NO: 22; and V$_H$-CDR3 comprising the amino acid sequence ES (Glu-Ser); VL-CDR1 comprising the amino acid sequence of SEQ ID NO: 25; VL-CDR2 comprising the amino acid sequence of SEQ ID NO: 16; and VL-CDR3 comprising the amino acid sequence of SEQ ID NO: 27; or c) V$_H$-CDR1 comprising the amino acid sequence of SEQ ID NO: 31; V$_H$-CDR2 comprising the amino acid sequence of SEQ ID NO: 32; and V$_H$-CDR3 comprising the amino acid sequence of SEQ ID NO: 33; VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or d) V$_H$-CDR1 comprising the amino acid sequence of SEQ ID NO: 41; V$_H$-CDR2 comprising the amino acid sequence of SEQ ID NO: 42; and V$_H$-CDR3 comprising the amino acid sequence of SEQ ID NO: 43; VL-CDR1 comprising the amino acid sequence of SEQ ID NO: 45; VL-CDR2 comprising the amino acid sequence of SEQ ID NO: 46; and VL-CDR3 comprising the amino acid sequence of SEQ ID NO: 47; or e) V$_H$-CDR1 comprising the amino acid sequence of SEQ ID NO: 61; V$_H$-CDR2 comprising the amino acid sequence of SEQ ID NO: 62; and V$_H$-CDR3 comprising the amino acid sequence of SEQ ID NO: 63; VL-CDR1 comprising the amino acid sequence of SEQ ID NO: 65; VL-CDR2 comprising the amino acid sequence of SEQ ID NO: 66; and VL-CDR3 comprising the amino acid sequence of SEQ ID NO: 67; or f) V$_H$-CDR1 comprising the amino acid sequence of SEQ ID NO: 71; V$_H$-CDR2 comprising the amino acid sequence of SEQ ID NO: 72; and V$_H$-CDR3 comprising the amino acid sequence 73; VL-CDR1 comprising the amino acid sequence of SEQ ID NO: 75; VL-CDR2 comprising the amino acid sequence of SEQ ID NO: 16; and VL-CDR3 comprising the amino acid sequence of SEQ ID NO: 77; or g) V$_H$-CDR1 comprising the amino acid sequence of SEQ ID NO: 81; V$_H$-CDR2 comprising the amino acid sequence of SEQ ID NO: 82; and V$_H$-CDR3 comprising the amino acid sequence of SEQ ID NO: 83; VL-CDR1 comprising the amino acid sequence of SEQ ID NO: 85; VL-CDR2 comprising the amino acid sequence of SEQ ID NO: 86; and VL-CDR3 comprising the amino acid sequence of SEQ ID NO: 87; or h) V$_H$-CDR1 comprising the amino acid sequence of SEQ ID NO: 101; V$_H$-CDR2 comprising the amino acid sequence of SEQ ID NO: 102; and V$_H$-CDR3 comprising the amino acid sequence of SEQ ID NO: 103; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or i) V$_H$-CDR1 comprising the amino acid sequence of SEQ ID NO: 121; V$_H$-CDR2 comprising the amino acid sequence of SEQ ID NO: 122; and V$_H$-CDR3 comprising the amino acid sequence of SEQ ID NO: 123; VL-CDR1 comprising the amino acid sequence of SEQ ID NO: 125; VL-CDR2 comprising the amino acid sequence of SEQ ID NO: 16; and VL-CDR3 comprising the amino acid sequence of SEQ ID NO: 127; or j) V$_H$-CDR1 comprising the amino acid sequence of SEQ ID NO: 141; V$_H$-CDR2 comprising the amino acid sequence of SEQ ID NO: 142; and V$_H$-CDR3 comprising the amino acid sequence of SEQ ID NO: 143; VL-CDR1 comprising the amino acid sequence of SEQ ID NO: 145; VL-CDR2 comprising the amino acid sequence of SEQ ID NO: 146; and VL-CDR3 comprising the amino acid sequence of SEQ ID NO: 147; or k) V$_H$-CDR1 comprising the amino acid sequence of SEQ ID NO: 151; V$_H$-CDR2 comprising the amino acid sequence of SEQ ID NO: 152; and V$_H$-CDR3 comprising the amino acid sequence of SEQ ID NO: 153; VL-CDR1 comprising the amino acid sequence of SEQ ID NO: 155; VL-CDR2 comprising the amino acid sequence of SEQ ID NO: 156; and VL-CDR3 comprising the amino acid sequence of SEQ ID NO: 157.

In some embodiments, the antibody comprises:

a. a Heavy Chain Variable Region (V$_H$) comprising the sequence of SEQ ID NO: 10 and a Light Chain Variable Region (VL) comprising the sequence of SEQ ID NO: 14; or b. a Heavy Chain Variable Region (V$_H$) comprising the sequence of SEQ ID NO: 20 and a Light Chain Variable Region (VL) comprising the sequence of SEQ ID NO: 24; or c. a Heavy Chain Variable Region (V$_H$) comprising the sequence of SEQ ID NO: 30 and a Light Chain Variable Region (VL) comprising the sequence of SEQ ID NO: 34; or d. a Heavy Chain Variable Region (V$_H$) comprising the sequence of SEQ ID NO: 40 and a Light Chain Variable Region (VL) comprising the sequence of SEQ ID NO: 44; or e. a Heavy Chain Variable Region (V$_H$) comprising the sequence of SEQ ID NO: 60 and a Light Chain Variable Region (VL) comprising the sequence of SEQ ID NO: 64; or f. a Heavy Chain Variable Region (V$_H$) comprising the sequence of SEQ ID NO: 70 and a Light Chain Variable Region (VL) comprising the sequence of SEQ ID NO: 74; or

g. a Heavy Chain Variable Region (V$_H$) comprising the sequence of SEQ ID NO: 80 and a Light Chain Variable Region (VL) comprising the sequence of SEQ ID NO: 84; or h. a Heavy Chain Variable Region (V$_H$) comprising the sequence of SEQ ID NO: 100 and a Light Chain Variable Region (VL) comprising the sequence of SEQ ID NO: 104; or i. a Heavy Chain Variable Region (V$_H$) comprising the sequence of SEQ ID NO: 120 and a Light Chain Variable Region (VL) comprising the sequence of SEQ ID NO: 124; or j. a Heavy Chain Variable Region (V$_H$) comprising the sequence of SEQ ID NO: 140 and a Light Chain Variable Region (VL) comprising the sequence of SEQ ID NO: 144; or k. a Heavy Chain Variable Region (V$_H$) comprising the sequence of SEQ ID NO: 150 and a Light Chain Variable Region (VL) comprising the sequence of SEQ ID NO: 154.

In some embodiments, the antibody comprises:

a. a Heavy Chain Variable Region (V$_H$) comprising the sequence of SEQ ID NO: 10 or a Heavy Chain Variable Region (V$_H$) having at least 94%, 95%, 96%, 97%, 98% or 99% sequence identity to the amino acid sequence of SEQ ID NO: 10; and a Light Chain Variable Region (VL) comprising the sequence of SEQ ID NO: 14 or a Light Chain Variable Region (VL) having at least 96%, 97%, 98% or 99% sequence identity to the amino acid sequence of SEQ ID NO: 14; or b. a Heavy Chain Variable Region (V$_H$) comprising the sequence of SEQ ID NO: 20 or a Heavy Chain Variable Region (V$_H$) having at least 98% or 99% sequence identity to the amino acid sequence of SEQ ID NO: 20; and a Light Chain Variable Region (VL) comprising the sequence of SEQ ID NO: 24 or a Light Chain Variable Region (VL) having at least 97%, 98% or 99% sequence identity to the amino acid sequence of SEQ ID NO: 24; or c. a Heavy Chain Variable Region (V$_H$) comprising the sequence of SEQ ID NO: 30 or a Heavy Chain Variable Region (V$_H$) having at least 92%, 93%, 94%, 95%, 96%, 97%, 98%, or 99% sequence identity to the amino acid sequence of SEQ ID NO: 30; and a Light Chain Variable Region (VL) comprising the sequence of SEQ ID NO: 34 or a Light Chain Variable Region (VL) having at least 98% or 99% sequence identity to the amino acid sequence of SEQ ID NO: 34; or d. a Heavy Chain Variable Region (V$_H$) comprising the sequence of SEQ ID NO: 40 or a Heavy Chain Variable Region (V$_H$) having at least 90%, 91%, 92%, 93%, 94%, 95%, 96%, 97%, 98% or 99% sequence identity to the amino acid sequence of SEQ ID NO: 40; and a Light Chain Variable Region (VL) comprising the sequence of SEQ ID NO: 44; or e. a Heavy Chain Variable Region (V$_H$) comprising the sequence of SEQ ID NO: 60 or a Heavy Chain Variable Region (V$_H$) having at least 94%, 95%, 96%, 97%, 98% or 99% sequence identity to the amino acid sequence of SEQ ID NO: 60; and a Light Chain Variable Region (VL) comprising the sequence of SEQ ID NO: 64 or a Light Chain Variable Region (VL) having at least 99% sequence identity to the amino acid sequence of SEQ ID NO: 64; or f. a Heavy Chain Variable Region (V$_H$) comprising the sequence of SEQ ID NO: 70 or a Heavy Chain Variable Region ($V_H$) having at least 93%, 94%, 95%, 96%, 97%, 98% or 99% sequence identity to the amino acid sequence of SEQ ID NO: 70; and a Light Chain Variable Region (VL) comprising the sequence of SEQ ID NO: 74 or a Light Chain Variable Region (VL) having at least 99% sequence identity to the amino acid sequence of SEQ ID NO: 74; or g. a Heavy Chain Variable Region ($V_H$) comprising the sequence of SEQ ID NO: 80 or a Heavy Chain Variable Region ($V_H$) having at least 90%, 91%, 92%, 93%, 94%, 95%, 96%, 97%, 98% or 99% sequence identity to the amino acid sequence of SEQ ID NO: 80; and a Light Chain Variable Region (VL) comprising the sequence of SEQ ID NO: 84 or a Light Chain Variable Region (VL) having at least 96%, 97%, 98% or 99% sequence identity to the amino acid sequence of SEQ ID NO: 84; or h. a Heavy Chain Variable Region ($V_H$) comprising the sequence of SEQ ID NO: 100 or a Heavy Chain Variable Region ($V_H$) having at least 93%, 94%, 95%, 96%, 97%, 98%, or 99% sequence identity to the amino acid sequence of SEQ ID NO: 100; and a Light Chain Variable Region (VL) comprising the sequence of SEQ ID NO: 104 or a Light Chain Variable Region (VL) having at least 99% sequence identity to the amino acid sequence of SEQ ID NO: 104; or i. a Heavy Chain Variable Region ($V_H$) comprising the sequence of SEQ ID NO: 120 or a Heavy Chain Variable Region ($V_H$) having at least 89%, 90%, 91%, 92%, 93%, 94%, 95%, 96%, 97%, 98% or 99% sequence identity to the amino acid sequence of SEQ ID NO: 120; and a Light Chain Variable Region (VL) comprising the sequence of SEQ ID NO: 124 or a Light Chain Variable Region (VL) having at least 96%, 97%, 98% or 99% sequence identity to the amino acid sequence of SEQ ID NO: 124; or j. a Heavy Chain Variable Region ($V_H$) comprising the sequence of SEQ ID NO: 140 or a Heavy Chain Variable Region ($V_H$) having at least 93%, 94%, 95%, 96%, 97%, 98% or 99% sequence identity to the amino acid sequence of SEQ ID NO: 140; and a Light Chain Variable Region (VL) comprising the sequence of SEQ ID NO: 144; or k. a Heavy Chain Variable Region ($V_H$) comprising the sequence of SEQ ID NO: 150 or a Heavy Chain Variable Region ($V_H$) having at least 85%, 86%, 87%, 88%, 89%, 90%, 91%, 92%, 93%, 94%, 95%, 96%, 97%, 98% or 99% sequence identity to the amino acid sequence of SEQ ID NO: 150; and a Light Chain Variable Region (VL) comprising the sequence of SEQ ID NO: 154 or a Light Chain Variable Region (VL) having at least 99% sequence identity to the amino acid sequence of SEQ ID NO: 154.

In some embodiments, the invention relates to an antibody derived from hybridoma clones 631B2A2, 633B12C8, 634H10H7, 636E5B8, 641H1E7, 642A10B11, 642D12B4, 646B7F7, 712A6B10, 809D9C2 or 809F12D8, as described further herein.

In some embodiments, the invention relates to an antibody selected from ACI-7069-631B2-Ab1, ACI-7069-633B12-Ab1, ACI-7069-634H10-Ab2, ACI-7069-636E5-Ab1, ACI-7069-641H1-Ab2, ACI-7069-642A10-Ab1, ACI-7069-642D12-Ab1, ACI-7069-646B7-Ab1, ACI-7071-712A6-Ab1, ACI-7071-809D9-Ab2 and ACI-7071-809F12-Ab1, as described further herein.

In some embodiments, a(n isolated) nucleic acid is provided, wherein the (isolated) nucleic acid encodes an antibody described herein.

In some embodiments, a(n isolated) nucleic acid is provided, wherein the (isolated) nucleic acid comprises SEQ ID NO:18 encoding an anti-TPD-43 antibody.

In some embodiments, a(n isolated) nucleic acid is provided, wherein the (isolated) nucleic acid comprises SEQ ID NO:19 encoding an anti-TPD-43 antibody.

In some embodiments, a(n isolated) nucleic acid is provided, wherein the (isolated) nucleic acid comprises SEQ ID NO:28 encoding an anti-TPD-43 antibody.

In some embodiments, a(n isolated) nucleic acid is provided, wherein the (isolated) nucleic acid comprises SEQ ID NO:29 encoding an anti-TPD-43 antibody.

In some embodiments, a(n isolated) nucleic acid is provided, wherein the (isolated) nucleic acid comprises SEQ ID NO:38 encoding an anti-TPD-43 antibody.

In some embodiments, a(n isolated) nucleic acid is provided, wherein the (isolated) nucleic acid comprises SEQ ID NO:39 encoding an anti-TPD-43 antibody.

In some embodiments, a(n isolated) nucleic acid is provided, wherein the (isolated) nucleic acid comprises SEQ ID NO:48 encoding an anti-TPD-43 antibody.

In some embodiments, a(n isolated) nucleic acid is provided, wherein the (isolated) nucleic acid comprises SEQ ID NO:49 encoding an anti-TPD-43 antibody.

In some embodiments, a(n isolated) nucleic acid is provided, wherein the (isolated) nucleic acid comprises SEQ ID NO:68 encoding an anti-TPD-43 antibody.

In some embodiments, a(n isolated) nucleic acid is provided, wherein the (isolated) nucleic acid comprises SEQ ID NO:69 encoding an anti-TPD-43 antibody.

In some embodiments, a(n isolated) nucleic acid is provided, wherein the (isolated) nucleic acid comprises SEQ ID NO:78 encoding an anti-TPD-43 antibody.

In some embodiments, a(n isolated) nucleic acid is provided, wherein the (isolated) nucleic acid comprises SEQ ID NO:79 encoding an anti-TPD-43 antibody.

In some embodiments, a(n isolated) nucleic acid is provided, wherein the (isolated) nucleic acid comprises SEQ ID NO:88 encoding an anti-TPD-43 antibody.

In some embodiments, a(n isolated) nucleic acid is provided, wherein the (isolated) nucleic acid comprises SEQ ID NO:89 encoding an anti-TPD-43 antibody.

In some embodiments, a(n isolated) nucleic acid is provided, wherein the (isolated) nucleic acid comprises SEQ ID NO:108 encoding an anti-TPD-43 antibody.

In some embodiments, a(n isolated) nucleic acid is provided, wherein the (isolated) nucleic acid comprises SEQ ID NO:109 encoding an anti-TPD-43 antibody.

In some embodiments, a(n isolated) nucleic acid is provided, wherein the (isolated) nucleic acid comprises SEQ ID NO:128 encoding an anti-TPD-43 antibody.

In some embodiments, a(n isolated) nucleic acid is provided, wherein the (isolated) nucleic acid comprises SEQ ID NO:129 encoding an anti-TPD-43 antibody.

In some embodiments, a(n isolated) nucleic acid is provided, wherein the (isolated) nucleic acid comprises SEQ ID NO:148 encoding an anti-TPD-43 antibody.

In some embodiments, a(n isolated) nucleic acid is provided, wherein the (isolated) nucleic acid comprises SEQ ID NO:149 encoding an anti-TPD-43 antibody.

In some embodiments, a(n isolated) nucleic acid is provided, wherein the (isolated) nucleic acid comprises SEQ ID NO:158 encoding an anti-TPD-43 antibody.

In some embodiments, a(n isolated) nucleic acid is provided, wherein the (isolated) nucleic acid comprises SEQ ID NO:159 encoding an anti-TPD-43 antibody.

XII. Compositions and Methods

In some embodiments, an immunoconjugate is provided, wherein the immunoconjugate comprises an (isolated) antibody described herein and a therapeutic agent. In some embodiments, a labeled antibody is provided, comprising an antibody described herein and a detectable label.

In some embodiments, a pharmaceutical composition is provided, comprising an (isolated) antibody described herein and a pharmaceutically acceptable carrier.

In some embodiments the TDP-43 specific binding molecule of the present invention is linked to a detectable label.

In some embodiments the TDP-43 specific binding molecule is part of an immunoconjugate wherein the TDP-43 specific binding molecule is covalently linked to another suitable therapeutic agent.

In some embodiments the TDP-43 specific binding molecule or the immunoconjugate comprising it is present as a composition comprising a TDP-43 specific binding molecule and a TDP-43 agonists and cognate molecules, or alternately, antagonists of the same.

In some embodiments the TDP-43 specific binding molecule is part of pharmaceutical composition comprising a TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same combined with a pharmaceutically acceptable carrier.

In some embodiments the TDP-43 specific binding molecule is part of a detection and/or diagnostic kit comprising a TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same.

Kits containing the binding molecules of the invention are also provided. In particular, such kits may be useful for performing the diagnostic methods of the invention (which include classification, monitoring and therapy selection methods). Thus, a kit for diagnosis of a disease, disorder and/or abnormality associated with TDP-43, in particular associated with TDP-43 aggregates, or a TDP-43 proteinopathy, or for use in a method of the invention is provided comprising a TDP-43 specific binding molecule of the invention. Such kits may comprise all necessary components for performing the herein provided methods. Typically each component is stored separately in a single overall packaging. Suitable additional components for inclusion in the kits are, for example, buffers, detectable dyes, laboratory equipment, reaction containers, instructions and the like. Instructions for use may be tailored to the specific method for which the kit is to be employed. Suitably labelled TDP-43 binding molecules of the invention are also provided, which may be included in such kits.

In some embodiments the TDP-43 specific binding molecule is used in an immunodiagnostic method for use in the prevention, diagnosis or treatment of a TDP-43 proteinopathy.

In some embodiments the TDP-43 specific binding molecule is part of an immunotherapeutic method for the prevention, or treatment of a TDP-43 proteinopathy, wherein an effective amount of the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a subject in need thereof.

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a subject in need thereof is used to diagnose, prevent, alleviate or treat a disease, disorder and/or abnormality associated with TDP-43, in particular associated with TDP-43 aggregates, or TDP-43 proteinopathy including but not limited to frontotemporal dementia (FTD), amyotrophic lateral sclerosis (ALS), Alzheimer's disease (AD), Parkinson's disease (PD), Chronic Traumatic Encelopathy (CTE), limbic-predominant age-related TDP-43 encephalopathy (LATE).

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a subject in need thereof is used in a method for diagnosing or monitoring a disease, disorder and/or abnormality associated with TDP-43, in particular associated with TDP-43 aggregates, or TDP-43 proteinopathy selected from Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy, Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)), Traumatic Brain Injury (TBI), Dementia with Lewy Bodies (DLB) or Parkinson's disease (PD).

In other embodiment, the invention relates to any methods for detecting, diagnosing or monitoring a disease, disorder and/or abnormality associated with TDP-43, in particular associated with TDP-43 aggregates, or TDP-43 proteinopathy that is selected from frontotemporal dementia (FTD), amyotrophic lateral sclerosis (ALS), Alzheimer's disease (AD), Parkinson's disease (PD), Chronic Traumatic Encelopathy (CTE), and limbic-predominant age-related TDP-43 encephalopathy (LATE).

Preferably, the disease, disorder and/or abnormality associated with TDP-43, in particular associated with TDP-43 aggregates, or TDP-43 proteinopathyis selected from amyotrophic lateral sclerosis (ALS), Alzheimer's disease (AD) and Frontotemporal dementia (FTD). More preferably, the disease, disorder and/or abnormality associated with TDP-43, in particular associated with TDP-43 aggregates, or TDP-43 proteinopathy is amyotrophic lateral sclerosis (ALS). More preferably, the disease, disorder and/or abnormality associated with TDP-43, in particular associated with TDP-43 aggregates, or TDP-43 proteinopathy is Alzheimer's disease (AD). More preferably, the disease, disorder and/or abnormality associated with TDP-43, in particular associated with TDP-43 aggregates, or TDP-43 proteinopathy is Frontotemporal dementia (FTD).

In some embodiments the TDP-43 specific binding molecule is used in a method for diagnosing presymptomatic disease or for monitoring disease progression and therapeutic efficacy, or for predicting responsiveness, or for selecting subjects which are likely to respond to the treatment with a TDP-43 specific binding molecule. Said method is preferably performed using a sample of human blood or urine. Most preferably the method involves an ELISA-based or surface adapted assay.

In some embodiments the TDP-43 specific binding molecule is used in a method wherein a TDP-43 specific binding molecule of the present invention is contacted with a sample (e.g., blood, cerebrospinal fluid, or brain tissue) to detect, diagnose or monitor frontotemporal degeneration (FTD) or amyotrophic lateral sclerosis (ALS), Alzheimer's disease (AD), Chronic Traumatic Encelopathy, Perry syndrome, limbic-predominant age-related TDP-43 encephalopathy (LATE) and/or Parkinson's disease (PD).

In some embodiments the TDP-43 specific binding molecule is used in a method wherein a TDP-43 specific binding molecule of the present invention is contacted with a sample (e.g., blood, cerebrospinal fluid, or brain tissue) to detect, diagnose or a disease selected from Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy, Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)), Traumatic Brain Injury (TBI), Dementia with Lewy Bodies (DLB) or Parkinson's disease (PD).

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a subject in need thereof is used for preventing, alleviating or treating a disease, disorder and/or abnormality associated with TDP-43, in particular associated with TDP-43 aggregates, or TDP-43 proteinopathies, or frontotemporal degeneration (FTD) or amyotrophic lateral sclerosis (ALS), Alzheimer's disease (AD, including sporadic and familial forms of AD), Chronic Traumatic Encelopathy, Perry syndrome and limbic-predominant age-related TDP-43 encephalopathy (LATE) and/or Parkinson's disease (PD).

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a subject in need thereof is used for treating a disease selected from: Frontotemporal dementia (FTD, such as Sporadic or familial with or without motor-neuron disease (MND), with progranulin (GRN) mutation, with C9orf72 mutations, with TARDBP mutation, with valosine-containing protein (VCP) mutation, linked to chromosome 9p, corticobasal degeneration, frontotemporal lobar degeneration (FTLD) with ubiquitin-positive TDP-43 inclusions (FTLD-TDP), Argyrophilic grain disease, Pick's disease, semantic variant primary progressive aphasia (svPPA), behavioural variant FTD (bvFTD), Nonfluent Variant Primary Progressive Aphasia (nfvPPA) and the like), Amyotrophic lateral sclerosis (ALS, such as Sporadic ALS, with TARDBP mutation, with angiogenin (ANG) mutation), Alexander disease (AxD), limbic-predominant age-related TDP-43 encephalopathy (LATE), Chronic Traumatic Encelopathy, Perry syndrome, Alzheimer's disease (AD, including sporadic and familial forms of AD), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)), Traumatic Brain Injury (TBI), Dementia with Lewy Bodies (DLB) or Parkinson's disease (PD). Preferably said disease treatment helps to retain or increase mental recognition and or reduces the level of TDP-43 aggregates in the brain.

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a subject in need thereof is used for manufacturing a medicament for treating a disease, disorder and/or abnormality associated with TDP-43, in particular associated with TDP-43 aggregates, or TDP-43 proteinopathies or frontotemporal degeneration (FTD) or amyotrophic lateral sclerosis (ALS), Alzheimer's disease (AD, including sporadic and familial forms of AD), Chronic Traumatic Encelopathy, Perry syndrome and limbic-predominant age-related TDP-43 encephalopathy (LATE), and/or Parkinson's disease (PD).

Pharmaceutical formulations of an anti-TDP-43 antibody (the preferred type of TDP-43 specific binding molecule) or immunoconjugate as described herein are prepared by mixing such antibody or immunoconjugate having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn protein complexes); and/or non-ionic surfactants such as polyethylene glycol (PEG). Exemplary pharmaceutically acceptable carriers herein further include insterstitial drug dispersion agents such as soluble neutralactive hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules. The formulations to be used for in vivo administration are generally sterile. Sterility may be readily accomplished, e.g., by filtration through sterile filtration membranes.

Any of the antigen-binding molecules, anti-TDP-43 antibodies or immunoconjugates provided herein may be used in methods, e.g., therapeutic methods.

In another aspect, an anti-TDP-43 antibody (the preferred type of TDP-43 specific binding molecule) or immunoconjugate for use as a medicament is provided. In further aspects, an anti-misfolded TDP-43 antibody (the preferred type of TDP-43 specific binding molecule) or immunoconjugate for use in a method of treatment is provided. In certain embodiments, an anti-TDP-43 antibody (the preferred type of TDP-43 specific binding molecule) or immunoconjugate for use in the prevention, diagnosis and/or treatment of a TDP-43 proteinopathy is provided. In a preferred embodiment of the invention, an anti-TDP-43 antibody (the preferred type of TDP-43 specific binding molecule) or immunoconjugate is provided for use in the prevention, diagnosis and/or treatment of a disease, disorder and/or abnormality associated with TDP-43, in particular associated with TDP-43 aggregates, or TDP-43 proteinopathy including but not limited to frontotemporal dementia (FTD), amyotrophic lateral sclerosis (ALS), Alzheimer's disease (AD), Parkinson's disease (PD), Chronic Traumatic Encelopathy (CTE), and/or limbic-predominant age-related TDP-43 encephalopathy (LATE).

In a further aspect, the invention provides for the use of an anti-TDP-43 antibody (the preferred type of TDP-43 specific binding molecule) or immunoconjugate in the manufacture or preparation of a medicament. In one such embodiment, the method further comprises administering to the individual an effective amount of at least one additional therapeutic agent, e.g., as described below.

A "subject" or an "individual" according to any of the above embodiments may be an animal, a mammal, preferably a human.

In a further aspect, the invention provides pharmaceutical formulations comprising any of the anti-TDP-43 antibodies (the preferred type of TDP-43 specific binding molecule) or immunoconjugate provided herein, e.g., for use in any of the above therapeutic methods. In one embodiment, a pharmaceutical formulation comprises any of the anti-TDP-43 antibodies (the preferred type of TDP-43 specific binding molecule) or immunoconjugates provided herein and a pharmaceutically acceptable carrier. In another embodiment, a pharmaceutical formulation comprises any of the anti-TDP-43 antibodies (the preferred type of TDP-43 specific binding molecule) or immunoconjugates provided herein and at least one additional therapeutic agent, e.g., as described below.

Antibodies or immunoconjugates of the invention can be used either alone or in combination with other agents in a therapy. For instance, an antibody (the preferred type of TDP-43 specific binding molecule) or immunoconjugate of the invention may be co-administered with at least one additional therapeutic agent.

Such combination therapies noted above encompass combined administration (where two or more therapeutic agents are included in the same or separate formulations), and separate administration, in which case, administration of the antibody (the preferred type of TDP-43 specific binding molecule) or immunoconjugate of the invention can occur prior to, simultaneously, and/or following, administration of the additional therapeutic agent and/or adjuvant. Antibodies (the preferred type of TDP-43 specific binding molecule) or immunoconjugates of the invention can also be used in combination with radiation therapy.

An antibody (the preferred type of TDP-43 specific binding molecule) or immunoconjugate of the invention (and any additional therapeutic agent) can be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies (the preferred type of TDP-43 specific binding molecule) or immunoconjugates of the invention would be formulated, dosed, and administered in a fashion consistent with good medical practice. Factors for consideration in this context include the particular disease, disorder and/or abnormality associated with TDP-43, in particular associated with TDP-43 aggregates, or TDP-43 proteinopathy being treated, the particular mammal being treated, the clinical condition of the individual subject, the cause of the disease, a disorder and/or abnormality associated with TDP-43, in particular associated with TDP-43 aggregates, or TDP-43 proteinopathy, the site of delivery of the agent, the method of administration, the scheduling of administration, and other factors known to medical practitioners. The antibody or immunoconjugate need not be, but is optionally formulated with one or more agents currently used to prevent or treat the disease, disorder and/or abnormality associated with TDP-43, in particular associated with TDP-43 aggregates, or TDP-43 proteinopathy in question. The effective amount of such other agents depends on the amount of antibody or immunoconjugate present in the formulation, the type of disease, disorder and/or abnormality associated with TDP-43, in particular associated with TDP-43 aggregates or TDP-43 proteinopathy or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody (the preferred type of TDP-43 specific binding molecule) or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the subject's clinical history and response to the antibody or immunoconjugate, and the discretion of the attending physician. The antibody (the preferred type of TDP-43 specific binding molecule) or immunoconjugate is suitably administered to the subject at one time or over a series of treatments. Depending on the type and severity of the disease, about 1 µg/kg to 15 mg/kg (e.g. 0.1 mg/kg-10 mg/kg) of antibody (the preferred type of TDP-43 specific binding molecule) or immunoconjugate can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the subject. Such doses may be administered intermittently, e.g. every week or every three weeks (e.g. such that the subject receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-TDP-43 antibody (the preferred type of TDP-43 specific binding molecule).

In another aspect of the invention, an article of manufacture containing materials useful for the treatment, prevention and/or diagnosis of the diseases, disorders or abnormalities associated with TDP-43, in particular associated with TDP-43 aggregates, or TDP-43 proteinopathy, described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disease, disorder and/or abnormality associated with TDP-43, in particular associated with TDP-43 aggregates, or TDP-43 proteinopathy, and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice.

Moreover, the article of manufacture may comprise (a) a first container with a composition contained therein, wherein the composition comprises an antibody (the preferred type of TDP-43 specific binding molecule) or immunoconjugate of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In a further embodiment, the invention relates to a method of retaining or increasing cognitive memory capacity, movement and language function or preventing and/or slowing decline of cognitive memory capacity, movement and language function in a subject, comprising administering the binding molecule of the invention, the immunoconjugate of the invention, the composition of the invention or the pharmaceutical composition of the invention.

In a further embodiment, the invention relates to a method of reducing the level of TDP-43, comprising administering the binding molecule of the invention, the immunoconjugate of the invention, the composition of the invention or the pharmaceutical composition of the invention.

The methods of the invention may comprise administering at least one additional therapy, preferably wherein the additional therapy is selected from, but not limited to, neurological drugs, anti-abeta antibodies, anti-Tau antibodies, Tau aggregation inhibitors, beta-amyloid aggregation inhibitors, anti-BACE1 antibodies, and BACE1 inhibitors.

The invention furthermore relates to a method of detecting TDP-43, comprising contacting a sample with the binding molecule of the invention, preferably wherein the sample is a brain sample, a cerebrospinal fluid sample, urine sample or a blood sample.

EXAMPLES

Figure 1:
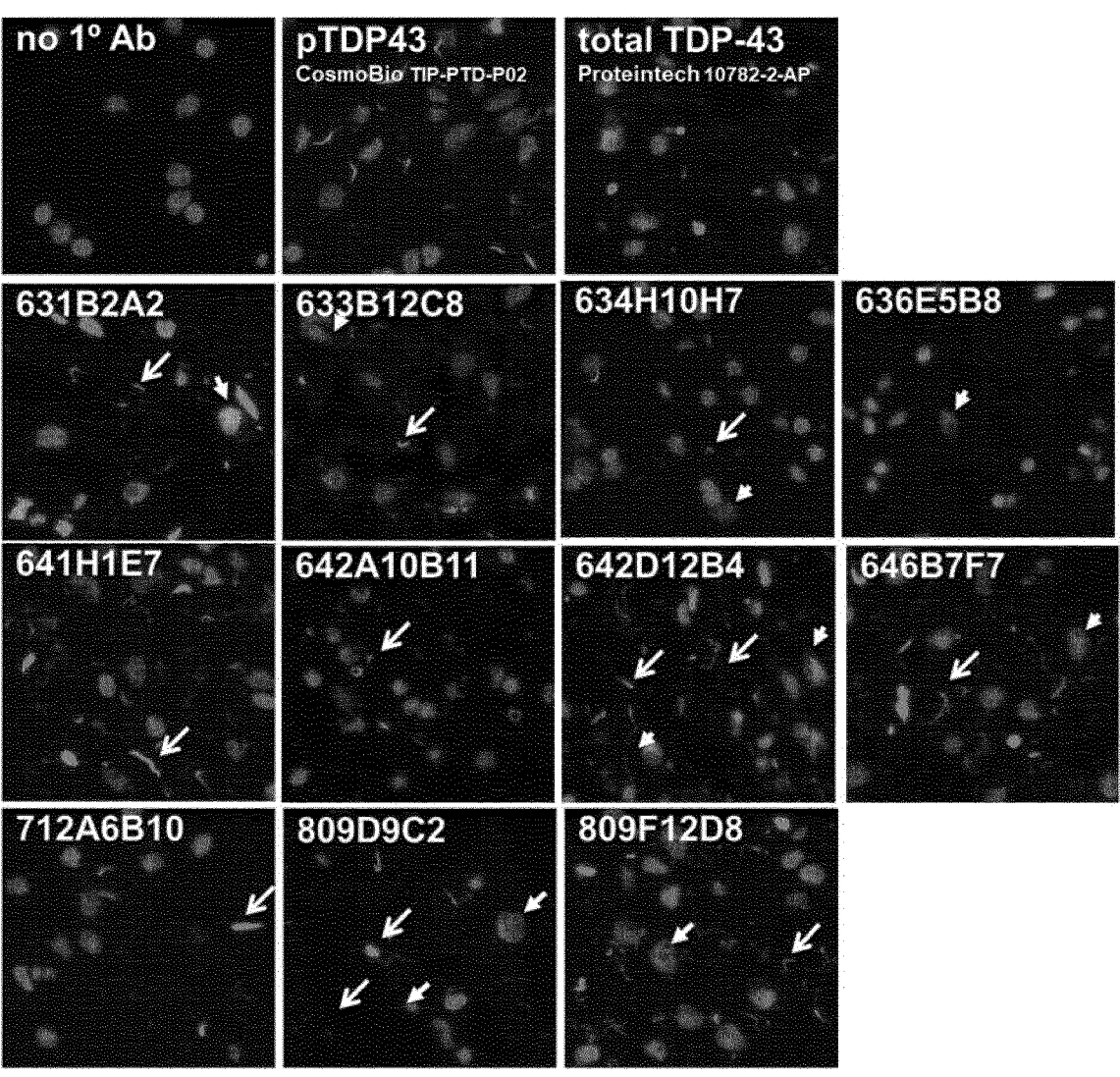
FIG. 1. Detection of TDP-43 in tissues sections from a subject with frontotemporal dementia (FTD) with type A pathology. Immunohistochemistry was performed on 10 m thick frozen sections from the frontal cortex of an FTD subject with type A pathology using a fluorescently labeled secondary antibody for detection. The following antibodies were used as controls: rabbit polyclonal pan TDP-43 antibody (Proteintech, 10782-2-AP) to detect pathological inclusions and physiological nuclear TDP-43; rabbit monoclonal phospho TDP-43 p409/410 antibody (Cosmobio, TIP-PTD-P02) to detect pathological aggregated and phosphorylated TDP-43. Arrows indicate TDP-43 aggregates; thick arrowheads indicate physiological TDP-43 in nuclei (nuclei are visualized by DAPI stain). Hybridoma name or commercial antibody source are indicated in the top left corner of each image.

Example 1: Preparation of a TDP-43 Vaccine Composition

The liposome-based vaccines were prepared according to the protocols published in WO2012/055933. Vaccines containing full length TDP-43 (FL TDP-43) protein as antigen (Table 2, SEQ ID NO: 1) were used for antibody generation.

TABLE 2

| TDP-43 protein and peptide antigen description | | |
| --- | --- | --- |
| SEQ ID NO | Definition | Amino acid sequence (1-letter code) |
| SEQ ID NO: 1 | Q13148 (UniProt) TADBP_HUMAN TAR DNA-binding protein 43 aa 1-414 | MSEYIRVTEDENDEPIEIPSEDDGTVLLSTVTAQFPGAC GLRYRNPVSQCMRGVRLVEGILHAPDAGWGNLVYVV NYPKDNKRKMDETDASSAVKVKRAVQKTSDLIVLGL PWKTTEQDLKEYFSTFGEVLMVQVKKDLKTGHSKGF GFVRFTEYETQVKVMSQRHMIDGRWCDCKLPNSKQS QDEPLRSRKVFVGRCTEDMTEDELREFFSQYGDVMDV |

US 12,600,766 B2

59 60

TABLE 2-continued

| SEQ ID NO | Definition | Amino acid sequence (1-letter code) |
|---|---|---|
|  |  | FIPKPFRAFAFVTFADDQIAQSLCGEDLIIKGISVHISNA EPKHNSNRQLERSGRFGGNPGGFGNQGGFGNSRGGG AGLGNNQGSNMGGGMNFGAFSINPAMMAAAQAALQ SSWGMMGMLASQQNQSGPSGNNQNQGNMQREPNQA FGSGNNSYSGSNSGAAIGWGSASNAGSGSGFNGGFGS SMDSKSSGWGM |

Example 2: Generation of Anti-TDP-43 Antibodies

A. Mouse Immunization

Female C57BL/6JOlaHsd (C57BL/6) and BALB/c OlaHsd (BALB/c) wild-type mice (Harlan, USA) were received at 9 weeks of age. Vaccinations started at 10 weeks. Mice were vaccinated with full-length TDP-43 protein presented on the surface of liposomes in the presence of Monophosphoryl Hexa-acyl Lipid A, 3-Deacyl (Synthetic) (3D-(6-acyl) PHAD®) as adjuvant.

Mice were vaccinated by subcutaneous injection (s.c.) on days 0, 4, 8, 21, 35, and 60. Mice were bled and heparinized plasma prepared 7 days before immunization (pre-immune plasma) and on days 14, 28, 42, 81 and 121 after first immunization. Mice used for myeloma fusion were additionally vaccinated with three daily booster injections of TDP-43 protein per i.p. injection without adjuvant.

Vaccine response was measured in mouse plasma. Binding of plasma derived antibodies from immunized mice to immobilized recombinant full-length (FL) TDP-43 indicated high titers for antibodies against TDP-43.

B. Generation of Hybridomas and Selection for Subcloning

Mice were euthanized and fusion with myeloma cells was performed using splenocytes from four individual mice. Screening for antibodies from the successfully fused hybridoma cell lines were performed as follows. Diluted (1:32) cell culture supernatants were analyzed using Luminex bead-based multiplex assay (Luminex, The Netherlands). Luminex beads were conjugated to FL TDP-43 and with capturing IgGs with anti-mouse IgG-Fc antibodies specific for the IgG1, IgG2a, IgG2b, IgG2c, and IgG3 subclasses (Jackson Immunoresearch, USA). Binding to beads conjugated to FL TDP-43 identified 386 hits derived from mice immunized with the FL TDP-43 liposomal vaccine.

Viable hybridomas were grown using serum-containing selection media. Clones with preferential binding to TDP-43 inclusions in human FTD brain and clones binding to C-terminus of TDP-43 were selected for further subcloning. Following limiting dilution, the clonal hybridomas were grown in low immunoglobulin containing medium and stable colonies were selected for antibody screening and selection. Antibodies shown in Table 3 were identified from this screen.

Example 3: Determination of Binding Efficacy (EC50)

Luminex assays with serial dilution of antibodies were performed as described before to determine half maximal effective concentration (EC50) of binding of antibodies to FL TDP-43. All EC50 values are summarized in Table 3. In summary, all tested antibodies bind to full length TDP-43 with high affinity.

TABLE 3

EC50 values determined by Luminex Assay

| Hybridoma Clone | Antibody Name | Isotype | κ, λ, chain | EC50 (μM) TDP-43 protein |
|---|---|---|---|---|
| 631B2A2 | ACI-7069-631B2-Ab1 | IgG1 | κ | <10 |
| 633B12C8 | ACI-7069-633B12-Ab1 | IgG2b | κ | <10 |
| 634H10H7 | ACI-7069-634H10-Ab2 | IgG2b | κ | <10 |
| 636E5B8 | ACI-7069-636E5-Ab1 | IgG2b | λ | <10 |
| 641H1E7 | ACI-7069-641H1-Ab2 | IgG2b | κ | <10 |
| 642A10B11 | ACI-7069-642A10-Ab1 | IgG1 | κ | 20 |
| 642D12B4 | ACI-7069-642D12-Ab1 | IgG2b | κ | <10 |
| 646B7F7 | ACI-7069-646B7-Ab1 | IgG2b | κ | <10 |
| 712A6B10 | ACI-7071-712A6-Ab1 | IgG2c | κ, λ | 180 |
| 809D9C2 | ACI-7071-809D9-Ab2 | IgG2b | κ | <10 |
| 809F12D8 | ACI-7071-809F12-Ab1 | IgG2b | κ | <10 |

Example 4: Antibody Binding to Human FL TDP-43

Antibody binding to human FL TDP-43 was determined using an indirect ELISA. ELISA plate coating with 1 μg/ml human FL TDP-43 was performed overnight in carbonate buffer at 4° C. Plates were washed with 0.05% Tween-20/PBS and then blocked with 1% bovine serum albumin (BSA) in 0.05% Tween-20/PBS for 1 hour at 37° C. Antibodies purified from hybridoma supernatants were then added in a 3-fold serial dilution starting at 1 μg/ml, and incubated for 2 hours at 37° C. after which the plates were washed. An AP-conjugated anti-mouse IgG secondary antibody (Jackson Immunoresearch Laboratories, United Kingdom) was added at 1/1000 dilution in 0.05% Tween-20/PBS for 1 hour at 37° C. After the final wash, plates were incubated with pNPP (Sigma-Aldrich, Switzerland) phosphatase substrate solution, and read at 405 nm using an ELISA plate reader (Tecan, Switzerland). All tested clones bind to full length TDP-43 with different EC50 values ranging from 10-1567 ng/ml (Table 4).

TABLE 4

EC50 values by ELISA

| Hybridoma clone name | EC50 ng/ml |
|---|---|
| 631B2A2 | 53 |
| 633B12C8 | 32 |
| 634H10H7 | 53 |
| 636E5B8 | 15 |
| 641H1E7 | 16 |
| 642A10B11 | 1567 |
| 642D12B4 | 14 |
| 646B7F7 | 11 |

TABLE 4-continued

| EC50 values by ELISA | |
| --- | --- |
| Hybridoma clone name | EC50 ng/ml |
| 712A6B10 | 102 |
| 809D9C2 | 17 |
| 809F12D8 | 14 |
| 2E2D3 Control | 20.7 |

Example 5: Epitope Mapping by ELISA and Peptide Array

Antibodies purified from serum-free hybridoma supernatants were screened by an indirect ELISA assay to determine binding regions using 40-66 aa linear peptides or a library of 15-mer peptides biotinylated on N-terminus and covering the entire sequence of TDP-43 with 9 aa offset and 6 aa overlap. Peptide sequences are provided in Table 5.

96-well plates were coated with 5 µg/ml non-biotinylated peptides overnight in carbonate buffer at 4° C.

Plates were washed with 0.05% Tween-20/PBS and then blocked with 1% bovine serum albumin (BSA) in 0.05% Tween-20/PBS for 1 hour at 37° C. The antibody purified from hybridoma supernatant was then added at 1 µg/ml, and incubated for 2 hours at 37° C. after which the plates were washed. An AP-conjugated anti-mouse IgG secondary antibody (Jackson Immunoresearch Laboratories, United Kingdom) was added at 1/1000 dilution in 0.05% Tween-20/PBS for 1 hour at 37° C. After the final wash, plates were incubated with pNPP (Sigma-Aldrich, Switzerland) phosphatase substrate solution, and read at 405 nm using an ELISA plate reader (Tecan, Switzerland).

For biotinylated peptides, 96-well streptavidin-coated ELISA plates were incubated with 5 µg/mL of biotinylated, 15-mer peptides. Plates were washed 3 times with 0.05% Tween-20/PBS and then blocked with 1% bovine serum albumin (BSA) in 0.05% Tween-20/PBS for 1 hour at 37° C. The antibody purified from hybridoma supernatant was then added at 1 µg/ml and incubated for 2 hours at 37° C. after which the plates were washed. An AP-conjugated anti-mouse IgG secondary antibody (Jackson ImmunoResearch Laboratories, United Kingdom) was added at 1/1000 dilution in 0.05% Tween-20/PBS for 1 hour at 37° C. After the final wash, plates were incubated with pNPP (Sigma-Aldrich, Switzerland), an AP substrate solution, and read at 405 nm using an ELISA plate reader (Tecan).

Determined binding regions are provided in Table 6. Tested antibodies were found to bind to the following peptides: TP-21, TP-23, TP-35, TP-40, TP-48, TDP-6 corresponding respectively to regions 181-195, 199-213, 307-321, 352-366, 389-411, 140-200 of SEQ ID NO: 1.

More precise linear epitopes were mapped using a library of 15-mer peptides directly synthesized on a solid support and covering the entire sequence of TDP-43 according to SEQ ID NO:1 with 1 aa offset and 14 aa overlap (Pepscan, Netherlands). The peptide arrays were blocked with horse serum and ovalbumin and incubated with purified antibody solution at concentrations between 0.75 and 5 µg/ml overnight at 4° C. After washing, the peptide arrays were incubated with a 1/1000 dilution of rabbit anti-mouse IgG (H+L) HRP conjugate (Southern Biotech, USA) for one hour at 25° C. After washing, the peroxidase substrate 2,2'-azino-di-3-ethylbenzthiazoline sulfonate (ABTS) and 20 µl/ml of 3% $H_2O_2$ were added. After one hour, the color development was quantified with a charge coupled device (CCD)—camera and an image processing system. These binding regions were confirmed by epitope mapping and the following epitopes (provided in Table 6) were identified: aa 183-188, 203-213, 204-208, 204-211, 205-210, 316-323, 358-361, 400-405, 400-406, 400-412 of SEQ ID NO:1.

TABLE 5

| Peptides used for determination of binding regions by ELISA | |
| --- | --- |
| Peptide number | Position according to SEQ ID NO: 1 |
| TP-21 | 181-195 |
| TP-23 | 199-213 |
| TP-35 | 307-321 |
| TP-40 | 352-366 |
| TP-48 | 389-411 |
| TDP-6 | 140-200 |

TABLE 6

| Binding regions and epitopes for tested antibodies | | |
| --- | --- | --- |
| Hybridoma clone name | Binding regions, aa | Epitopes, aa |
| 631B2A2 | 397-411 | 400-406 |
| 633B12C8 | 397-411 | 400-405 |
| 634H10H7 | 140-200 | 183-188 |
| 636E5B8 | 352-366 | 358-361 |
| 641H1E7 | 199-213 | 204-211 |
| 642A10B11 | 389-411 | 400-412 |
| 642D12B4 | 181-195 | 183-188 |
| 646B7F7 | 199-213 | 205-210 |
| 712A6B10 | 307-321 | 316-323 |
| 809D9C2 | 199-213 | 203-213 |
| 809F12D8 | 199-213 | 204-208 |

Example 6: Detection of TDP-43 in Brain Tissues from FTD/ALS Subjects by Immunohistochemistry Target engagement was evaluated in immunohistochemistry experiments on tissues from FTD subject brains. Human FTD brain tissues were obtained from The Netherlands Brain Bank, Netherlands Institute for Neuroscience, Amsterdam (open access: www.brainbank.nl) and Queen Square Brain Bank for Neurological Disorders, UCL. All material has been collected from donors from whom a written informed consent for brain autopsy and the use of the material and clinical information for research purposes has been obtained by the brain bank. Immunohistochemistry was performed on 10 µm thick frozen sections using fluorescently labeled secondary antibody for detection. The following antibodies were used as controls: rabbit polyclonal pan TDP-43 antibody (Proteintech, 10782-2-AP) to detect pathological inclusions and physiological nuclear TDP-43; rabbit monoclonal phospho TDP-43 p409/410 antibody (Cosmobio, TIP-PTD-P02) to detect pathological aggregated and phosphorylated TDP-43 and secondary antibody without primary antibody (No 1° Ab) to detect nonspecific background.

All antibodies of the present invention bind to nuclear, non-aggregated as well as aggregated TDP-43. Some antibodies of the present invention preferentially bind to aggregated TDP-43 in the cytoplasm in Type A pathology (FIG. 1). The detailed evaluation of binding characteristics is summarized in Table 7.

63

TABLE 7

| Detection of TDP-43 in brain tissues from FTD subjects | | |
| --- | --- | --- |
| Antibody Name | IHC detection of aggregated TDP-43 | IHC detection of nuclear non-aggregated TDP-43 |
| ACI-7069-631B2-Ab1 | +++ | +++ |
| ACI-7069-633B12-Ab1 | +++ | +++ |
| ACI-7069-634H10-Ab2 | ++ | ++ |
| ACI-7069-636E5-Ab1 | +/− | +++ |
| ACI-7069-641H1-Ab2 | +++ | + |
| ACI-7069-642A10-ab 1 | +++ | + |
| ACI-7069-642D12-Ab1 | ++ | + |
| ACI-7069-646B7-Ab1 | +++ | +++ |
| ACI-7071-712A6-Ab1 | ++ | + |
| ACI-7071-809D9-Ab2 | +++ | +++ |
| ACI-7071-809F12-Ab1 | +++ | +++ |

NA data not available; − absent; +/− not clear; +weak; ++medium; +++abundant

Example 7: Detection of TDP-43 in Brain Tissues from FTD/ALS Subjects by Western Blot A region of brain tissue (frontal cortex) was homogenized at 1:4 (w/v) ratio in the homogenization-solubilization buffer (HS buffer) at 4° C. with precellys using CK mix homogenization tubes (Labgene, BER0092). The following sequence was used for homogenization: 3 cycles of 30 s at 5000 rpm (with 15 s pause between each cycle). Homogenized samples were aliquoted and stored at −80° C. in 1.5 ml low protein binding tubes (Axygen MCT-175-L-C).

HS buffer—10 mM Tris.HCl pH 7.5, 150 mM NaCl, 0.1 mM EDTA, 1 mM DTT, complete EDTA-free protease inhibitors (Roche, 32524300) and PhosSTOP phosphatase inhibitors (Roche, 4906837001).

Brain homogenates were thawed on ice and resuspended in HS buffer to obtain final concentration of 2% Sarkosyl, 1 unit/μL Benzonase and 1 mM MgCl$_2$. The samples were then incubated at 37° C. under constant shaking at 600 rpm on a thermomixer for 45 min. The supernatants were collected in a new tube. The pellet was resuspended in 1000 μl of myelin floatation buffer and centrifuged at 20,000 g for 60 min at 4° C. on the benchtop centrifuge. The supernatant was carefully removed to remove all the floating lipids. This step was repeated if all the lipids could not be removed in a single step. The pellet was subsequently washed with PBS and centrifuged for 30 min at 4° C. on the benchtop centrifuge. The final pellet was resuspended on 200 μl PBS and stored at −80° C. The samples were analyzed by immunoblotting in denaturing conditions.

HS buffer with Sarkosyl, Benzonase and MgCl$_2$— 10 mM Tris.HCl pH 7.5, 150 mM NaCl, 0.1 mM EDTA, 1 mM DTT, 4% Sarkosyl, 1 Unit/μL Benzonase (Novagen 70746-4), 4 mM MgCl$_2$ Complete EDTA-free protease inhibitors (Roche) and PhosSTOP phosphatase inhibitors (Roche).

Myelin floatation buffer—HS buffer with 1% Triton X-100 and 30% Sucrose

Western blots were performed on Bolt 12% Bis-Tris Plus gel 1.0 mm (Thermofisher) using MES SDS running buffer (Thermofisher). Samples (30 μl/sample) were loaded on the gel once diluted in PBS, loading buffer (1×, Licor, 928-40004) containing 100 mM of DTT. Proteins were resolved under constant voltage for 100 V for 1 hour. After electrophoresis, proteins were transferred on nitrocellulose membrane (Thermofisher, IB23001) using iBLOT (Thermofisher, IB21001) at 20 volts for 7 mins. Following protein transfer, membranes were blocked for 1 hour in Licor blocking buffer

64

Figure 2:
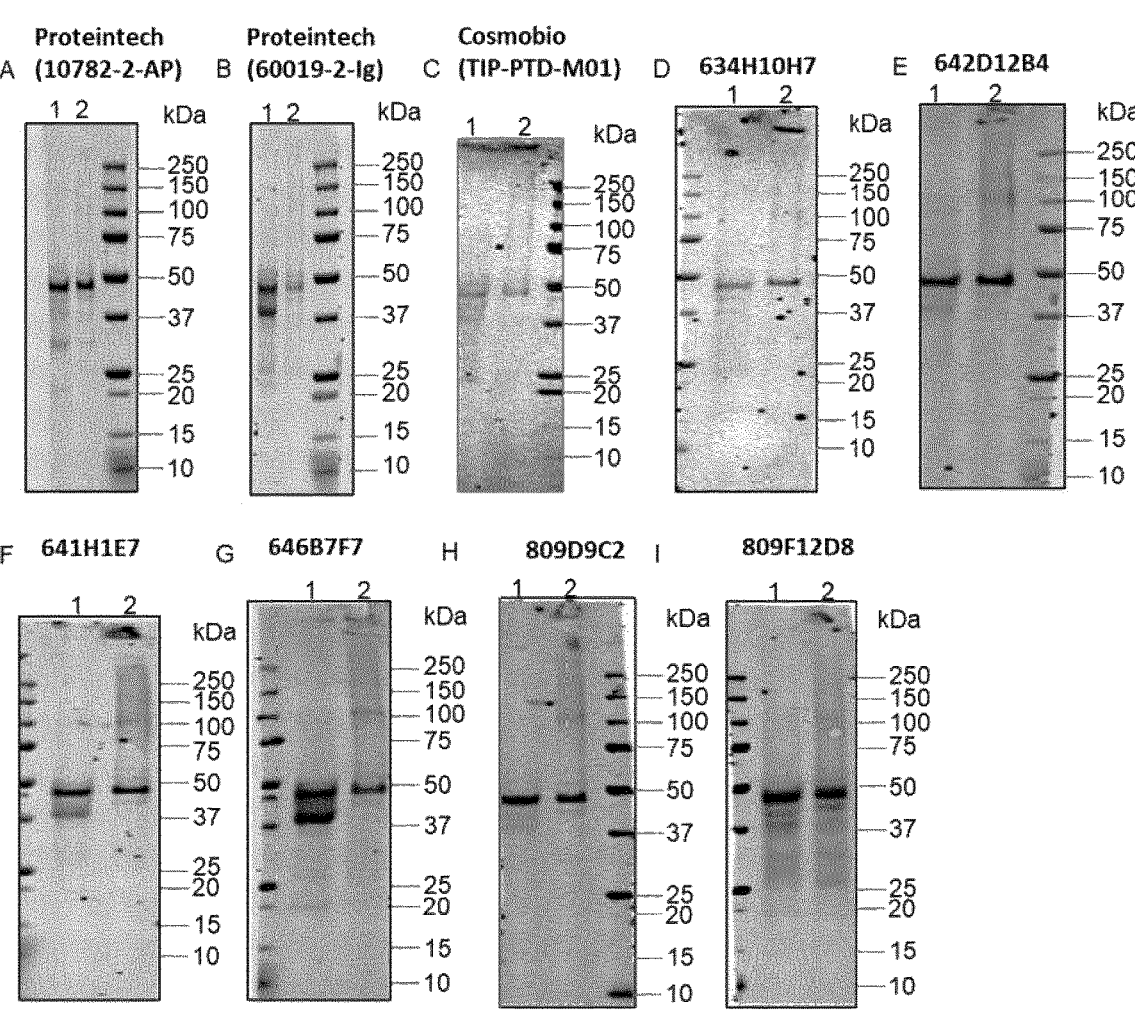
FIG. 2. TDP-43 detection in detergent (sarkosyl) soluble and insoluble fractions obtained from FTD type A postmortem brain tissue (frontal cortex). Immunoblots with commercial antibodies binding to either to N-terminal region (A, B) or the C-terminal region (C) show the presence of TDP-43 in sarkosyl soluble (lane 1) and insoluble (lane 2) fractions. Immunoblots with mAbs against TDP-43 generated in this study with epitopes in the N-terminal region of TDP-43 (D-I). Immunoblots with mAbs against TDP-43 that bind in the C-terminal region of TDP-43 (J-N). All mAbs against TDP-43 recognize full-length TDP-43 specifically. Additionally some mAbs (K, M, N) recognize pathological signatures of disease state such as C-terminal fragments in the insoluble fraction.
Figure 2:
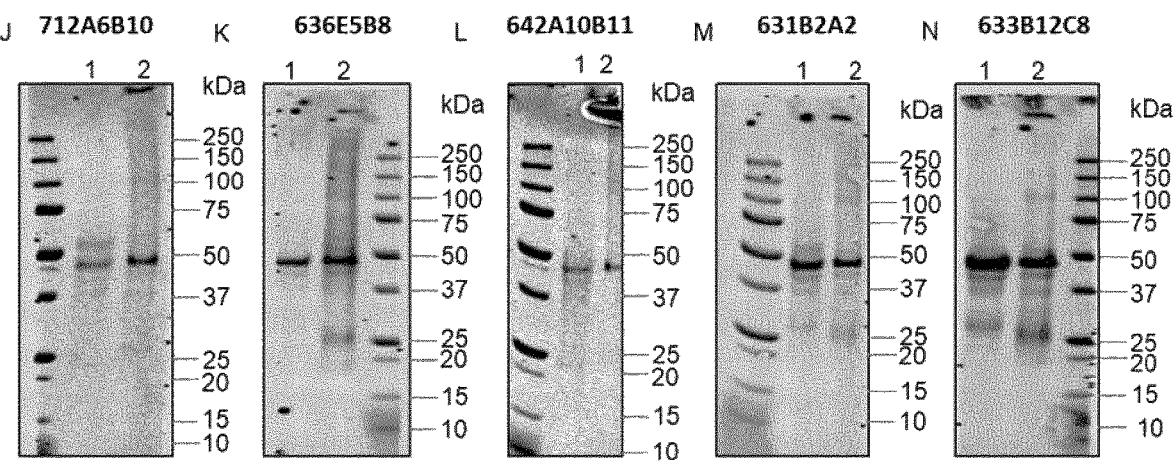

(Odyssey blocking buffer 927-40000) diluted 1:3 in PBS. Membranes were incubated overnight with the following primary antibodies: total TDP-43 (Proteintech, 60019-2-Ig or 10782-2-AP), pTDP-43 (Cosmobio, TIP-PTD-M01). For primary antibodies, blocking buffer was diluted 1:1 in PBS-T (PBS with 0.4% Tween-20). After 4 washes with PBS-T (PBS with 0.1% Tween-20), membranes were incubated with secondary antibodies coupled with the LICOR dye. Secondary antibodies—donkey anti-mouse (catalog number 926-68072) or goat anti-rabbit (catalog number 926-32211)—were used at a dilution of 1:10000 in Licor blocking buffer diluted 1:1 with PBS-T (PBS with 0.4% Tween-20) for 1 hour at room temperature. The membranes were washed again 4 times with PBS-T (PBS with 0.1% Tween-20) and scanned using the LICOR system. FIG. 2 shows that all mAbs recognize full-length TDP-43 specifically. Additionally some mAbs (K, M, N) recognize pathologic signatures of disease state such as C-terminal fragments in the insoluble fraction and high molecular weight aggregates.

Example 8a: Avidity Measurements Using SPR

Binding avidity to soluble or aggregated FL TDP-43 was evaluated by determining the dissociation constants (KD) using surface plasmon resonance (SPR; Biacore T200, GE Healthcare Life Sciences). Recombinant human soluble or aggregated FL TDP-43 were immobilized on a CM5 Series S sensor chip (GE Healthcare Life Sciences) by amine coupling. Soluble TDP-43 was immobilized at a concentration of 5 μg/ml in 10 mM sodium acetate (pH 4.5) with a flow rate of 5 μl/min for 420 seconds resulting in an immobilization level of 150 RU. Aggregated TDP-43 was immobilized at a concentration of 50 μg/ml in 10 mM sodium acetate (pH 4.5) with a flow rate of 5 μl/min for 840 seconds resulting in an immobilization level of 110 RU. Biotinylated TP-73 peptide (aa 181-190 of SEQ ID NO: 1) was immobilized on a Series S Sensor Chip SA (GE Healthcare Life Sciences) at a concentration of 5 μg/ml in PBS-P$^+$ with a flow rate of 5 μl/min for 30 seconds resulting in an immobilization level of 400 RU. To evaluate KD values, the purified antibodies and the control antibody (2E2-D3) were injected at 3-fold dilutions in PBS-P$^+$ starting from 333 nM and dilute down to 0.15 nM. The antibodies were injected at a flow rate of 50 μl/min for 90 seconds contact time and 700 seconds dissociation phase followed by three regenerations with 10 mM glycine-HCl pH 1.7. For the optimized SPR protocol the antibodies were diluted 3-fold starting from 300 nM and dilute down to 1.2 nM and injected for 300 seconds at 30 μl/min followed by 600 seconds dissociation. The surface was regenerated by one injection with 10 mM glycine-HCl pH 1.7. Results obtained from binding kinetics were double-referenced using a blank flow cell and a buffer cycle and were evaluated with a global 1:1 fitting model with RI. Avidities for 11 antibodies and two Fab fragments are depicted in Table 8. The antibodies of the invention bind aggregated TDP-43 with a KD ranging from 0.62 nM to 4.64 nM. In addition, some antibodies show preferential binding to aggregated TDP-43 as compared with soluble TDP-43. Two Fab fragments bind to soluble TDP-43 with a KD ranging from 2.8 nM to 21.8 nM and show similar KD for aggregated TDP-43. Two antibodies (marked with *) were re-analyzed using an optimized SPR protocol with longer association and dissociation phase which allows more accurate KD determination especially for antibodies with slow dissociation rates. The two antibodies bind to soluble TDP-43 with a KD ranging from 0.22 nM to 3.9 nM and to aggregated TDP-43 with a KD ranging from 0.18 nM to 0.69 nM. The antibody ACI-7069-642D12-Ab1 binds to TP-73 peptide with KD of 3.6 nM.

model with RI. On-rates (ka), off-rates (kd) and affinities (KD) for 3 antibodies are shown in Table 9 as mean values±SD of 12 (ACI-7069-633B12-Ab1), 2 (ACI-7069-

TABLE 8

Characterization of binding by SPR

| Hybridoma clone name | Soluble TDP-43 | | | | Aggregated TDP-43 | | | |
|---|---|---|---|---|---|---|---|---|
| | ka (1/Ms) | kd (1/s) | KD (nM) | Rmax (RU) | ka (1/Ms) | kd (1/s) | KD (nM) | Rma × (RU) |
| 631B2A2 | 1.59E+03 | 7.74E−04 | 486 | 243.4 | 8.61E+04 | 7.10E−05 | 0.82 | 72 |
| 633B12C8 | 8.73E+02 | 3.19E−04 | 365 | 323.3 | 8.21E+04 | 5.01E−05 | 0.62 | 74.1 |
| 633B12C8 Fab | 5.51E+04 | 1.46E−04 | 2.8 | 69.0 | 3.22E+04 | 2.15E−04 | 6.9 | 102.4 |
| 633B12C8* | 6.18E+04 | 1.08E−05 | 0.22 | 107.7 | 8.40E+04 | 1.32E−05 | 0.18 | 134.6 |
| 634H10H7 | 4.43E+04 | 8.74E−04 | 19.7 | 16 | 1.10E+05 | 1.66E−04 | 1.51 | 117.9 |
| 636E5B8 | 1.56E+04 | 6.82E−04 | 43.84 | 23.3 | 1.13E+05 | 2.74E−04 | 2.43 | 80.8 |
| 641H1E7 | 1.25E+05 | 8.41E−04 | 6.76 | 50.8 | 1.21E+05 | 1.93E−04 | 1.6 | 128.7 |
| 642A10B11 | NA | NA | NA | NA | 1.26E+06 | 5.85E−03 | 4.64 | 53.2 |
| 642D12B4 | 1.59E+05 | 8.38E−04 | 5.28 | 43.1 | 1.48E+05 | 1.31E−04 | 0.88 | 170.2 |
| 642D12B4 Fab | 1.28E+05 | 2.67E−03 | 21.8 | 43.0 | 9.40E+04 | 1.76E−03 | 21.8 | 275.9 |
| 642D12B4* | 1.15E+05 | 4.50E−04 | 3.9 | 74.3 | 1.49E+05 | 9.87E−05 | 0.69 | 498.7 |
| 646B7F7 | 1.78E+05 | 6.50E−04 | 3.66 | 67.3 | 1.44E+05 | 1.84E−04 | 1.28 | 148.3 |
| 712A6B10 | 1.34E+03 | 5.45E−04 | 406 | 85.7 | 3.48E+04 | 2.36E−05 | 0.68 | 29.4 |
| 809D9C2 | 7.71E+04 | 8.21E−04 | 10.6 | 47.7 | 9.59E+04 | 2.16E−04 | 2.25 | 88.4 |
| 809F12D8 | 9.94E+04 | 1.67E−04 | 1.68 | 70.6 | 9.47E+04 | 7.63E−05 | 0.81 | 132.3 |

NA, not applicable since less than three curves available for fit
*Characterization of binding using the optimized SPR protocol on recombinantly produced IgG2a isotype antibodies.

Example 8B3: Affinity Measurements Using SPR

Binding affinity to soluble FL TDP-43 was evaluated by determining the dissociation constants (KD) using surface plasmon resonance (SPR; Biacore T200, GE Healthcare Life Sciences). Goat-anti mouse capture antibody was immobilized on a CM5 Series S sensor chip (GE Healthcare Life 642D12-Ab1) or 3 (ACI-7071-809F12-Ab1) replicates. The antibodies ACI-7069-633B12-Ab1, ACI-7069-642D12-Ab1 and ACI-7071-809F12-Ab1 bind to soluble TDP-43 with affinities ranging from 15 to 135 pM, from 226 to 272 pM and from 389 to 457 pM, respectively. The antibody ACI-7069-633B12-Ab1 binds to TP-51 peptide with affinity ranging from 1184 to 1316 pM.

TABLE 9

Affinities for soluble FL TDP-43 and TP-51 peptide by SPR

| Hybridoma clone name | ACI-7069-633B12-Ab1 | | | ACI-7069-642D12-Ab1 | | | ACI-7071-809F12-Ab1 | | |
|---|---|---|---|---|---|---|---|---|---|
| | ka (1/Ms) | kd (1/s) | KD (pM) | ka (1/Ms) | kd (1/s) | KD (pM) | ka (1/Ms) | kd (1/s) | KD (pM) |
| Soluble TDP-43 Mean | 4.39E+04 | 3.45E−06 | 75 | 1.10E+05 | 2.76E−05 | 249 | 3.20E+04 | 1.36E−05 | 423 |
| Soluble TDP-43 SD | 5.35E+03 | 3.03E−06 | 60 | 8.00E+03 | 4.40E−06 | 23 | 2.16E+03 | 1.88E−06 | 34 |
| TP-51 Mean | 1.10E+05 | 1.38E−04 | 1250 | | | | | | |
| TP-51 SD | 9.41E+03 | 1.72E−05 | 66 | | | | | | |

Sciences) by amine coupling. Antibodies were captured at a concentration of 2-5 μg/ml in PBS-P+(GE Healthcare Life Sciences) with a flow rate of 10 μl/min for 120 seconds resulting in a capture level of 350-1000 RU. To evaluate KD values, FL TDP-43 or TP-51 peptide (aa 352-414 of SEQ ID NO: 1) was injected at a flow rate of 30 μl/min in single-cycle kinetics for 300 sec contact time in 3-fold dilutions PBS-P+ starting from 1.2 nM up to 100 nM. Dissociation was recorded for 1 h followed by one regeneration with 10 mM glycine-HCl pH 1.7. Results obtained from binding kinetics were double-referenced using a blank flow cell and a buffer cycle and were evaluated with a global 1:1 fitting

Example 9: Antibody Sequencing

Clonal hybridoma cell lysates were used for gene sequencing of the variable region. Mouse hybridomas were harvested and lysed using a lysis buffer containing guanidinium salts to deactivate RNases. Genomic DNA was then eliminated by RNase-free DNase, and RNA was purified with a silica-based affinity column using multiple washes and eluted from the column using RNase-free water. Once the RNA was extracted, its purity and concentration was measured spectrophotometrically. The integrity of the RNA was assessed on a denaturing agarose gel and RNA was reverse transcribed into cDNA using reverse transcriptase (RT). Before adding the RT reaction mixture, the RNA was heated to 70° C. for 10 min in order to disrupt RNA secondary structures. The RT products were directly used for PCR amplification. For high-fidelity PCR amplification of the cDNA, each of the variable region primers corresponding to the different gene families encoding for antibodies were individually mixed with the constant primer, for $V_H$ and VL separately in a total reaction volume of 50 µl. Initially, a degenerate primer pool was used (12 for $V_H$ and 12 for VL) and, depending on the results, a second pool was used to obtain PCR products. After the PCR reaction, the products were analyzed by gel electrophoresis on 2% agarose gels stained with ethidium bromide. The PCR products for VL and $V_H$ were individually purified on an agarose gel using tris-acetate-EDTA (TAE). The purified fragments excised from the gel were sequenced using the dye-terminator sequencing method using the same primers as those used for PCR. Sequencing was carried out in both directions to provide overlap at both ends. The sequences were analyzed using multiple sequence alignment (Clustal tool) and annotated using the algorithm of Kabat as described in Kabat et al., Sequences of Proteins of Immunological Interest, 91-3242 (1991). Nucleotide sequences of the Heavy Chain and Light Chain Variable Domains ($V_H$ and VL) are shown in Table 10. Translated protein sequences for selected Heavy ($V_H$) and Light (VL) Chain Variable Domains, and their complementarity-determining regions (CDRs) are shown in Table 11.

TABLE 10

| Nucleotide sequences of the Heavy Chain and Light Chain Variable Domains (VH and VL) | | | |
|---|---|---|---|
| Antibody Name | Hybridoma Code | VH | VL |
| ACI-7069-631B2-Ab1 | 631B2A2 | GAGGTCCAGCTGCAACAGTCT GGACCTGAACTGGTGAAGCCT GGGGCTTCAGTGAAGATATCC TGCAAGACTTCTGGATACACAT TCACTGAATACTCCATACACTG GGTGAAACAGAGCCATGGAGA GAGCCTTGAGTGGATTGGAGG TATTAATCCTGACAATGGTGGT ACTAGGTACAACCAGAAGTTC AAGGGCAAGGCGACATTGACT GTAGACAAGTCCTCCAGCACA GCCTACATGGACCTCCGCAGC CTGACATCTGAGGATTCTGCAG TTTATTATTGTGCAAGAGAGTC CTGGGGCCAAGGCACCACTCT CACAGTCTCCTCT (SEQ ID NO: 18) | GATGTTGTGATGACCCAGAC TCCACTCACTTTGTCGGTTAC CATTGGACAACCAGCCTCCA TCTCTTGCAAGTCAAGTCAGA GCCTCTTAAATAGTGATGGA AAGACATATTTGAATTGGTTG TTACAGAGGCCAGGCCAGTC TCCAAAGCGCCTAATCTATCT GGTGTCTAAACTGGACTCTA GAATCCCTGACAGGTTCACT GGCAGTGGATCAGGGACAGA TTTCACACTGAAAATCAGCA GAGTGGAGGCTGAGGATTTG GGAGTTTATTATTGCTGGCAA GGTACACATTTTCCTCACACG TTCGGTTCTGGGACCAAGCTG GAGCTGAAA (SEQ ID NO: 19) |
| ACI-7069-633B12-Ab1 | 633B12C8 | GAGGTCCAGCTGCAACAGTCT GGACCTGAACTGGTGAAGCCT GGGGCTTCAGTGAAGATATCC TGCAAGACTTCTGGATTCACAT TCACTGAATACTCCATGCACTG GGTGAAACAGAGCCATGGAAA GAGCCTTGAGTGGATTGGAGG TATTAATCCTAACAATGGTGGT ACTAGCTACAACCAGAAGTTC AAGGGCAAGGCCACATTGACT GTAGACAAGTCCTCCAGCACA GCCTACATGGAGCTCCGCAGC CTAACATCTGAGGATTCTGCAG TCTATTACTGTGCAAGAGAGTC CTGGGGCCAAGGCACCACTCT CACAGTCTCCTCA (SEQ ID NO: 28) | GATGTTGTGATGACCCAGAC TCCACTCACTTTGTCGGTTAC CATTGGACAACCAGCCTCCA TCTCTTGCAAGTCAAGTCAGA GCCTCTTACATAGTGATGGA AAGACATATTTGAATTGGTTG TTACAGAGGCCAGGCCAGTC TCCAAAGCGCCTAATCTATCT GGTGTCTAAACTGGACTCTA GAATCCCTGACAGGTTCACT GGCAGTGGATCAGGGACAGA TTTCACACTGAAAATCAGCA GAGTGGAGGCTGAGGATTTG GGAGTTTATTATTGCTGGCAA GGTACACATTTTCCTCACACG TTCGGTGCTGGGACCAAGCT GGAGCTGAAA (SEQ ID NO: 29) |
| ACI-7069-634H10-Ab2 | 634H10H7 | GAGGTTCAGCTGCAGCAGTCT GGGGCAGAGCTTGTGAAGCCA GGGGCCTCAGTCAGGTTGTCCT GCACAGCTTCTGGCTTCAACAT TAAAGACACCTATATGCACTG GGTGAAGCAGAGGCCTGAACA GGGCCTGGAATGGATTGGAAG GATTGATCCTGCGAATAGTAAT ACTAAATTTGACCCGAAGTTCC AGGGCAAGGCCACTATAACAT CAGACACATCCTCCAACACAG CCTACCTGCAGCTCAGCAGCCT | GACATCAAGATGACCCAGTC TCCATCCTCCATGTATGCATC GTTGGGAGAGAGAGTCACTA TCACTTGCAAGGCGAGTCAG GACATTAAAAGCTATTTAAG GACATTAAAAGCTATTTAAG CTGGTACCAGCATAAACCAT GGAAATCTCCTAAGGCCCTG ATCTATTATGCTACAAGCTTG GCAGATGGGGTCCCATCAAG ATTCAGTGGCAGTGGATCTG GGCAAGATTATTCTCTAACCA TCAGCAGCCTGGAGTCTGAC |

TABLE 10-continued

Nucleotide sequences of the Heavy Chain and Light Chain Variable Domains (VH and VL)

| Antibody Name | Hybridoma Code | VH | VL |
|---|---|---|---|
| | | GACATCTGAGGACACTGCCGT CTATTACTGTGCTAGATTCTAC GGTGGTAGCCACTGGTACTTCG ATGTCTGGGGCGCAGGGACCA CGGTCACCGTCTCCTCA (SEQ ID NO: 38) | GATACAGCAACTTACTACTGT CTACAGCAAGGTGAGAGCCC GTACACGTTCGGAGGGGGGA CCAAGCTGGAAATAAAA (SEQ ID NO: 39) |
| ACI-7069-636E5-Ab1 | 636E5B8 | GAGGTACATCTGGTGGAGTCT GGGGGAGACTTAGTGATGCCT GGAGGGTCCCTGAAGCTCTCCT GTGCAGCCTCTGGATTCACTTT CAGTAACTATGGCATGTCTTGG GTTCGCCAGACTCCAGACAAG AGGCTGGAGTGGGTCGCAACC ATTAGTAGTGGTGGTAAATAT ATCAACTACTTAGACAGTTTGA AGGGGCGATTCACCATCTCCA GAGACAATGCCAAGAACACCC TATACCTGCAAATGAGCAGTCT GAAGTCTGAGGATCAGCCAT GTATTACTGTGCAAAAGACTA CGGTAGTGGCTGGGCCTGGTTT GCTTACTGGGGCCAAGGGACT CTGGTCACTGTCTCTGCA (SEQ ID NO: 48) | CAACTTGTGCTCACTCAGTCA TCTTCAGCCTCTTTCTCCCTG GGAGCCTCAGCAAAACTCAC GTGCACCTTGAGTAGTCAGC ACAGTACGTACACCATTGAA TGGTATCAGCAACAGCCACT CAAGCCTCCTAAGTATGTGAT GGAGCTTAAGAAAGATGGAA GCCACAGCACAGGTGATGGG ATTCCTGATCGCTTCTCTGGA TCCAGCTCTGGTGCTGATCGC TACCTTAGCATTTCCAACATC CAGCCTGAAGATGAAGCAAT ATACATCTGTGGTGTGGGTG ATACAATTAAGGAACAATTT GTGTATGTTTTCGGCGGTGGA ACCAAGGTCACTGTCCTA (SEQ ID NO: 49) |
| ACI-7069-641H1-Ab2 | 641H1E7 | CAGGTGCAGCTGAAGGAGTCA GGACCTGGCCTGGTGGCGCCC TCACAGAGCCTGTCCATCACTT GTACTGTCTCTGGGTTTTCATT AACCAACTATGGTGTACACTG GGTTCGCCAGCCTCCAGGAAG GGGTCTGGAGTGGCTGGGACT AATGTGGGCTGGTGGAAGCAC AAATTATAATTCGGCTCTCATG TCCAGACTGAGCATCAGCAAA GACAACTCCAAGAGTCAAGTT TTCTTAAAAATGAACAGTCTGC AAACTGATGACACAGCCATGT ACTACTGTGTCATCTATAGGAC GGGGTTTGCTTACTGGGGCCA AGGGACTCTGGTCACTGTCTCT GCA (SEQ ID NO: 68) | GATGTTTTGATGACCCAAACT CCACTCTCCCTGCCTGTCAGT CTTGGAGATCAAGCCTCCATC TCTTGCAGATCTAGTCAGAGC ATTGTACATACTATTGGAAAC ACCTATTTAGAATGGTACCTG CAGAAACCAGGCCAGTCTCC AAAGCTCCTGATCTACAAAG TTTCCAACCGGTTTTCTGGGG TCCCAGACAGGTTCAGTGGC AGTGGATCAGGGACAGATTT CACACTCAAGATCAGCAGAG TGGAGGCTGAGGATCTGGGA GTTTATTACTGCTTTCAAGGT TCACATGTTCCATTCACTTTC GGCTCGGGGACAAAGTTGGA AATAAAA (SEQ ID NO: 69) |
| ACI-7069-642A10-ab1 | 642A10B11 | CAGGTCCAACTGCAGCAGCCT GGGGCTGAACTGGTGAAGCCT GGGGCTTCAGTGAAGCTGTCCT GCAAGGCTTCTGGCTACACCTT CACCAAGTACTGGATGCACTG GGTGAAGCAGAGGCCTGGACA AGGCCTTGAGTGGATTGGAGA GATTAATCCTAGCAACGGTCGT ACTAACTACAATGAGAAGTTC AAGAGCAAGGCCACACTGACT GTAGACAAATCCTCCAGCACA GCCTACATGCAACTCAGCAGC CTGACATCTGAGGACTCTGCG GTCTATTACTGTGCAAGATATA TGGACTACTGGGGTCAAGGAA CCTCAGTCACCGTCTCCTCA (SEQ ID NO: 78) | GATGTTGTGATGACCCAGAC TCCACTCACTTTGTCGGTTAC CATTGGACAACCAGCCTCCA TCTCTTGCAAGTCAAGTCAGA GCCTCTTTGATCGTGATGGAA AGACATATTTGAATTGGTTGT TACAGAGGCCAGGCCAGTCT CCAAAGCGCCTAATCTATCTG GTGTCTAAACTGGACTCTGG AGTCCCTGACAGGTTCACTG GCAGTGGATCAGGGACAGAT TTCACACTGAAAATCAGCAG AGTGGAGGCTGAGGATTTGG GAGTTTATTATTGCTGGCAAG GTACACATTTTCCGTGGACGT TCGGTGGAGGCACCAAGCTG GAAATCAAA (SEQ ID NO: 79) |
| ACI-7069-642D12-Ab1 | 642D12B4 | GAGGTTCAGCTGCAGCAGTCT GGGGCAGAGCTTGTGAAGCCG GGGGCCTCAGTCAGGTTGTCCT GCACAGCTTCTGGCTTCAACAT TAAAGACCCCTATATGCACTG GGTCAGGCAGAGGCCTAAACA GGGCCTGGAGTGGATTGGAAG GATTGATCCTGCGGATGGTAAT ACTAAATATGACCCGAAGTTC CAGGGCAAGGCCACTTTAACA | GACATCAAGATGACCCAGTC TCCATCCTCCATGTATGCATC GTTGGGAGAGAGAGTCACTA TCACTTGCAAGGCGAGTCAG GACATTAAAGGTATTTAAG CTGGTACCAGCAGAAACCAT GGAAATCTCCTAAGATCCTG ATCTATTATGCAACAAGCTTG GCAGATGGGGTCCCATCAAG ATTCAGTGGCACTGGATCTG |

TABLE 10-continued

| | | Nucleotide sequences of the Heavy Chain and Light Chain Variable Domains (VH and VL) | |
|---|---|---|---|

| Antibody Name | Hybridoma Code | VH | VL |
|---|---|---|---|
| | | GCAGACACATCCTCCAATGTA GCCTACCTGCACCTCAGCAGCC TGACATCTGAGGACACTGCCG TCTATTACTGTGCTAGATTCTA CGGTAGTAGCCACTGGTATTTC GATGTGTGGGGCGCAGGGACC ACGGTCACCGTCTCCTCA (SEQ ID NO: 88) | GACAAGATTATTCTCTAACCA TCAGCAGCCTGGAGTCTGAC GATGTAGCAACTTACTACTGT CTACAGCAAGGTGAGAGCCC GTACACGTTCGGAGGGGGGA CCAAGCTGGAAATAAAA (SEQ ID NO: 89) |
| ACI-7069-646B7-Ab1 | 646B7F7 | CAGGTGCAACTGAAGGAGTCA GGACCTGGCCTGGTGGCGCCC TCACAGAGCCTGTCCATCACTT GTACTGTCTCTGGATTTTCATT AACCAACTTTGGTGTACACTGG GTTCGCCAGCCTCCAGGAAAG GGTCTGGAGTGGCTGGGAATA ATGTGGGCTGGTGGAAGCACA AATTATAATTCGGCTCTCATGT CCAGACTGAGCATCAGCAAAG ACAACTCCAAGAGTCAAGTTTT CTTAAAAATGAACAGTCTCCA AACTGATGACACAGCCATGTA CTACTGTGTCATCTATAAGACG GGGTTTGCTTACTGGGGCCAA GGGACTCTGGTCACTGTCTCTG CA (SEQ ID NO: 108) | GATGTTTTGATGACCCAAACT CCCACTCTCCCTGCCTGTCAGT CTTGGAGATCAAGCCTCCATC TCTTGCAGATCTAGTCAGAGC ATTGTACATGCTATTGGAAAC ACCTATTTAGAATGGTACCTG CAGAAACCAGGCCAGTCTCC AAAGCTCCTGATCTACAAAG TTTCCAACCGGTTTTCTGGGG TCCCAGACAGGTTCAGTGGC AGTGGATCAGGGACAGATTT CACACTCAAGATCAGCAGAG TGGAGGCTGAGGATCTGGGA GTTTATTACTGCTTTCAAGGT TCACATGTTCCATTCACGTTC GGCTCGGGGACAAAGTTGGA AATAAAA (SEQ ID NO: 109) |
| ACI-7071-712A6-Ab1 | 712A6B10 | CAGGTCCAGCTGCAGCAGTCT GGAGCTGAGCTGGTGAAACCC GGGACATCAGTGAAGCTGTCC TGTAAGGCTTCTGCCTACACCT TCACTGAATATACTATACACTG GATAAAGCAGAAATCTGGACA GGGTCTTGAGTGGATTGGGTG GTTTCACCCTGAAAATGATAAT ATAAAGTACAATGAGAATTTC AAGGACAAGGCCACATTGACT GCGGACAGATCCTCCAGCACA GTCTATATGGAACTTAGTAGAT TGACATCTGAAGACTCTGCGGT CTATTTCTGTGCAGGGACGTCA GGCTACGGAGACTACTGGGGC CAAGGCACCACTCTCACAGTCT CTTCA (SEQ ID NO: 128) | GATGTTGTGATGACCCAGATT CCACTCACTTTGTCGATTACC ATTGGACAACCAGCCTCCAT CTCTTGCAAGTCAAGTCAGA GCCTCTTACCTAGTGATGGAA AGACATATTTGAATTGGTTGT TACAGAGGCCAGGCCAGTCT CCAAAGCGCCTAATCTATCTG GTGTCTAAACTGGACTCTGG AGTCCCTGACAGGTTCACTG GCAGTGGATCAGGGACAGAT TTCACACTGAAAATCAGCAG AGTGGAGGCTGACGATTTGG GAGTTTATTATTGCTGGCAAG GTACACATTTTCCTCCTACGT TCGGTGCTGGGACCAAGCTG GAACTGAAA (SEQ ID NO: 129) |
| ACI-7071-809D9-Ab2 | 809D9C2 | CAGGTCCAGCTGCAGCAGTCT GGGGCTGAGCTGGTGAGGCCT GGGGTCTCAGTGAAGATTTCCT GCAAGGGTTCTGGCTACAAAT TCACTGATTATTCTATGCACTG GGTGAAACAGAGTCATACAAA GAGTCTAGAGTGGATTGGAGT TATTAGTACTTACTATGGTGAT ACTACCTACAACCAGAAATTC AAGGGCAAGGCCACAATCACT GTAGACAAATCCTCCAGCACA GCCTATATGGAACTTGCCAGA CTGACATCTGAGGATTCTGCCA TCTATTACTGTGCAACGTACGG TAACTTCCCGGCCTCATTTTCT TACTGGGGCCAAGGGACTCTG GTCACTGTCTCTGCA (SEQ ID NO: 148) | GATATTGTGATGACTCAGGCT GCACCCTCTATACCTGTCACT CCTGGAGAGTCAGTATCCAT CTCCTGCAGGTCTAGTAAGA GTCTCCTGCATAGTAATGGCA ACACTTACTTGTATTGGTTCC TGCAGAGGCCAGGCCAGTCT CCTCAGCTCCTGATATATCGG ATGTCCAACCTTGCCTCAGGA GTCCCAGACAGGTTCAGTGG CAGTGGGTCAGGAACTGCTT TCACACTGAGAATCAGTAGA GTGGAGGCTGAGGATGTGGG TGTTTATTACTGTATGCAACA TCTAGAATATCCATTCACGTT CGGCTCGGGGACAAAGTTGG AAATAAAA (SEQ ID NO: 149) |
| ACI-7071-809F12-Ab1 | 809F12D8 | CAGGTGCAGCTGAAGGAGTCA GGACCTGGCCTGGTGGCGCCC TCACAGAGCCTGTCCATCACTT GCACTGTCTCTGGGTTTTCGTT AAACAGAAATGGTGTACAGTG GGTTCGCCAGCCTCCAGGAAA GGGTCTGGAGTGGCTGGGAGT AATATGGCCTGGCGGAAGCAC | GATGTTTTGATGACCCAAACT CCCACTCTCCCTGCCTGTCAGT CTTGGAGATCAGGCCTCCATC TCTTGCAGATCTAGTCAGAAC ATTGTACATAGTATTGGAAA CACCTATTTAGAGTGGTACCT GCAGAAACCAGGCCAGTCTC CAAAGCTCCTGATCTACAAA |

TABLE 10-continued

Nucleotide sequences of the Heavy Chain and Light Chain Variable Domains (VH and VL)

| Antibody Name | Hybridoma Code | VH | VL |
|---|---|---|---|
| | | AAATTGTAATTCGGCTCTCATG TCCAGACTGAGCATCAGCAAA GACAACTCCAAGAGTCAAGTT TTCTTAAAAATGAACAGTCTGC ACACTGATGACACAGGCATAT ATTACTGTGCCAGAGTAGGGG GTAACTACGTGTGGGACTATA ATAACTACGCCTGGGGCCAAG GGACTCTGGTCACTGTCTCTGC A (SEQ ID NO: 158) | GTTTCCAACCGATTTTCTGGG GTCCCAGACAGGTTCAGTGG CAGTGGATCAGGGACAGATT TCACACTCAAGATCAGCAGA GTGGAGGCTGAGGATCTGGG AGTTTATTACTGCTTTCAAGG TTCACATGTTCCGTACACGTT CGGAGGGGGGACCAAGCTAG AAATAAGA (SEQ ID NO: 159) |

TABLE 11

Amino acid sequences of the Heavy Chain and Light Chain Variable Domains (VH and VL) and their CDRs

| Antibody name | Hybridoma code | VH | VH CDR 1 | VH CDR 2 | VH CDR 3 | VL | VL CDR 1 | VL CDR 2 | VL CDR 3 |
|---|---|---|---|---|---|---|---|---|---|
| ACI-7069-631B2-Ab1 | 631B2A2 | EVQLQQSG PELVKPGA SVKISCKTS GYTFTEYSI HWVKQSH GESLEWIG GINPDNGG TRYNQKFK GKATLTVD KSSSTAYM DLRSLTSE DSAVYYC ARESWGQ GTTLTVSS (SEQ ID NO: 10) | EYSI H (SEQ ID NO: 11) | GIN PDN GGT RYN QKF KG (SEQ ID NO: 12) | ES | DVVMTQ TPLTLSV TIGQPASI SCKSSQS LLNSDGK TYLNWL LQRPGQS PKRLIYL VSKLDSR IPDRFTG SGSGTDF TLKISRV EAEDLG VYYCWQ GTHFPHT FGSGTKL ELK (SEQ ID NO: 14) | KSS QSL LNS DGK TYL N (SEQ ID NO: 15) | LVS KLD S (SEQ ID NO: 16) | WQ GTH FPH T (SEQ ID NO: 17) |
| ACI-7069-633B12-Ab1 | 633B12C8 | EVQLQQSG PELVKPGA SVKISCKTS GFTFTEYS MHWVKQS HGKSLEWI GGINPNNG GTSYNQKF KGKATLTV DKSSSTAY MELRSLTS EDSAVYYC ARESWGQ GTTLTVSS (SEQ ID NO: 20) | EYS MH (SEQ ID NO: 21) | GIN PNN GGT SYN QKF KG (SEQ ID NO: 22) | ES | DVVMTQ TPLTLSV TIGQPASI SCKSSQS LLHSDGK TYLNWL LQRPGQS PKRLIYL VSKLDSR IPDRFTG SGSGTDF TLKISRV EAEDLG VYYCWQ GTHFPHT FGAGTKL ELK (SEQ ID NO: 24) | KSS QSL LHS DGK TYL N (SEQ ID NO: 25) | LVS KLD S (SEQ ID NO: 16) | WQ GTH FPH T (SEQ ID NO: 27) |
| ACI-7069-634H10-Ab2 | 634H10H7 | EVQLQQSG AELVKPGA SVRLSCTA SGFNIKDT YMIHWVKQ RPEQGLEW IGRIDPANS NTKFDPKF QGKATITS DTSSNTAY | DTY MH (SEQ ID NO: 31) | RID PAN SNT KFD PKF QG (SEQ ID NO: 32) | FYG GSH WYF DV (SEQ ID NO: 33) | DIKMTQS PSSMYAS LGERVTI TCKASQ DIKSYLS WYQHKP WKSPKA LIYYATS LADGVPS RFSGSGS | KAS QDI KSY LS (SEQ ID NO: 35) | YAT SLA D (SEQ ID NO: 36) | LQQ GES PYT (SEQ ID NO: 37) |

TABLE 11-continued

| Antibody name | Hybridoma code | VH | VH CDR 1 | VH CDR 2 | VH CDR 3 | VL | VL CDR 1 | VL CDR 2 | VL CDR 3 |
|---|---|---|---|---|---|---|---|---|---|
| | | LQLSSLTSE DTAVYYC ARFYGGSH WYFDVWG AGTTVTVS S (SEQ ID NO: 30) | | | | GQDYSLT ISSLESDD TATYYCL QQGESPY TFGGGTK LEIK (SEQ ID NO: 34) | | | |
| ACI-7069-636E5-Ab1 | 636E5B8 | EVHLVESG GDLVMPG GSLKLSCA ASGFTFSN YGMSWVR QTPDKRLE WVATISSG GKYINYLD SLKGRFTIS RDNAKNTL YLQMSSLK SEDTAMY YCAKDYG SGWAWFA YWGQGTL VTVSA (SEQ ID NO: 40) | NYG MS (SEQ ID NO: 41) | TISS GGK YIN YLD SLK G (SEQ ID NO: 42) | DYG SGW AWF AY (SEQ ID NO: 43) | QLVLTQS SSASFSL GASAKLT CTLSSQH STYTIEW YQQQPL KPPKYV MELKKD GSHSTGD GIPDRFS GSSSGAD RYLSISNI QPEDEAI YICGVGD TIKEQFV YVFGGG TKVTVL (SEQ ID NO: 44) | TLS SQH STY TIE (SEQ ID NO: 45) | GSH STG D (SEQ ID NO: 46) | GVG DTI KEQ FVY V (SEQ ID NO: 47) |
| ACI-7069-641H1-Ab2 | 641H1E7 | QVQLKESG PGLVAPSQ SLSITCTVS GFSLTNYG VHWVRQP PGKGLEWL GLMWAGG STNYNSAL MSRLSISK DNSKSQVF LKMNSLQT DDTAMYY CVIYRTGF AYWGQGT LVTVSA (SEQ ID NO: 60) | NYG VH (SEQ ID NO: 61) | LM WA GGS TNY NSA LMS (SEQ ID NO: 62) | YRT GFA Y (SEQ ID NO: 63) | DVLMTQ TPLSLPV SLGDQAS ISCRSSQS IVHTIGN TYLEWY LQKPGQS PKLLIYK VSNRFSG VPDRFSG SGSGTDF TLKISRV EAEDLG VYYCFQ GSHVPFT FGSGTKL EIK (SEQ ID NO: 64) | RSS QST VHT IGN TYL E (SEQ ID NO: 65) | KVS NRF S (SEQ ID NO: 66) | FQG SHV PFT (SEQ ID NO: 67) |
| ACI-7069-642A10-ab1 | 642A10B1 1 | QVQLQQPG AELVKPGA SVKLSCKA SGYTFTKY WMHWVK QRPGQGLE WIGEINPSN GRTNYNEK FKSKATLT VDKSSSTA YMQLSSLT SEDSAVYY CARYMDY WGQGTSV TVSS (SEQ ID NO: 70) | KY WM H (SEQ ID NO: 71) | EINP SNG RTN YNE KFK S (SEQ ID NO: 72) | YMD Y (SEQ ID NO: 73) | DVVMTQ TPLTLSV TIGQPASI SCKSSQS LFDRDG KTYLNW LLQRPGQ SPKRLIY LVSKLDS GVPDRFT GSGSGTD FTLKISR VEAEDL GVYYCW QGTHFP WTFGGG TKLEIK (SEQ ID NO: 74) | KSS QSL FDR DGK TYL N (SEQ ID NO: 75) | LVS KLD S (SEQ ID NO: 16) | WQ GTH FPW T (SEQ ID NO: 77) |

TABLE 11-continued

Amino acid sequences of the Heavy Chain and Light Chain Variable Domains (VH and VL) and their CDRs

| Antibody name | Hybridoma code | VH | VH CDR 1 | VH CDR 2 | VH CDR 3 | VL | VL CDR 1 | VL CDR 2 | VL CDR 3 |
|---|---|---|---|---|---|---|---|---|---|
| ACI-7069-642D12-Ab1 | 642D12B4 | EVQLQQSG AELVKPGA SVRLSCTA SGFNIKDP YMHWVRQ RPKQGLE WIGRIDPA DGNTKYDP KFQGKATL TADTSSNV AYLIALSSL TSEDTAVY YCARFYGS SHWYFDV WGAGTTV TVSS (SEQ ID NO: 80) | DPY MH (SEQ ID NO: 81) | RID PAD GNT KYD PKF QG (SEQ ID NO: 82) | FYG SSH WYF DV (SEQ ID NO: 83) | DIKMTQS PSSMYAS LGERVTI TCKASQ DIKRYLS WYQQKP WKSPKIL IYYATSL ADGVPSR FSGTGSG QDYSLTI SSLESDD VATYYC LQQGESP YTFGGGT KLEIK (SEQ ID NO: 84) | KAS QDI KRY LS (SEQ ID NO: 85) | YAT SLA D (SEQ ID NO: 86) | LQQ GES PYT (SEQ ID NO: 87) |
| ACI-7069-646B7-Ab1 | 646B7F7 | QVQLKESG PGLVAPSQ SLSITCTVS GFSLTNFG VHWVRQP PGKGLEWL GIMWAGG STNYNSAL MSRLSISK DNSKSQVF LKMNSLQT DDTAMYY CVIYKTGF AYWGQGT LVTVSA (SEQ ID NO: 100) | NFG VH (SEQ ID NO: 101) | IMW AGG STN YNS ALM S (SEQ ID NO: 102) | YKT GFA Y (SEQ ID NO: 103) | DVLMTQ TPLSLPV SLGDQAS ISCRSSQS IVHAIGN TYLEWY LQKPGQS PKLLIYK VSNRFSG VPDRFSG SGSGTDF TLKISRV EAEDLG VYYCFQ GSHVPFT FGSGTKL EIK (SEQ ID NO: 104) | RSS QSI VHA IGN TYL E (SEQ ID NO: 105) | KVS NRF S (SEQ ID NO: 106) | FQG SHV PFT (SEQ ID NO: 107) |
| ACI-7071-712A6-Ab1 | 712A6B10 | QVQLQQSG AELVKPGT SVKLSCKA SAYTFTEY TIHWIKQK SGQGLEWI GWFHPEN DNIKYNEN FKDKATLT ADRSSSTV YMELSRLT SEDSAVYF CAGTSGYG DYWGQGT TLTVSS (SEQ ID NO: 120) | EYTI H (SEQ ID NO: 121) | WFH PEN DNI KYN ENF KD (SEQ ID NO: 122) | TSG YGD Y (SEQ ID NO: 123) | DVVMTQ IPLTLSITI GQPASIS CKSSQSL LPSDGKT YLNWLL QRPGQSP KRLIYLV SKLDSGV PDRFTGS GSGTDFT LKISRVE ADDLGV YYCWQG THFPPTF GAGTKL ELK (SEQ ID NO: 124) | KSS QSL LPS DGK TYL N (SEQ ID NO: 125) | LVS KLD S (SEQ ID NO: 16) | WQ GTH FPPT (SEQ ID NO: 127) |
| ACI-7071-809D9-Ab2 | 809D9C2 | QVQLQQSG AELVRPGV SVKISCKG SGYKFTDY SMHWVKQ SHTKSLEW IGVISTYYG DTTYNQKF KGKATITV DKSSSTAY MELARLTS EDSAIYYC ATYGNFPA | DYS MH (SEQ ID NO: 141) | VIST YYG DTT YNQ KFK G (SEQ ID NO: 142) | YGN FPA SFS Y (SEQ ID NO: 143) | DIVMTQ AAPSIPV TPGESVSI SCRSSKS LLHSNGN TYLYWF LQRPGQS PQLLIYR MSNLAS GVPDRFS GSGSGTA FTLRISR VEAEDV | RSS KSL LHS NGN TYL Y (SEQ ID NO: 145) | RMS NLA S (SEQ ID NO: 146) | MQH LEY PFT (SEQ ID NO: 147) |

TABLE 11-continued

Amino acid sequences of the Heavy Chain and Light Chain Variable Domains (VH and VL) and their CDRs

| Antibody name | Hybridoma code | VH | VH CDR 1 | VH CDR 2 | VH CDR 3 | VL | VL CDR 1 | VL CDR 2 | VL CDR 3 |
|---|---|---|---|---|---|---|---|---|---|
| | | SFSYWGQG TLVTVSA (SEQ ID NO: 140) | | | | GVYYCM QHLEYPF TFGSGTK LEIK (SEQ ID NO: 144) | | | |
| ACI-7071-809F12-Ab1 | 809F12D8 | QVQLKESG PGLVAPSQ SLSITCTVS GFSLNRNG VQWVRQP PGKGLEWL GVIWPGGS TNCNSALM SRLSISKDN SKSQVFLK MNSLHTD DTGIYYCA RVGGNYV WDYNNYA WGQGTLV TVSA (SEQ ID NO: 150) | RNG VQ (SEQ ID NO: 151) | VIW PGG STN CNS ALM S (SEQ ID NO: 152) | VGG NYV WD YNN YA (SEQ ID NO: 153) | DVLMTQ TPLSLPV SLGDQAS ISCRSSQ NIVHSIG NTYLEW YLQKPG QSPKLLI YKVSNRF SGVPDRF SGSGSGT DFTLKIS RVEAEDL GVYYCF QGSHVP YTFGGGT KLEIR (SEQ ID NO: 154) | RSS QNI VHS IGN TYL E (SEQ ID NO: 155) | KVS NRF S (SEQ ID NO: 156) | FQG SHV PYT (SEQ ID NO: 157) |

Example 10: In Vivo Efficacy of ACI-7069-633B12-Ab1 (IgG2a Variant) in Transgenic Mouse Model of TDP-43 Proteinopathies To evaluate the efficacy of ACI-7069-6331B12-Ab1 (IgG2a variant) in vivo, the ability of ACI-7069-6331B12-Ab1 (IgG2a variant) to reduce TDP-43 pathology in NEFH-tTAxhTDP-43ΔNLS bigenic mice (rNLS8 mice, Walker et al. 2015) was tested. The rNLS8 mice were injected weekly with ACI-7069-6331B12-Ab1 (IgG2a variant) (n=30) or vehicle (n=30) and at the end of dosing, molecular pathological markers such as phosphorylated and/or total insoluble TDP-43 were analyzed.

10.1 Animals

Prior to the initiation of the study, all animals were acclimated to the environment, examined, handled and weighed to ensure adequate health and to minimize non-specific stress associated with experimental manipulation. Mice were kept on chow diet which contained doxycycline (200 mg/kg) during breeding and until 8 weeks of age. At 8 weeks of age the diet was changed to a chow diet not containing doxycycline (DOX) to allow transgene expression. Throughout the study, light/dark cycles (12/12), room temperature (20-23° C.) and relative humidity (around 50%), were kept constant. Chow diet and water were provided ad libitum for the duration of the study. When mice started to display movement difficulties, the diet was changed to wet chow and hydrogel on the cage floor. All behavioral tests were performed during the animal's light cycle phase.

10.2. Compound Administration

On the day of injection, ACI-7069-633B12-Ab1 (IgG2a variant) (60 mg/kg) and vehicle were freshly prepared and administered i.p following a weekly dosing regimen throughout the study.

10.3. Collection of Brains

Brains were divided into two hemispheres. The left hemisphere was dissected to collect cortical brain areas. Mouse cortices and remaining brain tissue were flash-frozen for further biochemical analyses. The remaining right hemispheres were immersion-fixed directly after perfusion for 3 hours at room temperature and collected in freshly prepared 1×PBS containing 4% paraformaldehyde (PFA).

10.4. Imunohistochemistry

Immersion fixed right brain hemispheres were cut sagittally in a uniform, systematic random protocol on a Leica CM1950 cryotome at a section thickness of 10 microns. Systematic random sets of sagittal sections (7 sections from levels 2, 3, 4, 6, 8, 10 and 11 of the brain) per mouse were immunostained for TDP-43 and phosphorylated TDP-43. Iba1 staining was performed to quantify microglial numbers and morphology in brain. Antibody binding was visualized using fluorescently labeled secondary antibodies. Standard negative controls included wild type brain sections as well as sections from transgenic animals without the application of primary antibodies.

10.5. Imaging and Determination of Immunoreactivity

Mounted sections were imaged as a whole on an Axio.Scan Z1 slide scanner driven by ZEN software at 10× magnification using LED (Colibri2) illumination and a sensitive Orca Flash 4.0 monochromatic camera. Brain size was determined using separate delineation of the regions of interest in the cerebral cortex and dorsal striatum. Object density (OD) (in number of objects per $mm^2$) was determined for all markers, labeled area percentage and OD relative to the region of interest size of a second delineation excluding any tissue artifacts (tissue folds, etc.).

10.6. Preparation of Protein Samples from Brain Cortex:

Tissues were thawed on ice and then sonicated in 5× v/w radioimmunoprecipitation assay buffer (RIPA, 50 mM Tris, 150 mM NaCl, 1% IGEPAL CA630, 5 mM EDTA, 0.5% sodium deoxycholate and 0.1% SDS, pH 8.0) containing 1 mM PMSF and a protease-/phosphatase inhibitor cocktail (Roche Applied Science). Samples were centrifuged at 4° C., 100,000 g for 30 minutes and the supernatant was considered as-soluble fraction. The pellet was washed by sonicating with RIPA and the supernatant was discarded. The RIPA-insoluble pellet was sonicated in 2× v/w urea buffer (7M urea, 2M thiourea, 4% CHAPS, and 30 mM Tris, pH8.5) and centrifuged at 22° C., 100,000 g for 30 minutes. This supernatant was considered as the RIPA-insoluble/ urea-soluble fraction. Protein concentrations of the RIPA-soluble fractions were determined using BCA protein assay (Pierce).

10.7. Quantification of Insoluble TDP-43

Total TDP-43 levels in the RIPA insoluble fraction were analyzed by a commercial human TDP-43 AlphaLISA kit (Perkin Elmer, AL387HV).

10.8. Statistical Analysis

IHC and AlphaLISA data are presented as mean±SEM. Statistical differences between vehicle and ACI-7069-633B12-Ab1 (IgG2a variant) treated animals are analyzed by Welch's t-tests and are indicated by asterisks above respective bars (*p<0.05, p<0.01, **p<0.0001). Outliers in histological measurements were excluded either being Grubbs outlier in the group or level (single measurements), or due to technical reasons (image artifacts, tissue folds, etc.).

10.9. Results

Treatment with ACI-7069-633B12-Ab1 (IgG2a variant) reduces phosphorylated TDP-43 and insoluble TDP-43 in rNLS8 mice Overexpression of the DOX repressible form of K82A/R83A/K84A mutant human TDP-43 (hTDP-43ΔNLS) leads to a prominent accumulation and aggregation of TDP-43 in the cytoplasm of neurons in rNLS8 mice model. A pathological hallmark of this model are the deposition of insoluble and phosphorylated TDP-43 inclusions (pTDP-43). These small, spherical cytoplasmic inclusions are solely present in the transgenic animals and are entirely absent in WT or monogenic, transgenic tTA control mice. Moreover, pTDP-43 is widely absent during the 1st week of DOX absence, and accumulated with steep progression during the 3-4-weeks DOX removal (Walker et al., 2015). ACI-7069-633B12-Ab1 (IgG2a variant) treatment led to a statiscally significant reduction in the density of phosphorylated TDP-43 in both striatum and cerebral cortex (FIG. 3A-B) compared to the vehicle treated mice suggesting its functional efficacy in reducing TDP-43 pathology. Striatum and cerebral cortex were chosen for the quantifications due to high expression of transgene in these regions.

Figure 3:
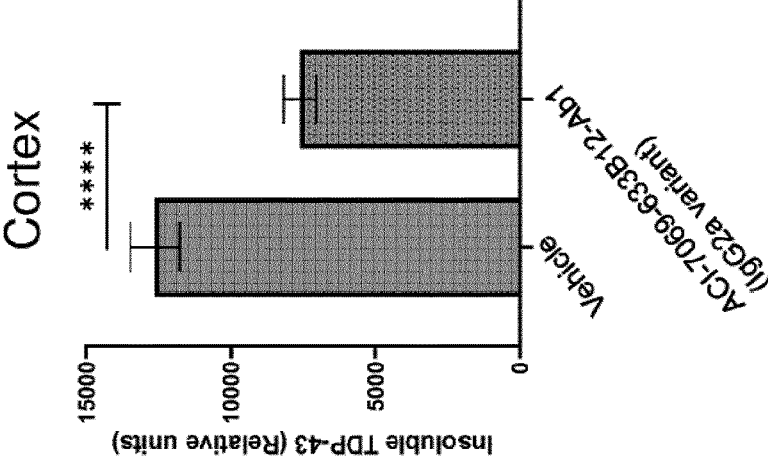
FIG. 3. Density of pTDP-43 immunoreactive objects measured for the vehicle (n=30, grey bars) and ACI-7069-633B12-Ab1 (IgG2a variant) treated mice (n=25, dotted grey bars) are shown for two brain regions: Striatum (A) and Cerebral cortex (B). (C) Insoluble fractions obtained from cortex of left brain hemispheres were quantified for total TDP-43 in vehicle (n=30) and ACI-7069-633B12-Ab1 (IgG2a variant) (n=25) treated groups (*p<0.05, p<0.01, **p<0.0001).
Figure 3:
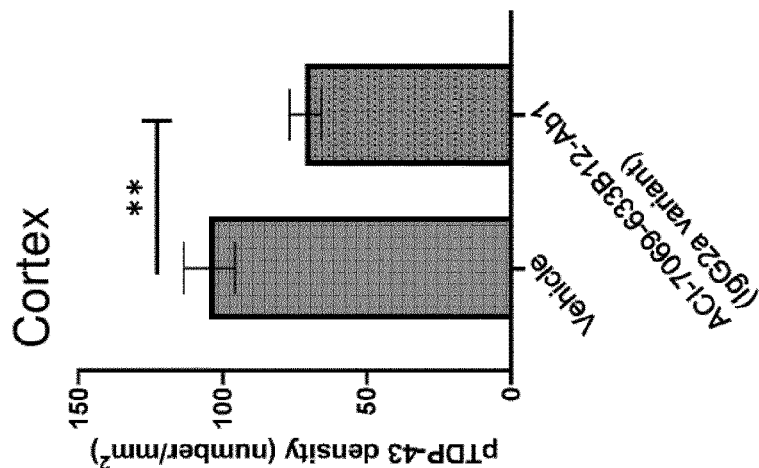

10.10. Treatment with ACI-7069-633B12-Ab1 (IgG2a Variant) Reduces Insoluble TDP-43 in rNLS8 Mice To confirm the reduction of TDP-43 pathology observed in immunohistochemistry readouts, the amount of total insoluble/aggregated TDP-43 in the brain, following biochemical fractionation, was quantified. RIPA-insoluble fractions were prepared from the cortex of left brain hemispheres containing insoluble/aggregated TDP-43. A significant reduction in the amount of insoluble TDP-43 was observed in mice treated with ACI-7069-633B12-Ab1 (IgG2a variant) compared to that of vehicle treated animals (FIG. 3C). This reduction in molecular TDP-43 pathology is in line with the results observed by immunohistochemistry, confirming the efficacy of treatment with ACI-7069-633B12-Ab1 (IgG2a variant). To our knowledge, this is the first time that a peripheral antibody administration ameliorated the formation of TDP-43 pathology in an in vivo model for TDP-43 proteinopathies.

10.11. ACI-7069-633B12-Ab1 (IgG2a Variant) Treatment in rNLS8 Mice Increases Microglial Immunoreactive Area Functional recovery in rNLS8 mice following suppression of transgene expression involves increase in microglial activity. Microglial cell body area increases in this phase and results in clearance of TDP-43 pathology and functional recovery of motor deficits suggesting a therapeutic paradigm in rNLS8 mouse model (Spiller K. J et al., Nature Neuroscience, 2018).

Figure 5:
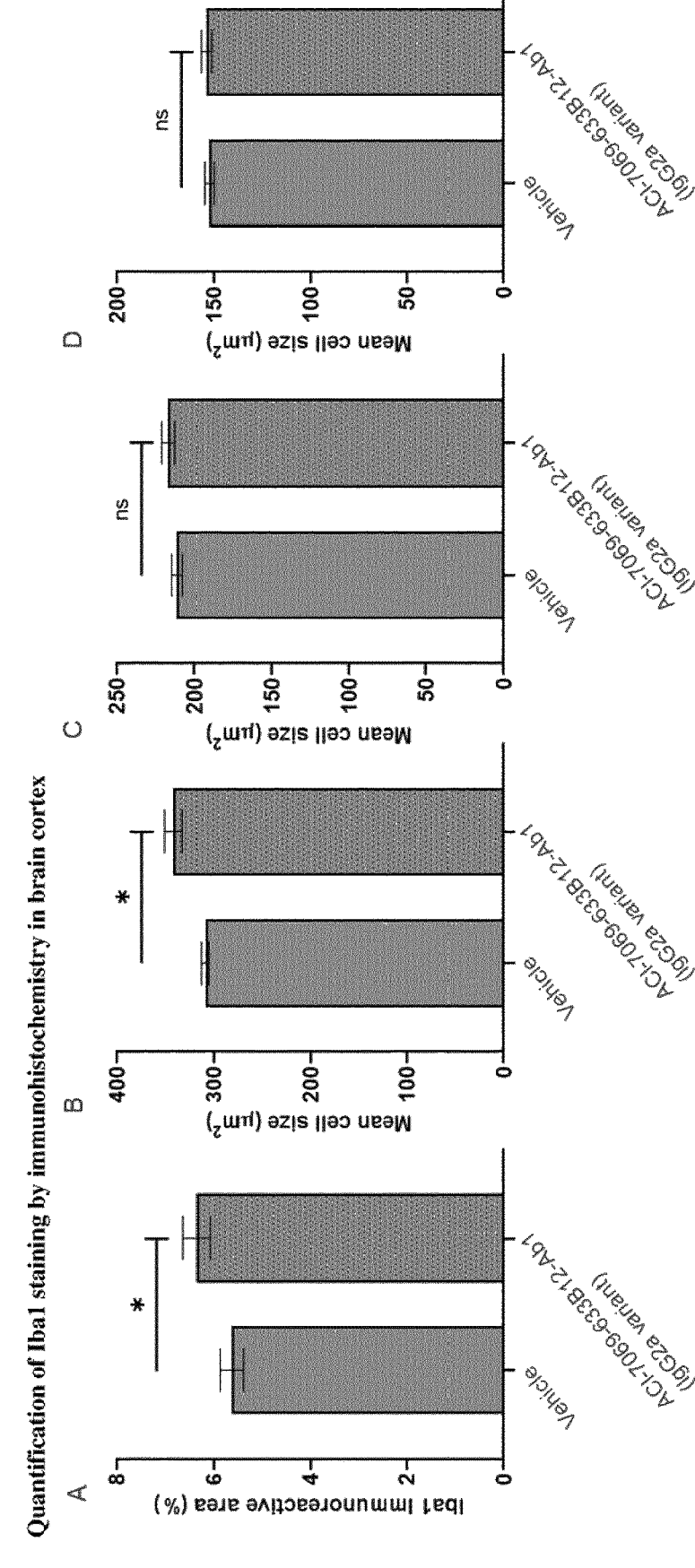
FIG. 5. (A) Iba1 positive immunoreactive area measured for vehicle (n=16, grey bars) and ACI-7069-633B12-Ab1 (IgG2a variant) treated mice (n=16, dotted grey bars) is shown for brain cortex. Error bars represent standard error of mean (SEM). (B-C) Mean microgial cell size measured for vehicle (n=16, grey bars) and ACI-7069-633B12-Ab1 (IgG2a variant) treated mice (n=16, dotted grey bars) is shown for brain cortex. Microglia were classified in three classes based on their morphology: (B) large hypertrophic, (C) small ramifying and (D) ramified resting. Statistical differences between vehicle control and ACI-7069-633B12-Ab1 (IgG2a variant) were analyzed by t-test (*p<0.05).

To evaluate the mode of action of ACI-7069-633B12-Ab1 in reducing TDP-43 pathology in rNLS8 mice, its effect on microglial activation was assessed. Iba1 staining was performed by immunohistochemistry to quantify the number and state of microglia in cerebral cortex of mice. Microgliosis was found in rNLS8 mice at terminal stage (5 weeks off Dox). ACI-7069-633B12-Ab1 treatment significantly increased Iba1 positive immunoreactive area in cortex compared to vehicle-treated control (FIG. 5A). This increase could either result from an increase in number of microglial cells or changes in microglial morphology. For this, first the density of Iba1-positive cells in cortex was evaluated. ACI-7069-633B12-Ab1 treatment did not affect microglial cell density, representing cell number, as compared to vehicle-treated control.

Next, the effect of ACI-7069-633B12-Ab1 on microglial morphology was evaluated. To correlate the increase in Iba1 immunoreactive area to changes in microglial activation states representing morphology, microglia were classified into three states based on their size and morphology (large hypertrophic, small ramifying and ramified resting). A significant increase in mean cell size was seen for large hypertrophic microglia in ACI-7069-633B12-Ab1 (IgG2a variant) treatment compared to vehicle-treated control (FIG. 5B). No significant differences were found in the other two classes of microglia that represent less activated states (FIG. 5C-D). This analysis suggests that the increase in the total Iba1 positive immunoreactive area observed in the ACI-7069-633B12-Ab1 treatment cohort results from changes in morphology reflected in an increase in the microglial cell size and activation state. This suggests that ACI-7069-633B12-Ab1 (IgG2a variant) reduces TDP-43 pathology in this animal model, at least in part, via recruitment and activation of microglia.

Example 11: In Vitro Functionality of ACI-7069-633B12-Ab1 (IgG2a Variant) in Recombinant TDP-43 Aggregation Assay To evaluate functionality of ACI-7069-633B12-Ab1 (IgG2a variant) in vitro, the ability of ACI-7069-633B12-Ab1 (IgG2a variant) to inhibit TDP-43 aggregation was tested. FL TDP-43 was fused at C-terminus to maltose binding protein (MBP) which was separated by a Tobacco Etch Virus (TEV) protease cleavage site and produced recombinantly. Aggregation of 2.5 µM TDP-43-TEV-MBP fusion protein in 30 mM Tris, 150 mM NaCl, pH 7.4 in the presence of 2.5 µM ACI-7069-633B12-Ab1 (IgG2a variant) or isotype control that does not bind to TDP-43 was induced by addition of TEV protease (AcTEV, Invitrogen) and absorbance was monitored in a µclear 96 well plate (Greiner) at 600 nm over 30 h. For evaluation, end points were normalized to isotype control and the percentage of aggregated TDP-43 was calculated for ACI-7069-633B12-

US 12,600,766 B2

83

Figure 4:
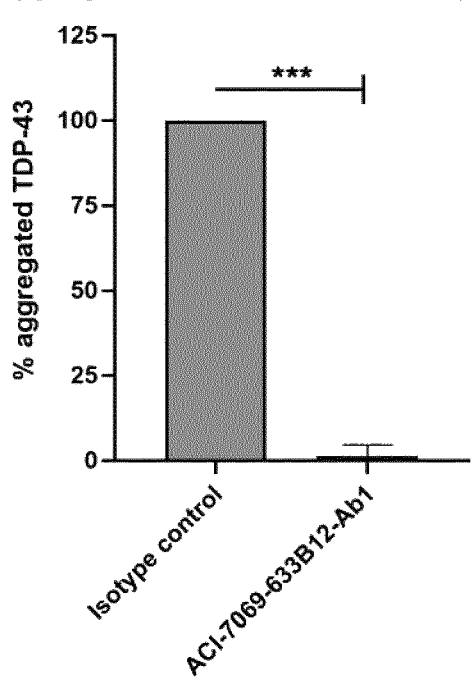
FIG. 4. TDP-43 aggregation induced by TEV cleavage in the presence of ACI-7069-633B12-Ab1 (IgG2a variant) or isotype control is measured by turbidity at 600 nm after 30 h. Endpoints after 30h were normalized to isotype control (grey bar) and % aggregated TDP-43 was calculated for ACI-7069-633B12-Ab1 (dotted grey bar). Mean values±SD are shown for three independent experiments and statistical differences between isotype control and ACI-7069-633B12-Ab1 (IgG2a variant) were analyzed by Welch's t-tests (***p<0.001).

Ab1. The antibody ACI-7069-633B12-Ab1 significantly inhibits TDP-43 aggregation by 98% compared to the isotype control (FIG. 4).

Example 12: Detection and Quantification of TDP-43 in Biofluids with ACI-7069-633B12-Ab1

(IgG2a variant) and ACI-7071-809F12-Ab1 (IgG2a variant) Method: PerkinElmer's bead-based AlphaLISA immunoassay was established using ACI-7069-633B12-Ab1 (IgG2a variant) and ACI-7071-809F12-Ab1 (IgG2a variant). For CSF samples, dilution linearity was established in spike recovery experiments. The concentration of TDP-43 was then measured in diluted CSF samples. Samples were prepared in white Optiplate™-384 microplate and the emission at 615 nm was measured as raw AlphaLISA counts.

Figure 6:
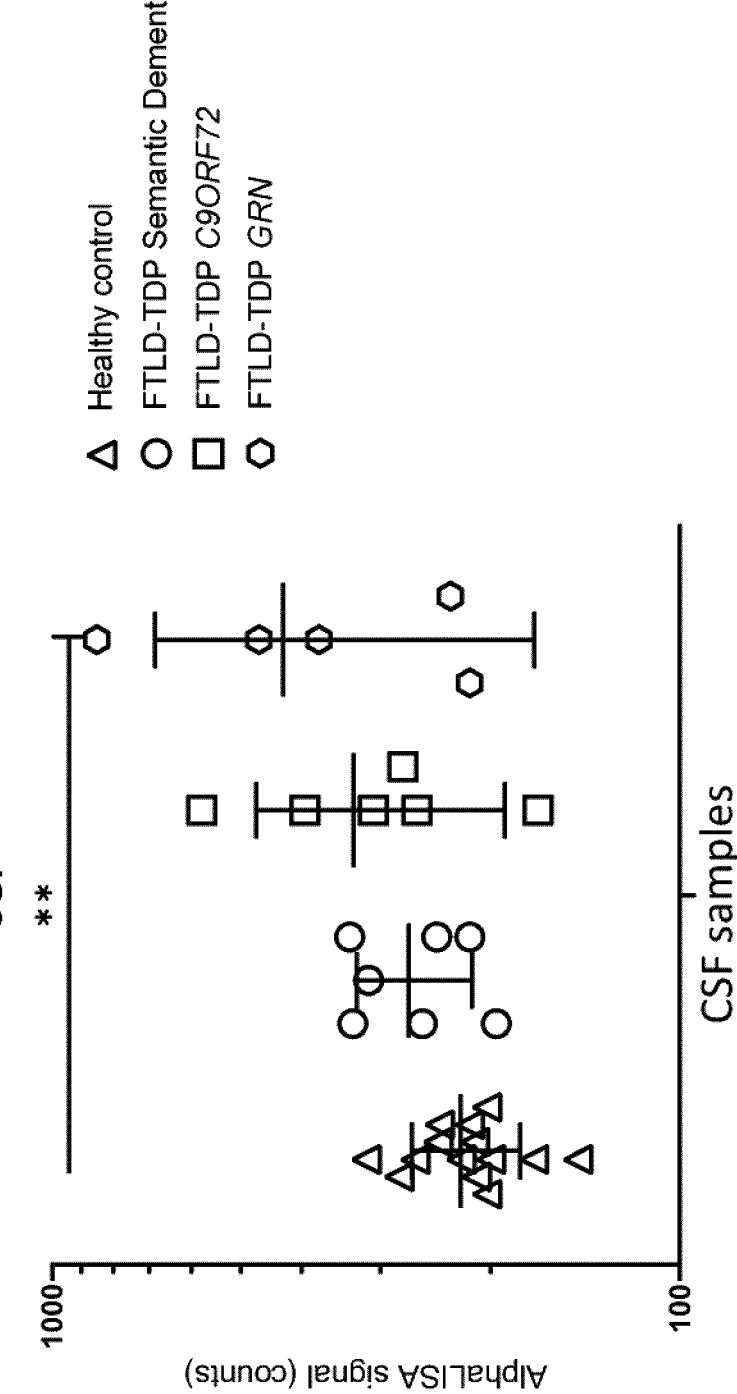
FIG. 6. Quantification of TDP-43 levels in CSF of various FTLD-TDP patients versus healthy controls with AlphaLISA assay with ACI-7069-633B12-Ab1 (IgG2a variant) and ACI-7071-809F12-Ab1 (IgG2a variant). Raw AlphaLISA counts (y-axis) for total TDP-43 obtained for various CSF samples (x-axis). Statistical analysis was performed using a linear mixed model for raw counts using group, experiment, gender and age as fixed factors and individuals as random factor with data from three independent experiments (**p<0.01)

Results: Total TDP-43 in cerebrospinal fluid (CSF) samples from healthy control and FTLD-TDP (Semantic Dementia, C9orf72 or GRN) patients was quantified in this immunoassay (FIG. 6). Relative TDP-43 quantification across various patients' CSF samples from FTLD-TDP patients with GRN mutation showed significantly higher TDP-43 levels compared to healthy controls in three independent experiments (FIG. 6). Relative TDP-43 quantification across various patients' CSF samples from FTLD-TDP patients with C9orf72 mutation and Sementic Dementia also showed higher TDP-43 levels compared to healthy controls in three independent experiments (FIG. 6).

Example 13: Binding to Pathological TDP-43 Assessed by Immunodepletion in FTD Brain Extracts To evaluate the efficacy of antibodies in specifically binding TDP-43 aggregates in native state, immunodepletion experiments in brain extracts with enriched pathological TDP-43 were performed.

Method: Insoluble fractions from FTD type A (FTD-A) postmortem brains were prepared as described in Example 7. Immunodepletion was performed using Dynabeads™ magnetic beads, Protein G (Thermoscientific 10003D). After resuspension in the tube, 130 µl of beads were transferred to a 1.5 ml low binding tube. Beads were rinsed twice with PBS supplemented with 0.05% Tween-20 using a magnet to remove supernatant. Beads were split equally in three different low binding tubes. Antibodies (ACI-7069-633B12-Ab1 (IgG2a isotype), ACI-7069-642D12-Ab1 (IgG2a isotype), mouse IgG2a control) were diluted to 100 µg/ml and 100 µl was added to each tube after removing supernatant (using magnet). Antibody-beads mix was incubated at room temperature for 1 hour. The beads-antibodies complex were washed once with 500 µl PBS-0.05% Tween-20 and once with PBS, then resuspended in 250 µl PBS. Antibody-beads were split into two new tubes (120 µl per tube). Insoluble fractions were thawed on ice and sonicated for 30 seconds at amplitude 30 on ice. Thirty micrograms of brain material was added to each antibody-beads tube after removing supernatant and incubated at 4° C. overnight under continuous rotation. Tubes were placed on the magnet and the supernatant was collected as the immunodepleted fraction. Input and immunodepleted material were further analyzed by Western Blot. Western Blots were performed as described in example 7. Twenty µl of samples were loaded per lane. Immunoblotting was performed using the following antibodies: total TDP-43 (ACI-7069-633B12-Ab1 coupled to DyLight680), pTDP-43 (Biolegend, 829901) used at dilutions of 1:2000 and 1:1000 respectively. Goat anti-rat secondary antibody (catalog number 925-32219) was used at a dilution of 1:10000.

Figure 7:
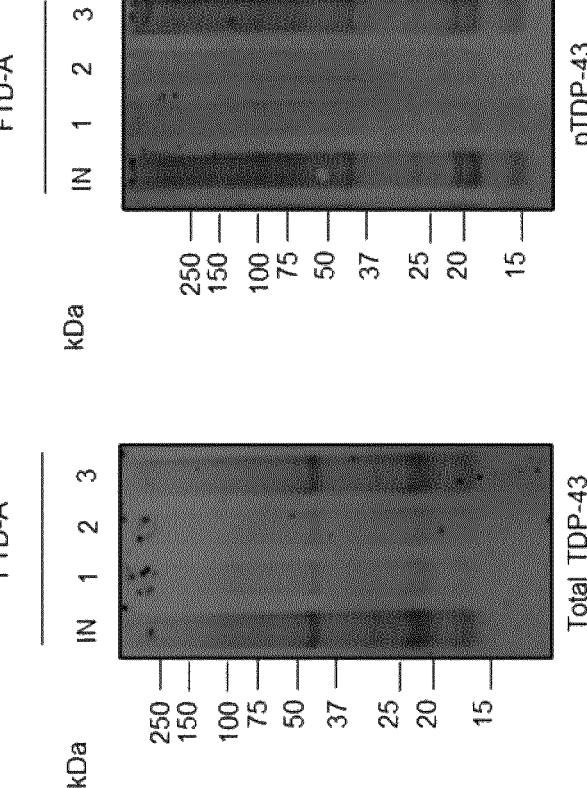
FIG. 7. Immunodepletion of TDP-43 and pTDP-43 by the antibodies ACI-7069-633B12-Ab1 (IgG2a variant) (1), ACI-7069-642D12-Ab1 (IgG2a variant) (2) and mouse IgG2a control (3) from detergent (sarkosyl) insoluble fractions obtained from FTD type A postmortem brain tissues. Immunodepleted fractions 1 to 3 were analyzed by Western Blots using TDP-43 or pTDP-43 specific detection antibodies. IN is for input material (prior to immunodepletion).

Results: ACI-7069-633B12-Ab1 and ACI-7069-642D12-Ab1 were able to specifically bind and deplete TDP-43 and pTDP-43 from sarkosyl insoluble fractions obtained from FTD type A brain tissue compared to isotype control antibody (FIG. 7). This data confirms the property of these antibodies to engage the target in human patients.

REFERENCES

Arai et al., TDP-43 is a component of ubiquitin-positive tau-negative inclusions in frontotemporal lobar degeneration and amyotrophic lateral sclerosis, Biochemical and Biophysical Research Communications 351 (2006) 602-611.

Buratti and Baralle, Nuclear factor TDP-43 can affect selected microRNA levels, FEBS Journal 277 (2010) 2268-2281.

Brettschneider J et al., Spreading of pathology in neurodegenerative diseases: a focus on human studies, Nature Rev. Neuroscience, 2015, 109.

Brettschneider et al., Stages of pTDP-43 pathology in amyotrophic lateral sclerosis, Ann Neurol. 2013 July; 74(1): 20-38.

Charlton, Methods in Molecular Biology, Val. 248 (B. K. C. Lo, ed., Humana Press, Totowa, NJ, 2003), pp. 245-254.

Chowdhury, Methods Mol. Biol. 207:179-196 (2008)

Clynes et al., Fc receptors are required in passive and active immunity to melanoma Proc. Nat'l Acad. sci. USA 95:652-656 (1998)

Cohen et al., An acetylation switch controls TDP-43 function and aggregation propensity, Nat Commun. 6: 5845, 2015.

Cragg, M. S. et al., Complement-mediated lysis by anti-CD20 mAb correlates with segregation into lipid rafts, Blood 101:1045-1052 (2003)

Cragg, M. S. and M. J. Glennie, Antibody specificity controls in vivo effector mechanisms of anti-CD20 reagents, Blood 103:2738-2743 (2004)).

Cunningham and Wells, High-resolution epitope mapping of hGH-receptor interactions by alanine-scanning mutagenesis, (1989) Science, 244: 1081-1085.

Duncan & Winter, The binding site for C1q on IgG, Nature 322:738-40 (1988)

Edelman, G. M. et al., The Covalent Structure of an Entire gammaG Immunoglobulin Molecule, Proc. Natl. Acad. USA, 63, 78-85 (1969)

Feiler et al., TDP-43 is intercellularly transmitted across axon Terminals, J. Cell Biol. Vol. 211 No. 4 897-911.

Feneberg et al., Towards a TDP-43-Based Biomarker for ALS and FTLD, Molecular Neurobiology, 2018; 55(10): 7789-7801.

Gazzano-Santoro et al., Engineered Antibodies with Increased Activity to Recruit Complement, J. Immunol. Methods 202:163 (1996)

Gerngross, Advances in the production of human therapeutic proteins in yeasts and filamentous fungi, Nat. Biotech. 22:1409-1414 (2004).

Gerhardt et al., Methods for General and Molecular Bacteriology, ASM Press (1994).

Golemis, Protein-Protein Interactions: A Molecular Cloning Manual, Cold Spring Harbor Laboratory Press (2002).

Graham et al., Characteristics of a human cell line transformed by DNA from human adenovirus type 5, J. Gen Viral. 36:59 (1977)

Guyer et al., Immunoglobulin binding by mouse intestinal epithelial cell receptors, J. Immunol. 117:587 (1976).

Harlow and Lane, Antibodies: A Laboratory Manual, Cold Spring Harbor Laboratory Press, (1988).

Harlow and Lane, Using Antibodies: A Laboratory Manual, Cold Spring Harbor Laboratory Press, (1999).

Hasegawa et al., Phosphorylated TDP-43 in frontotemporal lobar degeneration and amyotrophic lateral sclerosis, (2008) Annals of Neurology Vol 64 No 1, 60-70.

Hasegawa et al., Prion-like mechanisms and potential therapeutic targets in neurodegenerative disorders, Pharmacol Ther. 2017 April; 172:22-33.

Hellstrom, I. et al., Proc. Nat'l Acad. Sci. USA 83:7059-7063 (1986).

Hellstrom, I et al., Proc. Nat'l Acad. Sci. USA 82:1499-1502 (1985).

Hoogenboom et al., Methods in Molecular Biology 178:1-37 (O'Brien et al., ed., Human Press, Totowa, NJ, (2001).

Howard and Bethell. (2000) Basic Methods in Antibody Production and Characterization, Crc. Pr. Inc.

Idusogie et al., J. Immunol. 164: 4178-4184 (2000).

Ishii et al., Formation and spreading of TDP-43 aggregates in cultured neuronal and glial cells demonstrated by time-lapse imaging, PLoS ONE 12(6): e0179375, 2017.

Jones et al., Replacing the complementarity-determining regions in a human antibody with those from a mouse, Nature 321 (1986), 522-525.

K A et al., TDP-43 is a key player in the clinical features associated with Alzheimer's disease, Acta Neuropathol. 2014; 127(6): 811-824.

K A et al., Staging TDP-43 pathology in Alzheimer's disease Acta Neuropathol. 2014; 127(3): 441-450.

Kam et al., Proc. Natl. Acad. Sci. USA 102: 11600-11605 (2005).

Kanda Y. et al., Bioteehnol. Bioeng., 94(4):680-688 (2006).

Kabat et al., Sequences of Proteins of Immunological Interest, 5th edit. NIH Publication no. 91-3242

U.S. Department of Health and Human Services (1991).

Kim et al., J. Immunol. 24:249 (1994).

Kohler, Nature 256 (1975), 495.

Khor, Proceedings of the American Society of Clinical Oncology Abstract (1997), 847.

Lagier-Tourenne et al., TDP-43 and FUS/TLS: emerging roles in RNA processing and neurodegeneration, Human Molecular Genetics, 2010, Vol. 19, Review Issue 1 R46-R64.

Lagier-Tourenne and Cleveland, Rethinking ALS: the FUS about TDP-43, Cell 136, 2009, 1001-1004.

Le Ber, Genetics of frontotemporal lobar degeneration: an up-date and diagnosis algorithm, Revue Neurologique 169 (2013) 811-819.

Lefkovits, Immunology Methods Manual: The Comprehensive Sourcebook of Techniques; Academic Press (1997).

LoBuglio, Proceedings of the American Society of Clinical Oncology Abstract (1997), 1562.

Li et al., Optimization of humanized IgGs in glycoengineered Pichia pastoris, Nat. Biotech. 24:210-215 (2006).

Mackenzie and Neumann, Molecular neuropathology of frontotemporal dementia: insights into disease mechanisms from postmortem studies, J. Neurochem. (2016) 138 (Suppl. 1), 54-70.

Mather, Establishment and characterization of two distinct mouse testicular epithelial cell lines, Biol. Reprod. 23:243-251 (1980)

Mather et al., Culture of testicular cells in hormone-supplemented serum-free medium, Annals N. Y Aead. Sei. 383:44-68 (1982)

McAleese et al., TDP-43 pathology in Alzheimer's disease, dementia with Lewy bodies and ageing, Brain Pathol. 2017 July; 27(4): 472-479.

Morris, Epitope Mapping Protocols, Methods in Molecular Biology vol. 66(1996) (Humana Press, Totowa, NJ).

Nonaka et al., Prion-like Properties of Pathological TDP-43 Aggregates from Diseased Brains, Cell Reports 4 (2013), 124-134.

Neumann et al., Ubiquitinated TDP-43 in frontotemporal lobar degeneration and amyotrophic lateral sclerosis, Science 314, (2006), 130-133.

Neumann et al., Phosphorylation of S409/410 of TDP-43 is a consistent feature in all sporadic and familial forms of TDP-43 proteinopathies, Acta Neuropathol. (2009) 117: 137-149.

Petkova, S. B. et al., Int'l. Immunol. 18(12):1759-1769 (2006).

Plückthun, The Pharmacology of Monoclonal Antibodies, Rosenburg and Moore eds. Springer-Verlag, N.Y. (1994), 269-315.

Porta S. et al., Patient-derived frontotemporal lobar degeneration brain extracts induce formation and spreading of TDP-43 pathology in vivo Nat. Comm., 2018

Okazaki et al., Fucose depletion from human IgG1 oligosaccharide enhances binding enthalpy and association rate between IgG1 and FcgammaRIIIa. J. Mol. Biol. 336: 1239-1249 (2004).

Presta L G., Antibody engineering, Curr Op Struct Biol 2 (1992), 593-596.

Ravetch and Kinet, Annu. Rev. Immunol. 9:457-492 (1991)

Reichmann, Reshaping human antibodies for therapy, Nature 332 (1998), 323-327.

Remington's Pharmaceutical Sciences 16th edition, Osol, A. Ed. (1980)

Ripka et al., Two Chinese hamster ovary glycosylation mutants affected in the conversion of GDP-mannose to GDP-fucose. Arch. Biochem. Biophys. 249:533-545 (1986).

Sambrook et al., Molecular Cloning: A Laboratory Manual; Cold Spring Harbor Laboratory Press, 2nd edition (1989) and 3rd edition (2001).

Shepherd and Dean (2000), Monoclonal Antibodies: A Practical Approach, Oxford University Press Shields et al., High Resolution Mapping of the Binding Site on Human IgG1 for FcγRI, FcγRII, FcγRIII, and FcRn and Design of IgG1 Variants with Improved Binding to the FcγR, J. Biol. Chem. 9(2): 6591-6604 (2001).

Spiller K. J et al., Microglia-mediated recovery from ALS-relevant motor neuron degeneration in a mouse model of TDP-43 proteinopathy, Nature Neuroscience, 2018

Ticozzi et al., Protein Aggregation and Defective RNA Metabolism as Mechanisms for Motor Neuron Damage, 9(3): 285-296 CNS Neurol. Disord. Drug Targets. 2010, 9(3), 285-296.

Urlaub et al., Isolation of Chinese hamster cell mutants deficient in dihydrofolate reductase activity, Proc. Natl. Acad. cii. USA 77:4216 (1980)

Verhoeyen et al., Reshaping human antibodies: Grafting an antilysozyme activity., Science 239 (1988), 1534-1536.

Walker et al., Neuropathologically mixed Alzheimer's and Lewy body disease: burden of pathological protein aggregates differs between clinical phenotypes, Acta Neuropathol (2015) 129:729-748

Wang et al., TDP-43: an emerging new player in neurodegenerative diseases Trends in Molecular Medicine Vol. 14 No. 11, 2008, 479-485.

Warraich et al., TDP-43: a DNA and RNA binding protein with roles in neurodegenerative diseases, The International Journal of Biochemistry & Cell Biology 42 (2010) 1606-1609. Wright et al., Effect of glycosylation on antibody function. TIBTECH 15:26-32 (1997).

Yamane-Ohnuki et al., Establishment of FUT8 knockout Chinese hamster ovary cells: An ideal host cell line for producing completely defucosylated antibodies with enhanced antibody-dependent cellular cytotoxicity. Biotech. Bioeng. 87: 614 (2004).

Yazaki and Wu, Methods in Molecular Biology, Val. 248 (B. K. C. Lo, ed., Humana Press, Totowa, NJ), pp. 255-268 (2003).

The invention claimed is:

1. A TDP-43 binding molecule, which binds misfolded aggregated TDP-43 and non-aggregated physiological TDP-43 and which comprises:

a) VH-CDR1 comprising the amino acid sequence of SEQ ID NO: 11; VH-CDR2 comprising the amino acid sequence of SEQ ID NO: 12; and VH-CDR3 comprising the amino acid sequence ES (Glu-Ser); VL-CDR1 comprising the amino acid sequence of SEQ ID NO: 15; VL-CDR2 comprising the amino acid sequence of SEQ ID NO: 16; and VL-CDR3 comprising the amino acid sequence of SEQ ID NO: 17; or b) VH-CDR1 comprising the amino acid sequence of SEQ ID NO: 21; VH-CDR2 comprising the amino acid sequence of SEQ ID NO: 22; and VH-CDR3 comprising the amino acid sequence ES (Glu-Ser); VL-CDR1 comprising the amino acid sequence of SEQ ID NO: 25; VL-CDR2 comprising the amino acid sequence of SEQ ID NO: 16; and VL-CDR3 comprising the amino acid sequence of SEQ ID NO: 27; or c) VH-CDR1 comprising the amino acid sequence of SEQ ID NO: 31; VH-CDR2 comprising the amino acid sequence of SEQ ID NO: 32; and VH-CDR3 comprising the amino acid sequence of SEQ ID NO: 33; VL-CDR1 comprising the amino acid sequence of SEQ ID NO: 35; VL-CDR2 comprising the amino acid sequence of SEQ ID NO: 36; and VL-CDR3 comprising the amino acid sequence of SEQ ID NO: 37; or d) VH-CDR1 comprising the amino acid sequence of SEQ ID NO: 41; VH-CDR2 comprising the amino acid sequence of SEQ ID NO: 42; and VH-CDR3 comprising the amino acid sequence of SEQ ID NO: 43; VL-CDR1 comprising the amino acid sequence of SEQ ID NO: 45; VL-CDR2 comprising the amino acid sequence of SEQ ID NO: 46; and VL-CDR3 comprising the amino acid sequence of SEQ ID NO: 47; or e) VH-CDR1 comprising the amino acid sequence of SEQ ID NO: 61; VH-CDR2 comprising the amino acid sequence of SEQ ID NO: 62; and VH-CDR3 comprising the amino acid sequence of SEQ ID NO: 63; VL-CDR1 comprising the amino acid sequence of SEQ ID NO: 65; VL-CDR2 comprising the amino acid sequence of SEQ ID NO: 66; and VL-CDR3 comprising the amino acid sequence of SEQ ID NO: 67; or f) VH-CDR1 comprising the amino acid sequence of SEQ ID NO: 71; VH-CDR2 comprising the amino acid sequence of SEQ ID NO: 72; and VH-CDR3 comprising the amino acid sequence 73; VL-CDR1 comprising the amino acid sequence of SEQ ID NO: 75; VL-CDR2 comprising the amino acid sequence of SEQ ID NO: 16; and VL-CDR3 comprising the amino acid sequence of SEQ ID NO: 77; or g) VH-CDR1 comprising the amino acid sequence of SEQ ID NO: 81; VH-CDR2 comprising the amino acid sequence of SEQ ID NO: 82; and VH-CDR3 comprising the amino acid sequence of SEQ ID NO: 83; VL-CDR1 comprising the amino acid sequence of SEQ ID NO: 85; VL-CDR2 comprising the amino acid sequence of SEQ ID NO: 86; and VL-CDR3 comprising the amino acid sequence of SEQ ID NO: 87; or h) VH-CDR1 comprising the amino acid sequence of SEQ ID NO: 101; VH-CDR2 comprising the amino acid sequence of SEQ ID NO: 102; and VH-CDR3 comprising the amino acid sequence of SEQ ID NO: 103; VL-CDR1 comprising the amino acid sequence of SEQ ID NO: 105; VL-CDR2 comprising the amino acid sequence of SEQ ID NO: 106; and VL-CDR3 comprising the amino acid sequence of SEQ ID NO: 107; or i) VH-CDR1 comprising the amino acid sequence of SEQ ID NO: 121; VH-CDR2 comprising the amino acid sequence of SEQ ID NO: 122; and VH-CDR3 comprising the amino acid sequence of SEQ ID NO: 123; VL-CDR1 comprising the amino acid sequence of SEQ ID NO: 125; VL-CDR2 comprising the amino acid sequence of SEQ ID NO: 16; and VL-CDR3 comprising the amino acid sequence of SEQ ID NO: 127; or j) VH-CDR1 comprising the amino acid sequence of SEQ ID NO: 141; VH-CDR2 comprising the amino acid sequence of SEQ ID NO: 142; and VH-CDR3 comprising the amino acid sequence of SEQ ID NO: 143; VL-CDR1 comprising the amino acid sequence of SEQ ID NO: 145; VL-CDR2 comprising the amino acid sequence of SEQ ID NO: 146; and VL-CDR3 comprising the amino acid sequence of SEQ ID NO: 147; or k) VH-CDR1 comprising the amino acid sequence of SEQ ID NO: 151; VH-CDR2 comprising the amino acid sequence of SEQ ID NO: 152; and VH-CDR3 comprising the amino acid sequence of SEQ ID NO: 153; VL-CDR1 comprising the amino acid sequence of SEQ ID NO: 155; VL-CDR2 comprising the amino acid sequence of SEQ ID NO: 156; and VL-CDR3 comprising the amino acid sequence of SEQ ID NO: 157;

or a humanized antibody or an antigen-binding fragment thereof.

2. The TDP-43 binding molecule of claim 1, which exhibits one or more, up to all of the following characteristics:

a) inhibits the aggregation of TDP-43 protein or fragments thereof, b) blocks TDP-43 cell-to-cell propagation, c) disaggregates TDP-43 aggregates; and d) blocks TDP-43 seeding.

3. The TDP-43 binding molecule of claim 1, which:

(a) reduces TDP-43 pathology in vivo; or (b) reduces levels of aggregated TDP-43 or phosphorylated TDP-43 in vivo.

4. The TDP-43 binding molecule of claim 1, which binds to an epitope within amino acids residues: (a) 181-195, 199-213, 307-321, 352-366, 389-411, 397-411 or 140-200, of human TDP-43 (SEQ ID NO: 1) or to an equivalent epitope in non-human TDP-43; or (b) 183-188, 203-213, 204-208, 204-211, 205-210, 316-323, 358-361, 400-405, 400-406 or 400-412 of human TDP-43 (SEQ ID NO: 1) or to an equivalent epitope in non-human TDP-43.

5. The TDP-43 binding molecule of claim 1, which is an antibody or an antigen-binding fragment thereof.

6. The TDP-43 binding molecule of claim 1, which comprises:

a. a Heavy Chain Variable Region (VH) comprising the sequence of SEQ ID NO: 10 or a Heavy Chain Variable Region (VH) having at least 94%, 95%, 96%, 97%, 98% or 99% sequence identity to the amino acid sequence of SEQ ID NO: 10; and a Light Chain Variable Region (VL) comprising the sequence of SEQ ID NO: 14 or a Light Chain Variable Region (VL) having at least 96%, 97%, 98% or 99% sequence identity to the amino acid sequence of SEQ ID NO: 14; or b. a Heavy Chain Variable Region (VH) comprising the sequence of SEQ ID NO: 20 or a Heavy Chain Variable Region (VH) having at least 98% or 99% sequence identity to the amino acid sequence of SEQ ID NO: 20; and a Light Chain Variable Region (VL) comprising the sequence of SEQ ID NO: 24 or a Light Chain Variable Region (VL) having at least 97%, 98% or 99% sequence identity to the amino acid sequence of SEQ ID NO: 24; or c. a Heavy Chain Variable Region (VH) comprising the sequence of SEQ ID NO: 30 or a Heavy Chain Variable Region (VH) having at least 92%, 93%, 94%, 95%, 96%, 97%, 98%, or 99% sequence identity to the amino acid sequence of SEQ ID NO: 30; and a Light Chain Variable Region (VL) comprising the sequence of SEQ ID NO: 34 or a Light Chain Variable Region (VL)

having at least 98% or 99% sequence identity to the amino acid sequence of SEQ ID NO: 34; or d. a Heavy Chain Variable Region (VH) comprising the sequence of SEQ ID NO: 40 or a Heavy Chain Variable Region (VH) having at least 90%, 91%, 92%, 93%, 94%, 95%, 96%, 97%, 98% or 99% sequence identity to the amino acid sequence of SEQ ID NO: 40; and a Light Chain Variable Region (VL) comprising the sequence of SEQ ID NO: 44; or e. a Heavy Chain Variable Region (VH) comprising the sequence of SEQ ID NO: 60 or a Heavy Chain Variable Region (VH) having at least 94%, 95%, 96%, 97%, 98% or 99% sequence identity to the amino acid sequence of SEQ ID NO: 60; and a Light Chain Variable Region (VL) comprising the sequence of SEQ ID NO: 64 or a Light Chain Variable Region (VL) having at least 99% sequence identity to the amino acid sequence of SEQ ID NO: 64; or f. a Heavy Chain Variable Region (VH) comprising the sequence of SEQ ID NO: 70 or a Heavy Chain Variable Region (VH) having at least 93%, 94%, 95%, 96%, 97%, 98% or 99% sequence identity to the amino acid sequence of SEQ ID NO: 70; and a Light Chain Variable Region (VL) comprising the sequence of SEQ ID NO: 74 or a Light Chain Variable Region (VL) having at least 99% sequence identity to the amino acid sequence of SEQ ID NO: 74; or g. a Heavy Chain Variable Region (VH) comprising the sequence of SEQ ID NO: 80 or a Heavy Chain Variable Region (VH) having at least 90%, 91%, 92%, 93%, 94%, 95%, 96%, 97%, 98% or 99% sequence identity to the amino acid sequence of SEQ ID NO: 80; and a Light Chain Variable Region (VL) comprising the sequence of SEQ ID NO: 84 or a Light Chain Variable Region (VL) having at least 96%, 97%, 98% or 99% sequence identity to the amino acid sequence of SEQ ID NO: 84; or h. a Heavy Chain Variable Region (VH) comprising the sequence of SEQ ID NO: 100 or a Heavy Chain Variable Region (VH) having at least 93%, 94%, 95%, 96%, 97%, 98%, or 99% sequence identity to the amino acid sequence of SEQ ID NO: 100; and a Light Chain Variable Region (VL) comprising the sequence of SEQ ID NO: 104 or a Light Chain Variable Region (VL) having at least 99% sequence identity to the amino acid sequence of SEQ ID NO: 104; or i. a Heavy Chain Variable Region (VH) comprising the sequence of SEQ ID NO: 120 or a Heavy Chain Variable Region (VH) having at least 89%, 90%, 91%, 92%, 93%, 94%, 95%, 96%, 97%, 98% or 99% sequence identity to the amino acid sequence of SEQ ID NO: 120; and a Light Chain Variable Region (VL) comprising the sequence of SEQ ID NO: 124 or a Light Chain Variable Region (VL) having at least 96%, 97%, 98% or 99% sequence identity to the amino acid sequence of SEQ ID NO: 124; or j. a Heavy Chain Variable Region (VH) comprising the sequence of SEQ ID NO: 140 or a Heavy Chain Variable Region (VH) having at least 93%, 94%, 95%, 96%, 97%, 98% or 99% sequence identity to the amino acid sequence of SEQ ID NO: 140; and a Light Chain Variable Region (VL) comprising the sequence of SEQ ID NO: 144; or k. a Heavy Chain Variable Region (VH) comprising the sequence of SEQ ID NO: 150 or a Heavy Chain Variable Region (VH) having at least 85%, 86%, 87%, 88%, 89%, 90%, 91%, 92%, 93%, 94%, 95%, 96%, 97%, 98% or 99% sequence identity to the amino acid sequence of SEQ ID NO: 150; and a Light Chain Variable Region (VL) comprising the sequence of SEQ ID NO: 154 or a Light Chain Variable Region (VL) having at least 99% sequence identity to the amino acid sequence of SEQ ID NO: 154.

7. The TDP-43 binding molecule of claim 1, which comprises:

a. a Heavy Chain Variable Region (VH) comprising the sequence of SEQ ID NO: 10 and a Light Chain Variable Region (VL) comprising the sequence of SEQ ID NO: 14; or b. a Heavy Chain Variable Region (VH) comprising the sequence of SEQ ID NO: 20 and a Light Chain Variable Region (VL) comprising the sequence of SEQ ID NO: 24; or c. a Heavy Chain Variable Region (VH) comprising the sequence of SEQ ID NO: 30 and a Light Chain Variable Region (VL) comprising the sequence of SEQ ID NO: 34; or d. a Heavy Chain Variable Region (VH) comprising the sequence of SEQ ID NO: 40 and a Light Chain Variable Region (VL) comprising the sequence of SEQ ID NO: 44; or e. a Heavy Chain Variable Region (VH) comprising the sequence of SEQ ID NO: 60 and a Light Chain Variable Region (VL) comprising the sequence of SEQ ID NO: 64; or f. a Heavy Chain Variable Region (VH) comprising the sequence of SEQ ID NO: 70 and a Light Chain Variable Region (VL) comprising the sequence of SEQ ID NO: 74; or g. a Heavy Chain Variable Region (VH) comprising the sequence of SEQ ID NO: 80 and a Light Chain Variable Region (VL) comprising the sequence of SEQ ID NO: 84; or h. a Heavy Chain Variable Region (VH) comprising the sequence of SEQ ID NO: 100 and a Light Chain Variable Region (VL) comprising the sequence of SEQ ID NO: 104; or i. a Heavy Chain Variable Region (VH) comprising the sequence of SEQ ID NO: 120 and a Light Chain Variable Region (VL) comprising the sequence of SEQ ID NO: 124; or j. a Heavy Chain Variable Region (VH) comprising the sequence of SEQ ID NO: 140 and a Light Chain Variable Region (VL) comprising the sequence of SEQ ID NO: 144; or k. a Heavy Chain Variable Region (VH) comprising the sequence of SEQ ID NO: 150 and a Light Chain Variable Region (VL) comprising the sequence of SEQ ID NO: 154.

8. The TDP-43 binding molecule of claim 1, which comprises:

a) VH-CDR1 comprising the amino acid sequence of SEQ ID NO: 21; VH-CDR2 comprising the amino acid sequence of SEQ ID NO: 22; and VH-CDR3 comprising the amino acid sequence ES (Glu-Ser); VL-CDR1 comprising the amino acid sequence of SEQ ID NO: 25; VL-CDR2 comprising the amino acid sequence of SEQ ID NO: 16; and VL-CDR3 comprising the amino acid sequence of SEQ ID NO: 27;

b) a Heavy Chain Variable Region (VH) comprising the sequence of SEQ ID NO: 20 and a Light Chain Variable Region (VL) comprising the sequence of SEQ ID NO: 24;

c) VH-CDR1 comprising the amino acid sequence of SEQ ID NO: 81; VH-CDR2 comprising the amino acid sequence of SEQ ID NO: 82; and VH-CDR3 comprising the amino acid sequence of SEQ ID NO: 83; VL-CDR1 comprising the amino acid sequence of SEQ ID NO: 85; VL-CDR2 comprising the amino acid sequence of SEQ ID NO: 86; and VL-CDR3 comprising the amino acid sequence of SEQ ID NO: 87; or d) a Heavy Chain Variable Region (VH) comprising the sequence of SEQ ID NO: 80 and a Light Chain Variable Region (VL) comprising the sequence of SEQ ID NO: 84.

9. The TDP-43 binding molecule of claim 1, which is:

a) a monoclonal antibody or an antigen-binding fragment thereof;

b) a murine, a chimeric, a humanized or a human antibody or an antigen-binding fragment thereof; or c) IgA, IgD, IgE, IgM, IgG1, IgG2, IgG2a, IgG2b, IgG3 or IgG4 antibody or antigen-binding fragment thereof.

10. A pharmaceutical composition comprising the TDP-43 binding molecule of claim 1 and a pharmaceutically acceptable carrier or excipient.

11. A nucleic acid molecule:

i. encoding the TDP-43 binding molecule of claim 1; or ii. comprising a nucleotide sequence set forth as:

a. a Heavy Chain Variable Region (VH) encoding sequence of SEQ ID NO: 18 and a Light Chain Variable Region (VL) encoding sequence of SEQ ID NO: 19; or b. a Heavy Chain Variable Region (VH) encoding sequence of SEQ ID NO: 28 and a Light Chain Variable Region (VL) encoding sequence of SEQ ID NO: 29; or c. a Heavy Chain Variable Region (VH) encoding sequence of SEQ ID NO: 38 and a Light Chain Variable Region (VL) encoding sequence of SEQ ID NO: 39; or d. a Heavy Chain Variable Region (VH) encoding sequence of SEQ ID NO: 48 and a Light Chain Variable Region (VL) encoding sequence of SEQ ID NO: 49; or e. a Heavy Chain Variable Region (VH) encoding sequence of SEQ ID NO: 68 and a Light Chain Variable Region (VL) encoding sequence of SEQ ID NO: 69; or f. a Heavy Chain Variable Region (VH) encoding sequence of SEQ ID NO: 78 and a Light Chain Variable Region (VL) encoding sequence of SEQ ID NO: 79; or g. a Heavy Chain Variable Region (VH) encoding sequence of SEQ ID NO: 88 and a Light Chain Variable Region (VL) encoding sequence of SEQ ID NO: 89; or h. a Heavy Chain Variable Region (VH) encoding sequence of SEQ ID NO: 108 and a Light Chain Variable Region (VL) encoding sequence of SEQ ID NO: 109 or i. a Heavy Chain Variable Region (VH) encoding sequence of SEQ ID NO: 128 and a Light Chain Variable Region (VL) encoding sequence of SEQ ID NO: 129; or j. a Heavy Chain Variable Region (VH) encoding sequence of SEQ ID NO: 148 and a Light Chain Variable Region (VL) encoding sequence of SEQ ID NO: 149; or k. a Heavy Chain Variable Region (VH) encoding sequence of SEQ ID NO: 158 and a Light Chain Variable Region (VL) encoding sequence of SEQ ID NO: 159.

12. A recombinant vector or an expression vector comprising the nucleic acid of claim 11.

13. A host cell comprising the recombinant vector or the expression vector of claim 12.

14. A cell-free expression system containing the expression vector of claim 12.

15. A kit for diagnosis of a disease, disorder or abnormality associated with TDP-43, or a TDP-43 proteinopathy, comprising a TDP-43 binding molecule according to claim 1.

* * * * *

SEQUENCE LISTING

```
<160> NUMBER OF SEQ ID NOS: 159

<210> SEQ ID NO 1
<211> LENGTH: 414
<212> TYPE: PRT
<213> ORGANISM: Artificial Sequence
<220> FEATURE:
<223> OTHER INFORMATION: Q13148

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
            115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
            195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
            275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
```

-continued

```
305                310                315                320

Ala Met Met Ala Ala Ala Gln Ala Ala Leu Gln Ser Ser Trp Gly Met
            325                330                335

Met Gly Met Leu Ala Ser Gln Gln Asn Gln Ser Gly Pro Ser Gly Asn
            340                345                350

Asn Gln Asn Gln Gly Asn Met Gln Arg Glu Pro Asn Gln Ala Phe Gly
        355                360                365

Ser Gly Asn Asn Ser Tyr Ser Gly Ser Asn Ser Gly Ala Ala Ile Gly
        370                375                380

Trp Gly Ser Ala Ser Asn Ala Gly Ser Gly Ser Gly Phe Asn Gly Gly
385                390                395                400

Phe Gly Ser Ser Met Asp Ser Lys Ser Ser Gly Trp Gly Met
            405                410
```

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 111

-continued

```
<212> TYPE: PRT
<213> ORGANISM: Artificial Sequence
<220> FEATURE:
<223> OTHER INFORMATION: ACI-7069-631B2-Ab1 VH

<400> SEQUENCE: 10

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Ser Ile His Trp Val Lys Gln Ser His Gly Glu Ser Leu Glu Trp Ile
        35                  40                  45

Gly Gly Ile Asn Pro Asp Asn Gly Gly Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Glu Ser Trp Gly Gln Gly Thr Thr Leu Thr Val Ser Ser
            100                 105                 110

<210> SEQ ID NO 11
<211> LENGTH: 5
<212> TYPE: PRT
<213> ORGANISM: Artificial Sequence
<220> FEATURE:
<223> OTHER INFORMATION: ACI-7069-631B2-Ab1 VH CDR1

<400> SEQUENCE: 11

Glu Tyr Ser Ile His
1               5

<210> SEQ ID NO 12
<211> LENGTH: 17
<212> TYPE: PRT
<213> ORGANISM: Artificial Sequence
<220> FEATURE:
<223> OTHER INFORMATION: ACI-7069-631B2-Ab1 VH CDR2

<400> SEQUENCE: 12

Gly Ile Asn Pro Asp Asn Gly Gly Thr Arg Tyr Asn Gln Lys Phe Lys
1               5                   10                  15

Gly

<210> SEQ ID NO 13

<400> SEQUENCE: 13

000

<210> SEQ ID NO 14
<211> LENGTH: 112
<212> TYPE: PRT
<213> ORGANISM: Artificial Sequence
<220> FEATURE:
<223> OTHER INFORMATION: ACI-7069-631B2-AB1 VL

<400> SEQUENCE: 14

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asn Ser
            20                  25                  30
```

-continued

```
Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Arg Ile Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Ser Gly Thr Lys Leu Glu Leu Lys
            100                 105                 110

<210> SEQ ID NO 15
<211> LENGTH: 16
<212> TYPE: PRT
<213> ORGANISM: Artificial Sequence
<220> FEATURE:
<223> OTHER INFORMATION: ACI-7069-631B2-AB1 VL CDR1

<400> SEQUENCE: 15

Lys Ser Ser Gln Ser Leu Leu Asn Ser Asp Gly Lys Thr Tyr Leu Asn
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: ACI-7069-631B2-AB1 VL CDR2

<400> SEQUENCE: 16

Leu Val Ser Lys Leu Asp Ser
1               5

<210> SEQ ID NO 17
<211> LENGTH: 9
<212> TYPE: PRT
<213> ORGANISM: Artificial Sequence
<220> FEATURE:
<223> OTHER INFORMATION: ACI-7069-631B2-Ab1 VL CDR3

<400> SEQUENCE: 17

Trp Gln Gly Thr His Phe Pro His Thr
1               5

<210> SEQ ID NO 18
<211> LENGTH: 333
<212> TYPE: DNA
<213> ORGANISM: Artificial Sequence
<220> FEATURE:
<223> OTHER INFORMATION: ACI-7069-631B2-Ab1 VH

<400> SEQUENCE: 18
gaggtccagc tgcaacagtc tggacctgaa ctggtgaagc ctggggcttc agtgaagata      60
tcctgcaaga cttctggata cacattcact gaatactcca tacactgggt gaaacagagc     120
catggagaga gccttgagtg gattggaggt attaatcctg acaatggtgg tactaggtac     180
aaccagaagt tcaagggcaa ggcgacattg actgtagaca gtcctccag cacagcctac      240 atggacctcc gcagcctgac atctgaggat tctgcagttt attattgtgc aagagagtcc     300
tggggccaag gcaccactct cacagtctcc tct                                  333

<210> SEQ ID NO 19
<211> LENGTH: 336
```

<212> TYPE: DNA
<213> ORGANISM: Artificial Sequence
<220> FEATURE:
<223> OTHER INFORMATION: ACI-7069-631B2-Ab1 VL

<400> SEQUENCE: 19
gatgttgtga tgacccagac tccactcact ttgtcggtta ccattggaca accagcctcc     60
atctcttgca agtcaagtca gagcctctta aatagtgatg aaagacata tttgaattgg    120 ttgttacaga ggccaggcca gtctccaaag cgcctaatct atctggtgtc taaactggac    180
tctagaatcc ctgacaggtt cactggcagt ggatcaggga cagatttcac actgaaaatc    240
agcagagtgg aggctgagga tttgggagtt tattattgct ggcaaggtac acattttcct    300
cacacgttcg gttctgggac caagctggag ctgaaa                              336

<210> SEQ ID NO 20
<211> LENGTH: 111
<212> TYPE: PRT
<213> ORGANISM: Artificial Sequence
<220> FEATURE:
<223> OTHER INFORMATION: ACI-7069-633B12-Ab1 VH

<400> SEQUENCE: 20

Glu Val Gln Leu Gln Gln Ser Gly Pro Glu Leu Val Lys Pro Gly Ala
1               5                   10                  15

Ser Val Lys Ile Ser Cys Lys Thr Ser Gly Phe Thr Phe Thr Glu Tyr
            20                  25                  30

Ser Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Ser Trp Gly Gln Gly Thr Thr Leu Thr Val Ser Ser
            100                 105                 110

<210> SEQ ID NO 21
<211> LENGTH: 5
<212> TYPE: PRT
<213> ORGANISM: Artificial Sequence
<220> FEATURE:
<223> OTHER INFORMATION: ACI-7069-633B12-Ab1 VH CDR1

<400> SEQUENCE: 21

Glu Tyr Ser Met His
1               5

<210> SEQ ID NO 22
<211> LENGTH: 17
<212> TYPE: PRT
<213> ORGANISM: Artificial Sequence
<220> FEATURE:
<223> OTHER INFORMATION: ACI-7069-633B12-Ab1 VH CDR2

<400> SEQUENCE: 22

Gly Ile Asn Pro Asn Asn Gly Gly Thr Ser Tyr Asn Gln Lys Phe Lys
1               5                   10                  15

Gly

-continued

```
<210> SEQ ID NO 23

<400> SEQUENCE: 23

000

<210> SEQ ID NO 24
<211> LENGTH: 112
<212> TYPE: PRT
<213> ORGANISM: Artificial Sequence
<220> FEATURE:
<223> OTHER INFORMATION: ACI-7069-633B12-Ab1 VL

<400> SEQUENCE: 24

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Arg Ile Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Ala Gly Thr Lys Leu Glu Leu Lys
            100                 105                 110

<210> SEQ ID NO 25
<211> LENGTH: 16
<212> TYPE: PRT
<213> ORGANISM: Artificial Sequence
<220> FEATURE:
<223> OTHER INFORMATION: ACI-7069-633B12-Ab1 VL CDR1

<400> SEQUENCE: 25

Lys Ser Ser Gln Ser Leu Leu His Ser Asp Gly Lys Thr Tyr Leu Asn
1               5                   10                  15

<210> SEQ ID NO 26

<400> SEQUENCE: 26

000

<210> SEQ ID NO 27
<211> LENGTH: 9
<212> TYPE: PRT
<213> ORGANISM: Artificial Sequence
<220> FEATURE:
<223> OTHER INFORMATION: ACI-7069-633B12-Ab1 VL CDR3

<400> SEQUENCE: 27

Trp Gln Gly Thr His Phe Pro His Thr
1               5

<210> SEQ ID NO 28
<211> LENGTH: 333
<212> TYPE: DNA
<213> ORGANISM: Artificial Sequence
<220> FEATURE:
<223> OTHER INFORMATION: ACI-7069-633B12-Ab1 VH

<400> SEQUENCE: 28
```

-continued

```
gaggtccagc tgcaacagtc tggacctgaa ctggtgaagc ctgggggcttc agtgaagata      60 tcctgcaaga cttctggatt cacattcact gaatactcca tgcactgggt gaaacagagc     120
catggaaaga gccttgagtg gattggaggt attaatccta caatggtgg tactagctac      180 aaccagaagt tcaagggcaa ggccacattg actgtagaca gtcctccag cacagcctac      240 atggagctcc gcagcctaac atctgaggat tctgcagtct attactgtgc aagagagtcc     300 tgggggccaag gcaccactct cacagtctcc tca                                  333
```

<210> SEQ ID NO 29
<211> LENGTH: 336
<212> TYPE: DNA
<213> ORGANISM: Artificial Sequence
<220> FEATURE:
<223> OTHER INFORMATION: ACI-7069-633B12-Ab1 VL

<400> SEQUENCE: 29

```
gatgttgtga tgacccagac tccactcact ttgtcggtta ccattggaca accagcctcc      60
atctcttgca agtcaagtca gagcctctta catagtgatg aaagacata tttgaattgg      120 ttgttacaga ggccaggcca gtctccaaag cgcctaatct atctggtgtc taaactggac     180
tctagaatcc ctgacaggtt cactggcagt ggatcaggga cagatttcac actgaaaatc     240
agcagagtgg aggctgagga tttgggagtt tattattgct ggcaaggtac acattttcct     300
cacacgttcg gtgctgggac caagctggag ctgaaa                                336
```

<210> SEQ ID NO 30
<211> LENGTH: 120
<212> TYPE: PRT
<213> ORGANISM: Artificial Sequence
<220> FEATURE:
<223> OTHER INFORMATION: ACI-7069-634H10-Ab2 VH

<400> SEQUENCE: 30

```
Glu Val Gln Leu Gln Gln Ser Gly Ala Glu Leu Val Lys Pro Gly Ala
1               5                   10                  15

Ser Val Arg Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Ser Asn Thr Lys Phe Asp Pro Lys Phe
    50                  55                  60

Gln Gly Lys Ala Thr Ile Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Phe Tyr Gly Gly Ser His Trp Tyr Phe Asp Val Trp Gly Ala
            100                 105                 110

Gly Thr Thr Val Thr Val Ser Ser
        115                 120
```

<210> SEQ ID NO 31
<211> LENGTH: 5
<212> TYPE: PRT
<213> ORGANISM: Artificial Sequence
<220> FEATURE:
<223> OTHER INFORMATION: ACI-7069-634H10-Ab2 VH CDR1

<400> SEQUENCE: 31

```
Asp Thr Tyr Met His
1               5

<210> SEQ ID NO 32
<211> LENGTH: 17
<212> TYPE: PRT
<213> ORGANISM: Artificial Sequence
<220> FEATURE:
<223> OTHER INFORMATION: ACI-7069-634H10-Ab2 VH CDR2

<400> SEQUENCE: 32

Arg Ile Asp Pro Ala Asn Ser Asn Thr Lys Phe Asp Pro Lys Phe Gln
1               5                   10                  15

Gly

<210> SEQ ID NO 33
<211> LENGTH: 11
<212> TYPE: PRT
<213> ORGANISM: Artificial Sequence
<220> FEATURE:
<223> OTHER INFORMATION: ACI-7069-634H10-Ab2 VH CDR3

<400> SEQUENCE: 33

Phe Tyr Gly Gly Ser His Trp Tyr Phe Asp Val
1               5                   10

<210> SEQ ID NO 34
<211> LENGTH: 107
<212> TYPE: PRT
<213> ORGANISM: Artificial Sequence
<220> FEATURE:
<223> OTHER INFORMATION: ACI-7069-634H10-Ab2 VL

<400> SEQUENCE: 34

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln His Lys Pro Trp Lys Ser Pro Lys Ala Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln Gln Gly Glu Ser Pro Tyr
                85                  90                  95

Thr Phe Gly Gly Gly Thr Lys Leu Glu Ile Lys
            100                 105

<210> SEQ ID NO 35
<211> LENGTH: 11
<212> TYPE: PRT
<213> ORGANISM: Artificial Sequence
<220> FEATURE:
<223> OTHER INFORMATION: ACI-7069-634H10-Ab2 VL CDR1

<400> SEQUENCE: 35

Lys Ala Ser Gln Asp Ile Lys Ser Tyr Leu Ser
1               5                   10

<210> SEQ ID NO 36
<211> LENGTH: 7
<212> TYPE: PRT
```

<213> ORGANISM: Artificial Sequence
<220> FEATURE:
<223> OTHER INFORMATION: ACI-7069-634H10-Ab2 VL CDR2

<400> SEQUENCE: 36

Tyr Ala Thr Ser Leu Ala Asp
1               5

<210> SEQ ID NO 37
<211> LENGTH: 9
<212> TYPE: PRT
<213> ORGANISM: Artificial Sequence
<220> FEATURE:
<223> OTHER INFORMATION: ACI-7069-634H10-Ab2 VL CDR3

<400> SEQUENCE: 37

Leu Gln Gln Gly Glu Ser Pro Tyr Thr
1               5

<210> SEQ ID NO 38
<211> LENGTH: 360
<212> TYPE: DNA
<213> ORGANISM: Artificial Sequence
<220> FEATURE:
<223> OTHER INFORMATION: ACI-7069-634H10-Ab2 VH

<400> SEQUENCE: 38
gaggttcagc tgcagcagtc tggggcagag cttgtgaagc caggggcctc agtcaggttg      60
tcctgcacag cttctggctt caacattaaa gacacctata tgcactgggt gaagcagagg     120
cctgaacagg gcctggaatg gattggaagg attgatcctg cgaatagtaa tactaaattt     180
gacccgaagt tccagggcaa ggccactata acatcagaca catcctccaa cacagcctac     240
ctgcagctca gcagcctgac atctgaggac actgccgtct attactgtgc tagattctac     300
ggtggtagcc actggtactt cgatgtctgg ggcgcaggga ccacggtcac cgtctcctca     360

<210> SEQ ID NO 39
<211> LENGTH: 321
<212> TYPE: DNA
<213> ORGANISM: Artificial Sequence
<220> FEATURE:
<223> OTHER INFORMATION: ACI-7069-634H10-Ab2 VL

<400> SEQUENCE: 39
gacatcaaga tgacccagtc tccatcctcc atgtatgcat cgttgggaga gagagtcact      60
atcacttgca aggcgagtca ggacattaaa agctatttaa gctggtacca gcataaacca     120
tggaaatctc ctaaggccct gatctattat gctacaagct ggcagatgg ggtcccatca      180 agattcagtg gcagtggatc tgggcaagat tattctctaa ccatcagcag cctggagtct     240
gacgatacag caacttacta ctgtctacag caaggtgaga gcccgtacac gttcggaggg     300
gggaccaagc tggaaataaa a                                              321

<210> SEQ ID NO 40
<211> LENGTH: 120
<212> TYPE: PRT
<213> ORGANISM: Artificial Sequence
<220> FEATURE:
<223> OTHER INFORMATION: ACI-7069-636E5-Ab1 VH

<400> SEQUENCE: 40

Glu Val His Leu Val Glu Ser Gly Gly Asp Leu Val Met Pro Gly Gly
1               5                   10                  15

```
Ser Leu Lys Leu Ser Cys Ala Ala Ser Gly Phe Thr Phe Ser Asn Tyr
            20              25                  30

Gly Met Ser Trp Val Arg Gln Thr Pro Asp Lys Arg Leu Glu Trp Val
        35                  40                  45

Ala Thr Ile Ser Ser Gly Gly Lys Tyr Ile Asn Tyr Leu Asp Ser Leu
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Lys Asp Tyr Gly Ser Gly Trp Ala Trp Phe Ala Tyr Trp Gly Gln
            100                 105                 110

Gly Thr Leu Val Thr Val Ser Ala
        115                 120

<210> SEQ ID NO 41
<211> LENGTH: 5
<212> TYPE: PRT
<213> ORGANISM: Artificial Sequence
<220> FEATURE:
<223> OTHER INFORMATION: ACI-7069-636E5-Ab1 VH CDR1

<400> SEQUENCE: 41

Asn Tyr Gly Met Ser
1               5

<210> SEQ ID NO 42
<211> LENGTH: 17
<212> TYPE: PRT
<213> ORGANISM: Artificial Sequence
<220> FEATURE:
<223> OTHER INFORMATION: ACI-7069-636E5-Ab1 VH CDR2

<400> SEQUENCE: 42

Thr Ile Ser Ser Gly Gly Lys Tyr Ile Asn Tyr Leu Asp Ser Leu Lys
1               5                   10                  15

Gly

<210> SEQ ID NO 43
<211> LENGTH: 11
<212> TYPE: PRT
<213> ORGANISM: Artificial Sequence
<220> FEATURE:
<223> OTHER INFORMATION: ACI-7069-636E5-Ab1 VH CDR3

<400> SEQUENCE: 43

Asp Tyr Gly Ser Gly Trp Ala Trp Phe Ala Tyr
1               5                   10

<210> SEQ ID NO 44
<211> LENGTH: 115
<212> TYPE: PRT
<213> ORGANISM: Artificial Sequence
<220> FEATURE:
<223> OTHER INFORMATION: ACI-7069-636E5-Ab1 VL

<400> SEQUENCE: 44

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Thr
            20                  25                  30

Ile Glu Trp Tyr Gln Gln Gln Pro Leu Lys Pro Pro Lys Tyr Val Met
```

-continued

```
            35              40              45
Glu Leu Lys Lys Asp Gly Ser His Ser Thr Gly Asp Gly Ile Pro Asp
    50              55              60

Arg Phe Ser Gly Ser Ser Ser Gly Ala Asp Arg Tyr Leu Ser Ile Ser
65              70              75              80

Asn Ile Gln Pro Glu Asp Glu Ala Ile Tyr Ile Cys Gly Val Gly Asp
                85              90              95

Thr Ile Lys Glu Gln Phe Val Tyr Val Phe Gly Gly Gly Thr Lys Val
            100             105             110

Thr Val Leu
        115
```

<210> SEQ ID NO 45
<211> LENGTH: 12
<212> TYPE: PRT
<213> ORGANISM: Artificial Sequence
<220> FEATURE:
<223> OTHER INFORMATION: ACI-7069-636E5-Ab1 VL CDR1

<400> SEQUENCE: 45

```
Thr Leu Ser Ser Gln His Ser Thr Tyr Thr Ile Glu
1               5               10
```

<210> SEQ ID NO 46
<211> LENGTH: 7
<212> TYPE: PRT
<213> ORGANISM: Artificial Sequence
<220> FEATURE:
<223> OTHER INFORMATION: ACI-7069-636E5-Ab1 VL CDR2

<400> SEQUENCE: 46

```
Gly Ser His Ser Thr Gly Asp
1               5
```

<210> SEQ ID NO 47
<211> LENGTH: 13
<212> TYPE: PRT
<213> ORGANISM: Artificial Sequence
<220> FEATURE:
<223> OTHER INFORMATION: ACI-7069-636E5-Ab1 VL CDR3

<400> SEQUENCE: 47

```
Gly Val Gly Asp Thr Ile Lys Glu Gln Phe Val Tyr Val
1               5               10
```

<210> SEQ ID NO 48
<211> LENGTH: 360
<212> TYPE: DNA
<213> ORGANISM: Artificial Sequence
<220> FEATURE:
<223> OTHER INFORMATION: ACI-7069-636E5-Ab1 VH

<400> SEQUENCE: 48

```
gaggtacatc tggtggagtc tgggggagac ttagtgatgc ctggagggtc cctgaagctc        60
tcctgtgcag cctctggatt cactttcagt aactatggca tgtcttgggt tcgccagact       120
ccagacaaga ggctggagtg ggtcgcaacc attagtagtg gtggtaaata tatcaactac       180
ttagacagtt tgaaggggcg attcaccatc tccagagaca atgccaagaa caccctatac       240
ctgcaaatga gcagtctgaa gtctgaggat acagccatgt attactgtgc aaaagactac       300
ggtagtggct gggcctggtt tgcttactgg ggccaaggga ctctggtcac tgtctctgca       360
```

<210> SEQ ID NO 49
<211> LENGTH: 345
<212> TYPE: DNA
<213> ORGANISM: Artificial Sequence
<220> FEATURE:
<223> OTHER INFORMATION: ACI-7069-636E5-Ab1 VL

<400> SEQUENCE: 49
caacttgtgc tcactcagtc atcttcagcc tctttctccc tgggagcctc agcaaaactc         60
acgtgcacct tgagtagtca gcacagtacg tacaccattg aatggtatca gcaacagcca        120
ctcaagcctc ctaagtatgt gatggagctt aagaaagatg gaagccacag cacaggtgat        180
gggattcctg atcgcttctc tggatccagc tctggtgctg atcgctacct tagcattcc         240 aacatccagc ctgaagatga agcaatatac atctgtggtg tgggtgatac aattaaggaa        300
caatttgtgt atgttttcgg cggtggaacc aaggtcactg tccta                        345

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

-continued

```
<400> SEQUENCE: 58

000

<210> SEQ ID NO 59

<400> SEQUENCE: 59

000

<210> SEQ ID NO 60
<211> LENGTH: 115
<212> TYPE: PRT
<213> ORGANISM: Artificial Sequence
<220> FEATURE:
<223> OTHER INFORMATION: ACI-7069-641H1-Ab2 VH

<400> SEQUENCE: 60

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Pro Pro Gly Lys Gly Leu Glu Trp Leu
        35                  40                  45

Gly Leu Met Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Val
                85                  90                  95

Ile Tyr Arg Thr Gly Phe Ala Tyr Trp Gly Gln Gly Thr Leu Val Thr
            100                 105                 110

Val Ser Ala
        115

<210> SEQ ID NO 61
<211> LENGTH: 5
<212> TYPE: PRT
<213> ORGANISM: Artificial Sequence
<220> FEATURE:
<223> OTHER INFORMATION: ACI-7069-641H1-Ab2 VH CDR1

<400> SEQUENCE: 61

Asn Tyr Gly Val His
1               5

<210> SEQ ID NO 62
<211> LENGTH: 16
<212> TYPE: PRT
<213> ORGANISM: Artificial Sequence
<220> FEATURE:
<223> OTHER INFORMATION: ACI-7069-641H1-Ab2 VH CDR2

<400> SEQUENCE: 62

Leu Met Trp Ala Gly Gly Ser Thr Asn Tyr Asn Ser Ala Leu Met Ser
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: ACI-7069-641H1-Ab2 VH CDR3
```

<400> SEQUENCE: 63

Tyr Arg Thr Gly Phe Ala Tyr
1               5

<210> SEQ ID NO 64
<211> LENGTH: 112
<212> TYPE: PRT
<213> ORGANISM: Artificial Sequence
<220> FEATURE:
<223> OTHER INFORMATION: ACI-7069-641H1-Ab2 VL

<400> SEQUENCE: 64

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Thr
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 65
<211> LENGTH: 16
<212> TYPE: PRT
<213> ORGANISM: Artificial Sequence
<220> FEATURE:
<223> OTHER INFORMATION: ACI-7069-641H1-Ab2 VL CDR1

<400> SEQUENCE: 65

Arg Ser Ser Gln Ser Ile Val His Thr Ile Gly Asn Thr Tyr Leu Glu
1               5                   10                  15

<210> SEQ ID NO 66
<211> LENGTH: 7
<212> TYPE: PRT
<213> ORGANISM: Artificial Sequence
<220> FEATURE:
<223> OTHER INFORMATION: ACI-7069-641H1-Ab2 VL CDR2

<400> SEQUENCE: 66

Lys Val Ser Asn Arg Phe Ser
1               5

<210> SEQ ID NO 67
<211> LENGTH: 9
<212> TYPE: PRT
<213> ORGANISM: Artificial Sequence
<220> FEATURE:
<223> OTHER INFORMATION: ACI-7069-641H1-Ab2 VL CDR3

<400> SEQUENCE: 67

Phe Gln Gly Ser His Val Pro Phe Thr
1               5

<210> SEQ ID NO 68
<211> LENGTH: 345

-continued

```
<212> TYPE: DNA
<213> ORGANISM: Artificial Sequence
<220> FEATURE:
<223> OTHER INFORMATION: ACI-7069-641H1-Ab2 VH

<400> SEQUENCE: 68
caggtgcagc tgaaggagtc aggacctggc ctggtggcgc cctcacagag cctgtccatc     60
acttgtactg tctctgggtt ttcattaacc aactatggtg tacactgggt tcgccagcct    120
ccaggaaagg gtctggagtg gctgggacta atgtgggctg tggaagcac aaattataat     180 tcggctctca tgtccagact gagcatcagc aaagacaact ccaagagtca agttttctta    240
aaaatgaaca gtctgcaaac tgatgacaca gccatgtact actgtgtcat ctataggacg    300
gggtttgctt actggggcca aggactctg gtcactgtct ctgca                     345

<210> SEQ ID NO 69
<211> LENGTH: 336
<212> TYPE: DNA
<213> ORGANISM: Artificial Sequence
<220> FEATURE:
<223> OTHER INFORMATION: ACI-7069-641H1-Ab2 VL

<400> SEQUENCE: 69
gatgttttga tgacccaaac tccactctcc ctgcctgtca gtcttggaga tcaagcctcc     60
atctcttgca gatctagtca gagcattgta catactattg aaacaccta tttagaatgg     120 tacctgcaga aaccaggcca gtctccaaag ctcctgatct acaaagtttc caaccggttt    180
tctggggtcc agacaggtt cagtggcagt ggatcaggga cagatttcac actcaagatc    240
agcagagtgg aggctgagga tctgggagtt tattactgct ttcaaggttc acatgttcca    300
ttcactttcg gctcggggac aaagttggaa ataaaa                              336

<210> SEQ ID NO 70
<211> LENGTH: 113
<212> TYPE: PRT
<213> ORGANISM: Artificial Sequence
<220> FEATURE:
<223> OTHER INFORMATION: ACI-7069-642A10-ab1 VH

<400> SEQUENCE: 70

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Lys Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Met Asp Tyr Trp Gly Gln Gly Thr Ser Val Thr Val Ser
            100                 105                 110

Ser

<210> SEQ ID NO 71
<211> LENGTH: 5
<212> TYPE: PRT
<213> ORGANISM: Artificial Sequence
```

<220> FEATURE:
<223> OTHER INFORMATION: ACI-7069-642A10-ab1 VH CDR1

<400> SEQUENCE: 71

Lys Tyr Trp Met His
1               5

<210> SEQ ID NO 72
<211> LENGTH: 17
<212> TYPE: PRT
<213> ORGANISM: Artificial Sequence
<220> FEATURE:
<223> OTHER INFORMATION: ACI-7069-642A10-ab1 VH CDR2

<400> SEQUENCE: 72

Glu Ile Asn Pro Ser Asn Gly Arg Thr Asn Tyr Asn Glu Lys Phe Lys
1               5                   10                  15

Ser

<210> SEQ ID NO 73
<211> LENGTH: 4
<212> TYPE: PRT
<213> ORGANISM: Artificial Sequence
<220> FEATURE:
<223> OTHER INFORMATION: ACI-7069-642A10-ab1 VH CDR3

<400> SEQUENCE: 73

Tyr Met Asp Tyr
1

<210> SEQ ID NO 74
<211> LENGTH: 112
<212> TYPE: PRT
<213> ORGANISM: Artificial Sequence
<220> FEATURE:
<223> OTHER INFORMATION: ACI-7069-642A10-ab1 VL

<400> SEQUENCE: 74

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Phe Asp Arg
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 75
<211> LENGTH: 16
<212> TYPE: PRT
<213> ORGANISM: Artificial Sequence
<220> FEATURE:
<223> OTHER INFORMATION: ACI-7069-642A10-ab1 VL CDR1

<400> SEQUENCE: 75

Lys Ser Ser Gln Ser Leu Phe Asp Arg Asp Gly Lys Thr Tyr Leu Asn
1               5                   10                  15

<210> SEQ ID NO 76

<400> SEQUENCE: 76

000

<210> SEQ ID NO 77
<211> LENGTH: 9
<212> TYPE: PRT
<213> ORGANISM: Artificial Sequence
<220> FEATURE:
<223> OTHER INFORMATION: ACI-7069-642A10-ab1 VL CDR3

<400> SEQUENCE: 77

Trp Gln Gly Thr His Phe Pro Trp Thr
1               5

<210> SEQ ID NO 78
<211> LENGTH: 339
<212> TYPE: DNA
<213> ORGANISM: Artificial Sequence
<220> FEATURE:
<223> OTHER INFORMATION: ACI-7069-642A10-ab1 VH

<400> SEQUENCE: 78
caggtccaac tgcagcagcc tgggggctgaa ctggtgaagc ctgggggcttc agtgaagctg      60 tcctgcaagg cttctggcta caccttcacc aagtactgga tgcactgggt gaagcagagg     120
cctggacaag gccttgagtg gattggagag attaatccta gcaacggtcg tactaactac     180
aatgagaagt tcaagagcaa ggccacactg actgtagaca atcctccag cacagcctac      240 atgcaactca gcagcctgac atctgaggac tctgcggtct attactgtgc aagatatatg     300
gactactggg gtcaaggaac ctcagtcacc gtctcctca                            339

<210> SEQ ID NO 79
<211> LENGTH: 336
<212> TYPE: DNA
<213> ORGANISM: Artificial Sequence
<220> FEATURE:
<223> OTHER INFORMATION: ACI-7069-642A10-ab1 VL

<400> SEQUENCE: 79
gatgttgtga tgacccagac tccactcact ttgtcggtta ccattggaca accagcctcc      60
atctcttgca agtcaagtca gagcctcttt gatcgtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttccg     300
tggacgttcg gtggaggcac caagctggaa atcaaa                               336

<210> SEQ ID NO 80
<211> LENGTH: 120
<212> TYPE: PRT
<213> ORGANISM: Artificial Sequence
<220> FEATURE:
<223> OTHER INFORMATION: ACI-7069-642D12-Ab1 VH

<400> SEQUENCE: 80

Glu Val Gln Leu Gln Gln Ser Gly Ala Glu Leu Val Lys Pro Gly Ala
1               5                   10                  15

Ser Val Arg Leu Ser Cys Thr Ala Ser Gly Phe Asn Ile Lys Asp Pro

-continued

```
              20              25              30

Tyr Met His Trp Val Arg Gln Arg Pro Lys Gln Gly Leu Glu Trp Ile
        35              40              45

Gly Arg Ile Asp Pro Ala Asp Gly Asn Thr Lys Tyr Asp Pro Lys Phe
    50              55              60

Gln Gly Lys Ala Thr Leu Thr Ala Asp Thr Ser Ser Asn Val Ala Tyr
65              70              75              80

Leu His Leu Ser Ser Leu Thr Ser Glu Asp Thr Ala Val Tyr Tyr Cys
                85              90              95

Ala Arg Phe Tyr Gly Ser Ser His Trp Tyr Phe Asp Val Trp Gly Ala
            100             105             110

Gly Thr Thr Val Thr Val Ser Ser
        115             120
```

<210> SEQ ID NO 81
<211> LENGTH: 5
<212> TYPE: PRT
<213> ORGANISM: Artificial Sequence
<220> FEATURE:
<223> OTHER INFORMATION: ACI-7069-642D12-Ab1 VH CDR1

<400> SEQUENCE: 81

```
Asp Pro Tyr Met His
1           5
```

<210> SEQ ID NO 82
<211> LENGTH: 17
<212> TYPE: PRT
<213> ORGANISM: Artificial Sequence
<220> FEATURE:
<223> OTHER INFORMATION: ACI-7069-642D12-Ab1 VH CDR2

<400> SEQUENCE: 82

```
Arg Ile Asp Pro Ala Asp Gly Asn Thr Lys Tyr Asp Pro Lys Phe Gln
1               5               10              15

Gly
```

<210> SEQ ID NO 83
<211> LENGTH: 11
<212> TYPE: PRT
<213> ORGANISM: Artificial Sequence
<220> FEATURE:
<223> OTHER INFORMATION: ACI-7069-642D12-Ab1 VH CDR3

<400> SEQUENCE: 83

```
Phe Tyr Gly Ser Ser His Trp Tyr Phe Asp Val
1               5               10
```

<210> SEQ ID NO 84
<211> LENGTH: 107
<212> TYPE: PRT
<213> ORGANISM: Artificial Sequence
<220> FEATURE:
<223> OTHER INFORMATION: ACI-7069-642D12-Ab1 VL

<400> SEQUENCE: 84

```
Asp Ile Lys Met Thr Gln Ser Pro Ser Ser Met Tyr Ala Ser Leu Gly
1               5               10              15

Glu Arg Val Thr Ile Thr Cys Lys Ala Ser Gln Asp Ile Lys Arg Tyr
            20              25              30

Leu Ser Trp Tyr Gln Gln Lys Pro Trp Lys Ser Pro Lys Ile Leu Ile
        35              40              45
```

```
Tyr Tyr Ala Thr Ser Leu Ala Asp Gly Val Pro Ser Arg Phe Ser Gly
    50                  55              60

Thr Gly Ser Gly Gln Asp Tyr Ser Leu Thr Ile Ser Ser Leu Glu Ser
65                  70              75                  80

Asp Asp Val Ala Thr Tyr Tyr Cys Leu Gln Gln Gly Glu Ser Pro Tyr
                85                  90              95

Thr Phe Gly Gly Gly Thr Lys Leu Glu Ile Lys
            100                 105
```

```
<210> SEQ ID NO 85
<211> LENGTH: 11
<212> TYPE: PRT
<213> ORGANISM: Artificial Sequence
<220> FEATURE:
<223> OTHER INFORMATION: ACI-7069-642D12-Ab1 VL CDR1

<400> SEQUENCE: 85

Lys Ala Ser Gln Asp Ile Lys Arg Tyr Leu Ser
1               5                   10
```

```
<210> SEQ ID NO 86
<211> LENGTH: 7
<212> TYPE: PRT
<213> ORGANISM: Artificial Sequence
<220> FEATURE:
<223> OTHER INFORMATION: ACI-7069-642D12-Ab1 VL CDR2

<400> SEQUENCE: 86

Tyr Ala Thr Ser Leu Ala Asp
1               5
```

```
<210> SEQ ID NO 87
<211> LENGTH: 9
<212> TYPE: PRT
<213> ORGANISM: Artificial Sequence
<220> FEATURE:
<223> OTHER INFORMATION: ACI-7069-642D12-Ab1 VL CDR3

<400> SEQUENCE: 87

Leu Gln Gln Gly Glu Ser Pro Tyr Thr
1               5
```

```
<210> SEQ ID NO 88
<211> LENGTH: 360
<212> TYPE: DNA
<213> ORGANISM: Artificial Sequence
<220> FEATURE:
<223> OTHER INFORMATION: ACI-7069-642D12-Ab1 VH

<400> SEQUENCE: 88
gaggttcagc tgcagcagtc tgggggcagag cttgtgaagc cggggggcctc agtcaggttg      60 tcctgcacag cttctggctt caacattaaa gaccccctata tgcactgggt caggcagagg     120
cctaaacagg gcctggagtg gattggaagg attgatcctg cggatggtaa tactaaatat     180 gaccccgaagt tccagggcaa ggccactttta acagcagaca catcctccaa tgtagcctac     240
ctgcacctca gcagcctgac atctgaggac actgccgtct attactgtgc tagattctac     300
ggtagtagcc actggtattt cgatgtgtgg ggcgcaggga ccacggtcac cgtctcctca     360
```

```
<210> SEQ ID NO 89
<211> LENGTH: 321
<212> TYPE: DNA
<213> ORGANISM: Artificial Sequence
```

-continued

<220> FEATURE:
<223> OTHER INFORMATION: ACI-7069-642D12-Ab1 VL

<400> SEQUENCE: 89
gacatcaaga tgacccagtc tccatcctcc atgtatgcat cgttgggaga gagagtcact      60
atcacttgca aggcgagtca ggacattaaa aggtatttaa gctggtacca gcagaaacca     120
tggaaatctc ctaagatcct gatctattat gcaacaagct tggcagatgg ggtcccatca     180
agattcagtg gcactggatc tggacaagat tattctctaa ccatcagcag cctggagtct     240
gacgatgtag caacttacta ctgtctacag caaggtgaga gcccgtacac gttcggaggg     300
gggaccaagc tggaaataaa a                                               321

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 115
<212> TYPE: PRT
<213> ORGANISM: Artificial Sequence
<220> FEATURE:
<223> OTHER INFORMATION: ACI-7069-646B7-Ab1 VH

<400> SEQUENCE: 100

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Phe
            20                  25                  30

Gly Val His Trp Val Arg Gln Pro Pro Gly Lys Gly Leu Glu Trp Leu
        35                  40                  45

Gly Ile Met Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Val
                85                  90                  95

Ile Tyr Lys Thr Gly Phe Ala Tyr Trp Gly Gln Gly Thr Leu Val Thr
            100                 105                 110

Val Ser Ala
        115

<210> SEQ ID NO 101
<211> LENGTH: 5
<212> TYPE: PRT
<213> ORGANISM: Artificial Sequence
<220> FEATURE:
<223> OTHER INFORMATION: ACI-7069-646B7-Ab1 VH CDR1

<400> SEQUENCE: 101

Asn Phe Gly Val His
1               5

<210> SEQ ID NO 102
<211> LENGTH: 16
<212> TYPE: PRT
<213> ORGANISM: Artificial Sequence
<220> FEATURE:
<223> OTHER INFORMATION: ACI-7069-646B7-Ab1 VH CDR2

<400> SEQUENCE: 102

Ile Met Trp Ala Gly Gly Ser Thr Asn Tyr Asn Ser Ala Leu Met Ser
1               5                   10                  15

<210> SEQ ID NO 103
<211> LENGTH: 7
<212> TYPE: PRT
<213> ORGANISM: Artificial Sequence
<220> FEATURE:
<223> OTHER INFORMATION: ACI-7069-646B7-Ab1 VH CDR3

<400> SEQUENCE: 103

Tyr Lys Thr Gly Phe Ala Tyr

-continued 1                    5

<210> SEQ ID NO 104
<211> LENGTH: 112
<212> TYPE: PRT
<213> ORGANISM: Artificial Sequence
<220> FEATURE:
<223> OTHER INFORMATION: ACI-7069-646B7-Ab1 VL

<400> SEQUENCE: 104

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ala
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 105
<211> LENGTH: 16
<212> TYPE: PRT
<213> ORGANISM: Artificial Sequence
<220> FEATURE:
<223> OTHER INFORMATION: ACI-7069-646B7-Ab1 VL CDR1

<400> SEQUENCE: 105

Arg Ser Ser Gln Ser Ile Val His Ala Ile Gly Asn Thr Tyr Leu Glu
1               5                   10                  15

<210> SEQ ID NO 106
<211> LENGTH: 7
<212> TYPE: PRT
<213> ORGANISM: Artificial Sequence
<220> FEATURE:
<223> OTHER INFORMATION: ACI-7069-646B7-Ab1 VL CDR2

<400> SEQUENCE: 106

Lys Val Ser Asn Arg Phe Ser
1               5

<210> SEQ ID NO 107
<211> LENGTH: 9
<212> TYPE: PRT
<213> ORGANISM: Artificial Sequence
<220> FEATURE:
<223> OTHER INFORMATION: ACI-7069-646B7-Ab1 VL CDR2

<400> SEQUENCE: 107

Phe Gln Gly Ser His Val Pro Phe Thr
1               5

<210> SEQ ID NO 108
<211> LENGTH: 345
<212> TYPE: DNA
<213> ORGANISM: Artificial Sequence
<220> FEATURE:
<223> OTHER INFORMATION: ACI-7069-646B7-Ab1 VH

<400> SEQUENCE: 108
caggtgcaac tgaaggagtc aggacctggc ctggtggcgc cctcacagag cctgtccatc      60
acttgtactg tctctggatt ttcattaacc aactttggtg tacactgggt tcgccagcct     120
ccaggaaagg gtctggagtg gctgggaata atgtgggctg gtggaagcac aaattataat     180
tcggctctca tgtccagact gagcatcagc aaagacaact ccaagagtca gttttctta     240 aaaatgaaca gtctccaaac tgatgacaca gccatgtact actgtgtcat ctataagacg     300
gggtttgctt actggggcca aggactctg gtcactgtct ctgca                      345

<210> SEQ ID NO 109
<211> LENGTH: 336
<212> TYPE: DNA
<213> ORGANISM: Artificial Sequence
<220> FEATURE:
<223> OTHER INFORMATION: ACI-7069-646B7-Ab1 VL

<400> SEQUENCE: 109
gatgttttga tgacccaaac tccactctcc ctgcctgtca gtcttggaga tcaagcctcc      60
atctcttgca gatctagtca gagcattgta catgctattg gaaacaccta tttagaatgg     120
tacctgcaga aaccaggcca gtctccaaag ctcctgatct acaaagtttc caaccggttt     180
tctggggtcc cagacaggtt cagtggcagt ggatcaggga cagatttcac actcaagatc     240
agcagagtgg aggctgagga tctgggagtt tattactgct ttcaaggttc acatgttcca     300
ttcacgttcg gctcggggac aaagttggaa ataaaa                                336

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

```
<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120
<211> LENGTH: 116
<212> TYPE: PRT
<213> ORGANISM: Artificial Sequence
<220> FEATURE:
<223> OTHER INFORMATION: ACI-7071-712A6-Ab1 VH

<400> SEQUENCE: 120

Gln Val Gln Leu Gln Gln Ser Gly Ala Glu Leu Val Lys Pro Gly Thr
1               5                   10                  15

Ser Val Lys Leu Ser Cys Lys Ala Ser Ala Tyr Thr Phe Thr Glu Tyr
            20                  25                  30

Thr Ile His Trp Ile Lys Gln Lys Ser Gly Gln Gly Leu Glu Trp Ile
        35                  40                  45

Gly Trp Phe His Pro Glu Asn Asp Asn Ile Lys Tyr Asn Glu Asn Phe
    50                  55                  60

Lys Asp Lys Ala Thr Leu Thr Ala Asp Arg Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Gly Thr Ser Gly Tyr Gly Asp Tyr Trp Gly Gln Gly Thr Thr Leu
            100                 105                 110

Thr Val Ser Ser
        115

<210> SEQ ID NO 121
<211> LENGTH: 5
<212> TYPE: PRT
<213> ORGANISM: Artificial Sequence
<220> FEATURE:
<223> OTHER INFORMATION: ACI-7071-712A6-Ab1 VH CDR1

<400> SEQUENCE: 121

Glu Tyr Thr Ile His
1               5

<210> SEQ ID NO 122
<211> LENGTH: 17
<212> TYPE: PRT
```

-continued

```
<213> ORGANISM: Artificial Sequence
<220> FEATURE:
<223> OTHER INFORMATION: ACI-7071-712A6-Ab1 VH CDR2

<400> SEQUENCE: 122

Trp Phe His Pro Glu Asn Asp Asn Ile Lys Tyr Asn Glu Asn Phe Lys
1               5                   10                  15

Asp

<210> SEQ ID NO 123
<211> LENGTH: 7
<212> TYPE: PRT
<213> ORGANISM: Artificial Sequence
<220> FEATURE:
<223> OTHER INFORMATION: ACI-7071-712A6-Ab1 VH CDR3

<400> SEQUENCE: 123

Thr Ser Gly Tyr Gly Asp Tyr
1               5

<210> SEQ ID NO 124
<211> LENGTH: 112
<212> TYPE: PRT
<213> ORGANISM: Artificial Sequence
<220> FEATURE:
<223> OTHER INFORMATION: ACI-7071-712A6-Ab1 VL

<400> SEQUENCE: 124

Asp Val Val Met Thr Gln Ile Pro Leu Thr Leu Ser Ile Thr Ile Gly
1               5                   10                  15

Gln Pro Ala Ser Ile Ser Cys Lys Ser Ser Gln Ser Leu Leu Pro Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Pro Thr Phe Gly Ala Gly Thr Lys Leu Glu Leu Lys
            100                 105                 110

<210> SEQ ID NO 125
<211> LENGTH: 16
<212> TYPE: PRT
<213> ORGANISM: Artificial Sequence
<220> FEATURE:
<223> OTHER INFORMATION: ACI-7071-712A6-Ab1 VL CDR1

<400> SEQUENCE: 125

Lys Ser Ser Gln Ser Leu Leu Pro Ser Asp Gly Lys Thr Tyr Leu Asn
1               5                   10                  15

<210> SEQ ID NO 126

<400> SEQUENCE: 126

000

<210> SEQ ID NO 127
<211> LENGTH: 9
<212> TYPE: PRT
```

<213> ORGANISM: Artificial Sequence
<220> FEATURE:
<223> OTHER INFORMATION: ACI-7071-712A6-Ab1 VL CDR3

<400> SEQUENCE: 127

Trp Gln Gly Thr His Phe Pro Pro Thr
1               5

<210> SEQ ID NO 128
<211> LENGTH: 348
<212> TYPE: DNA
<213> ORGANISM: Artificial Sequence
<220> FEATURE:
<223> OTHER INFORMATION: ACI-7071-712A6-Ab1 VH

<400> SEQUENCE: 128
caggtccagc tgcagcagtc tggagctgag ctggtgaaac ccgggacatc agtgaagctg        60
tcctgtaagg cttctgccta caccttcact gaatatacta tacactggat aaagcagaaa       120
tctggacagg gtcttgagtg gattgggtgg tttcaccctg aaaatgataa tataaagtac       180
aatgagaatt tcaaggacaa ggccacattg actgcggaca gatcctccag cacagtctat       240
atggaactta gtagattgac atctgaagac tctgcggtct atttctgtgc agggacgtca       300
ggctacggag actactgggg ccaaggcacc actctcacag tctcttca                    348

<210> SEQ ID NO 129
<211> LENGTH: 336
<212> TYPE: DNA
<213> ORGANISM: Artificial Sequence
<220> FEATURE:
<223> OTHER INFORMATION: ACI-7071-712A6-Ab1 VL

<400> SEQUENCE: 129
gatgttgtga tgacccagat tccactcact ttgtcgatta ccattggaca accagcctcc        60
atctcttgca agtcaagtca gagcctctta cctagtgatg gaaagacata tttgaattgg       120
ttgttacaga ggccaggcca gtctccaaag cgcctaatct atctggtgtc taaactggac       180
tctggagtcc ctgacaggtt cactggcagt ggatcaggga cagatttcac actgaaaatc       240
agcagagtgg aggctgacga tttgggagtt tattattgct ggcaaggtac acattttcct       300
cctacgttcg gtgctgggac caagctggaa ctgaaa                                  336

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

-continued

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140
<211> LENGTH: 119
<212> TYPE: PRT
<213> ORGANISM: Artificial Sequence
<220> FEATURE:
<223> OTHER INFORMATION: ACI-7071-809D9-Ab2 VH

<400> SEQUENCE: 140

Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Lys Phe Thr Asp Tyr
                20                  25                  30

Ser Met His Trp Val Lys Gln Ser His Thr Lys Ser Leu Glu Trp Ile
            35                  40                  45

Gly Val Ile Ser Thr Tyr Tyr Gly Asp Thr Thr Tyr Asn Gln Lys Phe
        50                  55                  60

Lys Gly Lys Ala Thr Ile Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Thr Tyr Gly Asn Phe Pro Ala Ser Phe Ser Tyr Trp Gly Gln Gly
                100                 105                 110

Thr Leu Val Thr Val Ser Ala
            115

-continued

```
<210> SEQ ID NO 141
<211> LENGTH: 5
<212> TYPE: PRT
<213> ORGANISM: Artificial Sequence
<220> FEATURE:
<223> OTHER INFORMATION: ACI-7071-809D9-Ab2 VH CDR1

<400> SEQUENCE: 141

Asp Tyr Ser Met His
1               5

<210> SEQ ID NO 142
<211> LENGTH: 17
<212> TYPE: PRT
<213> ORGANISM: Artificial Sequence
<220> FEATURE:
<223> OTHER INFORMATION: ACI-7071-809D9-Ab2 VH CDR2

<400> SEQUENCE: 142

Val Ile Ser Thr Tyr Tyr Gly Asp Thr Thr Tyr Asn Gln Lys Phe Lys
1               5               10                  15

Gly

<210> SEQ ID NO 143
<211> LENGTH: 10
<212> TYPE: PRT
<213> ORGANISM: Artificial Sequence
<220> FEATURE:
<223> OTHER INFORMATION: ACI-7071-809D9-Ab2 VH CDR3

<400> SEQUENCE: 143

Tyr Gly Asn Phe Pro Ala Ser Phe Ser Tyr
1               5                   10

<210> SEQ ID NO 144
<211> LENGTH: 112
<212> TYPE: PRT
<213> ORGANISM: Artificial Sequence
<220> FEATURE:
<223> OTHER INFORMATION: ACI-7071-809D9-Ab2 VL

<400> SEQUENCE: 144

Asp Ile Val Met Thr Gln Ala Ala Pro Ser Ile Pro Val Thr Pro Gly
1               5               10                  15

Glu Ser Val Ser Ile Ser Cys Arg Ser Ser Lys Ser Leu Leu His Ser
                20              25                  30

Asn Gly Asn Thr Tyr Leu Tyr Trp Phe Leu Gln Arg Pro Gly Gln Ser
            35              40                  45

Pro Gln Leu Leu Ile Tyr Arg Met Ser Asn Leu Ala Ser Gly Val Pro
        50              55                  60

Asp Arg Phe Ser Gly Ser Gly Ser Gly Thr Ala Phe Thr Leu Arg Ile
65                  70              75                  80

Ser Arg Val Glu Ala Glu Asp Val Gly Val Tyr Tyr Cys Met Gln His
                85              90                  95

Leu Glu Tyr Pro Phe Thr Phe Gly Ser Gly Thr Lys Leu Glu Ile Lys
            100             105                 110

<210> SEQ ID NO 145
<211> LENGTH: 16
<212> TYPE: PRT
<213> ORGANISM: Artificial Sequence
<220> FEATURE:
<223> OTHER INFORMATION: ACI-7071-809D9-Ab2 VL CDR1
```

<400> SEQUENCE: 145

Arg Ser Ser Lys Ser Leu Leu His Ser Asn Gly Asn Thr Tyr Leu Tyr
1               5                   10                  15

<210> SEQ ID NO 146
<211> LENGTH: 7
<212> TYPE: PRT
<213> ORGANISM: Artificial Sequence
<220> FEATURE:
<223> OTHER INFORMATION: ACI-7071-809D9-Ab2 VL CDR2

<400> SEQUENCE: 146

Arg Met Ser Asn Leu Ala Ser
1               5

<210> SEQ ID NO 147
<211> LENGTH: 9
<212> TYPE: PRT
<213> ORGANISM: Artificial Sequence
<220> FEATURE:
<223> OTHER INFORMATION: ACI-7071-809D9-Ab2 VL CDR3

<400> SEQUENCE: 147

Met Gln His Leu Glu Tyr Pro Phe Thr
1               5

<210> SEQ ID NO 148
<211> LENGTH: 357
<212> TYPE: DNA
<213> ORGANISM: Artificial Sequence
<220> FEATURE:
<223> OTHER INFORMATION: ACI-7071-809D9-Ab2 VH

<400> SEQUENCE: 148
caggtccagc tgcagcagtc tggggctgag ctggtgaggc ctggggtctc agtgaagatt      60
tcctgcaagg gttctggcta caaattcact gattattcta tgcactgggt gaaacagagt     120
catacaaaga gtctagagtg gattggagtt attagtactt actatggtga tactacctac     180
aaccagaaat tcaagggcaa ggccacaatc actgtagaca atcctccag cacagcctat     240 atggaacttg ccagactgac atctgaggat tctgccatct attactgtgc aacgtacggt     300
aacttcccgg cctcattttc ttactggggc caagggactc tggtcactgt ctctgca       357

<210> SEQ ID NO 149
<211> LENGTH: 336
<212> TYPE: DNA
<213> ORGANISM: Artificial Sequence
<220> FEATURE:
<223> OTHER INFORMATION: ACI-7071-809D9-Ab2 VL

<400> SEQUENCE: 149
gatattgtga tgactcaggc tgcaccctct atacctgtca ctcctggaga gtcagtatcc      60
atctcctgca ggtctagtaa gagtctcctg catagtaatg caacactta cttgtattgg     120 ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtgtt attactgta tgcaacatct agaatatcca     300
ttcacgttcg gctcggggac aaagttggaa ataaaa                               336

<210> SEQ ID NO 150
<211> LENGTH: 121
<212> TYPE: PRT

-continued

```
<213> ORGANISM: Artificial Sequence
<220> FEATURE:
<223> OTHER INFORMATION: ACI-7071-809F12-Ab1 VH

<400> SEQUENCE: 150

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Asn Arg Asn
                20                  25                  30

Gly Val Gln Trp Val Arg Gln Pro Pro Gly Lys Gly Leu Glu Trp Leu
            35                  40                  45

Gly Val Ile Trp Pro Gly Gly Ser Thr Asn Cys Asn Ser Ala Leu Met
        50                  55                  60

Ser Arg Leu Ser Ile Ser Lys Asp Asn Ser Lys Ser Gln Val Phe Leu
65                  70                  75                  80

Lys Met Asn Ser Leu His Thr Asp Asp Thr Gly Ile Tyr Tyr Cys Ala
                85                  90                  95

Arg Val Gly Gly Asn Tyr Val Trp Asp Tyr Asn Asn Tyr Ala Trp Gly
            100                 105                 110

Gln Gly Thr Leu Val Thr Val Ser Ala
        115                 120

<210> SEQ ID NO 151
<211> LENGTH: 5
<212> TYPE: PRT
<213> ORGANISM: Artificial Sequence
<220> FEATURE:
<223> OTHER INFORMATION: ACI-7071-809F12-Ab1 VH CDR1

<400> SEQUENCE: 151

Arg Asn Gly Val Gln
1               5

<210> SEQ ID NO 152
<211> LENGTH: 16
<212> TYPE: PRT
<213> ORGANISM: Artificial Sequence
<220> FEATURE:
<223> OTHER INFORMATION: ACI-7071-809F12-Ab1 VH CDR2

<400> SEQUENCE: 152

Val Ile Trp Pro Gly Gly Ser Thr Asn Cys Asn Ser Ala Leu Met Ser
1               5                   10                  15

<210> SEQ ID NO 153
<211> LENGTH: 13
<212> TYPE: PRT
<213> ORGANISM: Artificial Sequence
<220> FEATURE:
<223> OTHER INFORMATION: ACI-7071-809F12-Ab1 VH CDR3

<400> SEQUENCE: 153

Val Gly Gly Asn Tyr Val Trp Asp Tyr Asn Asn Tyr Ala
1               5                   10

<210> SEQ ID NO 154
<211> LENGTH: 112
<212> TYPE: PRT
<213> ORGANISM: Artificial Sequence
<220> FEATURE:
<223> OTHER INFORMATION: ACI-7071-809F12-Ab1 VL

<400> SEQUENCE: 154
```

-continued

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Arg
                100                 105                 110
```

<210> SEQ ID NO 155
<211> LENGTH: 16
<212> TYPE: PRT
<213> ORGANISM: Artificial Sequence
<220> FEATURE:
<223> OTHER INFORMATION: ACI-7071-809F12-Ab1 VL CDR1

<400> SEQUENCE: 155

```
Arg Ser Ser Gln Asn Ile Val His Ser Ile Gly Asn Thr Tyr Leu Glu
1               5                   10                  15
```

<210> SEQ ID NO 156
<211> LENGTH: 7
<212> TYPE: PRT
<213> ORGANISM: Artificial Sequence
<220> FEATURE:
<223> OTHER INFORMATION: ACI-7071-809F12-Ab1 VL CDR2

<400> SEQUENCE: 156

```
Lys Val Ser Asn Arg Phe Ser
1               5
```

<210> SEQ ID NO 157
<211> LENGTH: 9
<212> TYPE: PRT
<213> ORGANISM: Artificial Sequence
<220> FEATURE:
<223> OTHER INFORMATION: ACI-7071-809F12-Ab1 VL CDR3

<400> SEQUENCE: 157

```
Phe Gln Gly Ser His Val Pro Tyr Thr
1               5
```

<210> SEQ ID NO 158
<211> LENGTH: 363
<212> TYPE: DNA
<213> ORGANISM: Artificial Sequence
<220> FEATURE:
<223> OTHER INFORMATION: ACI-7071-809F12-Ab1 VH

<400> SEQUENCE: 158

```
caggtgcagc tgaaggagtc aggacctggc ctggtggcgc cctcacagag cctgtccatc      60
acttgcactg tctctgggtt ttcgttaaac agaaatggtg tacagtgggt tcgccagcct     120
ccaggaaagg gtctggagtg gctgggagta atatggcctg cggaagcac aaattgtaat      180 tcggctctca tgtccagact gagcatcagc aaagacaact ccaagagtca gttttctta      240 aaaatgaaca gtctgcacac tgatgacaca ggcatatatt actgtgccag agtagggggt     300
```

-continued

```
aactacgtgt gggactataa taactacgcc tggggccaag ggactctggt cactgtctct     360
gca                                                                   363

<210> SEQ ID NO 159
<211> LENGTH: 336
<212> TYPE: DNA
<213> ORGANISM: Artificial Sequence
<220> FEATURE:
<223> OTHER INFORMATION: ACI-7071-809F12-Ab1 VL

<400> SEQUENCE: 159
gatgttttga tgacccaaac tccactctcc ctgcctgtca gtcttggaga tcaggcctcc      60
atctcttgca gatctagtca gaacattgta catagtattg gaaacaccta tttagagtgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg gaggggggac caagctagaa ataaga                              336
```